US006946274B2

(12) United States Patent
Kapeller-Libermann

(10) Patent No.: US 6,946,274 B2
(45) Date of Patent: Sep. 20, 2005

(54) 13245, A NOVEL HUMAN MYOTONIC DYSTROPHY TYPE PROTEIN KINASE AND USES THEREFOR

(75) Inventor: Rosana Kapeller-Libermann, Chestnut Hill, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 450 days.

(21) Appl. No.: 10/017,216

(22) Filed: Oct. 23, 2001

(65) Prior Publication Data

US 2002/0160483 A1 Oct. 31, 2002

Related U.S. Application Data

(60) Provisional application No. 60/242,429, filed on Oct. 23, 2000.

(51) Int. Cl.[7] .......................... C12N 1/20; C12N 9/20; C12N 15/00; C12Q 1/68; C07H 21/04

(52) U.S. Cl. ........................ 435/194; 435/6; 435/252.3; 435/320.1; 435/325; 536/23.2

(58) Field of Search ......................... 435/194, 6, 252.3, 435/320.1, 325; 536/23.2

(56) References Cited

FOREIGN PATENT DOCUMENTS

WO WO 01/38503 A2 5/2001

OTHER PUBLICATIONS

"Human Protein Kinase and Protein Kinase–Like Enzymes", Jun. 22, 2001 (sequence) srs@EMBL–EBI [online], Hinxton, Cambridge, UK: European Bioinformatics Institute [retrieved on May 22, 2002]. Retrieved from the Internet search of EMBL databank: EMBL Accession No. AX166567.

Madaule, P. et al., "Mus Musculus Citron, Putative rho/rac effector, mRNA, complete cds." Dec. 30, 1995 [sequence] GenBank [online] Bethesda, MD, USA: National Center for Biotechnology Information [retrieved on Jan. 31, 2005]. GenBank Accession No. U39904.

DiCunto, F. et al., "Mus Musculus rho/rac–interacting Citron Kinase (Crik) mRNA, complete cds." Nov. 11, 1998 (sequence) GenBank [online] Bethesda, MD, USA: National Center for Biotechnology Information [retrieved on Jan. 31, 2005]. Retrieved from the Internet: GenBank Accession No. AF086824.

Zhang, W. et al., "Rattus Norvegicus Postsynaptic Density Protein (Citron) mRNA, complete cds." Jul. 2, 1998 (sequence) GenBank [online] Bethesda, MD, USA: National Center for Biotechnology Information [retrieved on Jan. 31, 2005]. Retrieved from the Internet: GenBank Accession No. AF039218.

Nagase, T. et al., "Homo Sapiens mRNA for KIAA0949 Protein, Partial cds." Jan. 28, 2005 (sequence) GenBank [online] Bethesda, MD, USA: National Center for Biotechnology Information [retrieved on Jan. 31, 2005]. Retrieved from the Internet: URL: GenBank Accession No. AB023166.

"Oa56c11.r1 NCI_CGAP_GCB1 Homo Sapiens cDNA Clone IMAGE: 1308980 5', mRNA sequence" Jan. 27, 1998 (sequence) GenBank [online] Bethesda, MD, USA: National Center for Biotechnology Information [retrieved on Jan. 31, 2005]. Retrieved from the Internet: GenBank Accession No. AA746301.

Chahine, M. et al., "Myotonic Dystrophy Kinase Modulates Skeletal Muscle but not Cardiac Voltage–Gated Sodium Channels", FEBS Letters 412:621–624 (1997).

Bush et al., "Myotonic dystrophy protein kinase domains mediate localization, oligomerization, novel catalytic activity, and autoInhibition," Biochem. 39(29):8480–8490 (2000).

Dicunto et al., "Citron rho–interacting kinase, a novel tissue–specific ser/thr kinase encompassing the rho–rac–binding protein citron," J. Biolog. Chem. 273(45):29706–29711 (1998).

Madaule et al., "A novel partner for the GTP–bound forms of rho and rac," FEBS Letters 377:243–248 (1995).

Nagase et al., "Prediction of the coding sequences of unidentified human genes. XIII. The complete sequences of 100 new cDNA clones from brain which code for large proteins in vitro," DNA Res. 6:63–70 (1999).

Zhao et al., "Cloning and chromosomal location of a novel member of the myotonic dystrophy family of protein kinases," J. Biolog. Chem. 272(15):10013–10020 (1997).

GenBank® Database, Accession No. AAC27933, Jul. 31, 1998.

GenBank® Database, Accession No. AAC72823, Nov. 10, 1998.

GenBank® Database, Accession No. O14578, May 30, 2000.

GenBank® Database, Accession No. P49025, May 30, 2000.

(Continued)

*Primary Examiner*—Maryam Monshipouri
(74) *Attorney, Agent, or Firm*—Millennium Pharmaceuticals, Inc.

(57) ABSTRACT

The invention provides isolated nucleic acids molecules, designated 13245 nucleic acid molecules, which encode a novel myotonic dystrophy type protein kinase. The invention also provides antisense nucleic acid molecules, recombinant expression vectors containing 13245 nucleic acid molecules, host cells into which the expression vectors have been introduced, and non-human transgenic animals in which a 13245 gene has been introduced or disrupted. The invention still further provides isolated 13245 proteins, fusion proteins, antigenic peptides and anti-13245 antibodies. Diagnostic methods utilizing compositions of the invention are also provided.

9 Claims, 25 Drawing Sheets

OTHER PUBLICATIONS

Matsui, Rho–associated kinase, a novel serine/threonine kinase, as a putative target for small GTP binding protein, Rho, Embo. J. 15(9):2208–2216, 1996 (Abstract only).

Madaule et al., Role of citron kinase as target of the small GT Pase Rho in cytokinesis, Nature 394(6692):491–494, 1998 (Abstract only).

Madaule et al., Citron, a Rho target that effects contractility during cytokines, Micros. Res. Tech. 49(2):123–126, 2000 (Abstract only).

Burbelo et al., A Conserved Binding Motif Defines Numerous Candidate Target Proteins For Both Cdc42 and Rac GTPases, J. Biol. Chem., 270(49):29071–29074, 1995.

Ferdinando et al., Citron Rho–interacting Kinase, a Novel Tissue–specific Ser/Thr Kinase Encompassing the Rho–Rac–binding Protein Citron, J. Biol. Chem., 273(45):29706–29711, 1998.

Fujisawa et al., Identification of the Rho–binding Domain of $p160^{ROCK}$, a Rho–associated Coiled–coil Containing Protein Kinase, J. Biol. Chem., 271(38):23022–23028, 1996.

```
                   M   L   K   F   K   Y   G   A   R   N   P   L   D   A   G    15
AGAGCCGCCAGTGGGGAG ATG TTG AAG TTC AAA TAT GGA GCG CGG AAT CCT TTG GAT GCT GGT   45

 A   A   E   P   I   A   S   R   A   S   R   L   N   L   F   F   Q   G   K   P    35
GCT GCT GAA CCC ATT GCC AGC CGG GCC TCC AGG CTG AAT CTG TTC TTC CAG GGG AAA CCA  105

 P   F   M   T   Q   Q   Q   M   S   P   L   S   R   E   G   I   L   D   A   L    55
CCC TTT ATG ACT CAA CAG CAG ATG TCT CCT CTT TCC CGA GAA GGG ATA TTA GAT GCC CTC  165

 F   V   L   F   E   E   C   S   Q   P   A   L   M   K   I   K   H   V   S   N    75
TTT GTT CTC TTT GAA GAA TGC AGT CAG CCT GCT CTG ATG AAG ATT AAG CAC GTG AGC AAC  225

 F   V   R   K   Y   S   D   T   I   A   E   L   Q   E   L   Q   P   S   A   K    95
TTT GTC CGG AAG TAT TCC GAC ACC ATA GCT GAG TTA CAG GAG CTC CAG CCT TCG GCA AAG  285

 D   F   E   V   R   S   L   V   G   C   G   H   F   A   E   V   Q   V   V   R   115
GAC TTC GAA GTC AGA AGT CTT GTA GGT TGT GGT CAC TTT GCT GAA GTG CAG GTG GTA AGA  345

 E   K   A   T   G   D   I   Y   A   M   K   V   M   K   K   K   A   L   L   A   135
GAG AAA GCA ACC GGG GAC ATC TAT GCT ATG AAA GTG ATG AAG AAG AAG GCT TTA TTG GCC  405

 Q   E   Q   V   S   F   F   E   E   E   R   N   I   L   S   R   S   T   S   P   155
CAG GAG CAG GTT TCA TTT TTT GAG GAA GAG CGG AAC ATA TTA TCT CGA AGC ACA AGC CCG  465
```

Fig. 1A

```
 W   I   P   Q   L   Q   Y   A   F   Q   D   K   N   H   L   Y   L   M   E   E    175
TGG ATC CCC CAA TTA CAG TAT GCC TTT CAG GAC AAA AAT CAC CTT TAT CTG ATG GAG GAA   525

 Y   Q   P   G   G   D   L   L   S   L   L   N   R   Y   E   D   Q   L   D   E    195
TAT CAG CCT GGA GGG GAC TTG CTG TCA CTT TTG AAT AGA TAT GAG GAC CAG TTA GAT GAA   585

 N   L   I   Q   F   Y   L   A   E   L   I   L   A   V   H   S   V   H   L   M    215
AAC CTG ATA CAG TTT TAC CTA GCT GAG CTG ATT TTG GCT GTT CAC AGC GTT CAT CTG ATG   645

 G   Y   V   H   R   D   I   K   P   E   N   I   L   V   D   R   T   G   H   I    235
GGA TAC GTG CAT CGA GAC ATC AAG CCT GAG AAC ATT CTC GTT GAC CGC ACA GGA CAC ATC   705

 K   L   V   D   F   G   S   A   A   K   M   N   S   N   K   M   V   N   A   K    255
AAG CTG GTG GAT TTT GGA TCT GCC GCG AAA ATG AAT TCA AAC AAG ATG GTG AAT GCC AAA   765

 L   P   I   G   T   P   D   Y   M   A   P   E   V   L   T   V   M   N   G   D    275
CTC CCG ATT GGG ACC CCA GAT TAC ATG GCT CCT GAA GTG CTG ACT GTG ATG AAC GGG GAT   825

 G   K   G   T   Y   G   L   D   C   D   W   W   S   V   G   V   I   A   Y   E    295
GGA AAA GGC ACC TAC GGC CTG GAC TGT GAC TGG TGG TCA GTG GGC GTG ATT GCC TAT GAG   885

 M   I   Y   G   R   S   P   F   A   E   G   T   S   A   R   T   F   N   N   I    315
ATG ATT TAT GGG AGA TCC CCC TTC GCA GAG GGA ACC TCT GCC AGA ACC TTC AAT AAC ATT   945
```

Fig. 1B

```
 M   N   F   Q   R   F   L   K   F   P   D   D   P   K   V   S   S   D   F   L     335
ATG AAT TTC CAG CGG TTT TTG AAA TTT CCA GAT GAC CCC AAA GTG AGC AGT GAC TTT CTT   1005

 D   L   I   Q   S   L   L   C   G   Q   K   E   R   L   K   F   E   G   L   C     355
GAT CTG ATT CAA AGC TTG TTG TGC GGC CAG AAA GAG AGA CTG AAG TTT GAA GGT CTT TGC   1065

 C   H   P   F   F   S   K   I   D   W   N   N   I   R   N   S   P   P   P   F     375
TGC CAT CCT TTC TTC TCT AAA ATT GAC TGG AAC AAC ATT CGT AAC TCT CCT CCC CCC TTC   1125

 V   P   T   L   K   S   D   D   D   T   S   N   F   D   E   P   E   K   N   S     395
GTT CCC ACC CTC AAG TCT GAC GAT GAC ACC TCC AAT TTT GAT GAA CCA GAG AAG AAT TCG   1185

 W   V   S   S   S   P   C   Q   L   S   P   S   G   F   S   G   E   E   L   P     415
TGG GTT TCA TCC TCT CCG TGC CAG CTG AGC CCC TCA GGC TTC TCG GGT GAA GAA CTG CCG   1245

 F   V   G   F   S   Y   S   K   A   L   G   I   L   G   R   S   E   S   V   V     435
TTT GTG GGG TTT TCG TAC AGC AAG GCA CTG GGG ATT CTT GGT AGA TCT GAG TCT GTT GTG   1305

 S   G   L   D   S   P   A   K   T   S   S   M   E   K   K   L   L   I   K   S     455
TCG GGT CTG GAC TCC CCT GCC AAG ACT AGC TCC ATG GAA AAG AAA CTT CTC ATC AAA AGC   1365

 K   E   L   Q   D   S   Q   D   K   C   H   K   M   E   Q   E   M   T   R   L     475
AAA GAG CTA CAA GAC TCT CAG GAC AAG TGT CAC AAG ATG GAG CAG GAA ATG ACC CGG TTA   1425
```

Fig. 1C

```
 H   R   R   V   S   E   V   E   A   V   L   S   Q   K   E   V   E   L   K   A     495
CAT CGG AGA GTG TCA GAG GTG GAG GCT GTG CTT AGT CAG AAG GAG GTG GAG CTG AAG GCC   1485

 S   E   T   Q   R   S   L   L   E   Q   D   L   A   T   Y   I   T   E   C   S     515
TCT GAG ACT CAG AGA TCC CTC CTG GAG CAG GAC CTT GCT ACC TAC ATC ACA GAA TGC AGT   1545

 S   L   K   R   S   L   E   Q   A   R   M   E   V   S   Q   E   D   D   K   A     535
AGC TTA AAG CGA AGT TTG GAG CAA GCA CGG ATG GAG GTG TCC CAG GAG GAT GAC AAA GCA   1605

 L   Q   L   L   H   D   I   R   E   Q   S   R   K   L   Q   E   I   K   E   Q     555
CTG CAG CTT CTC CAT GAT ATC AGA GAG CAG AGC CGG AAG CTC CAA GAA ATC AAA GAG CAG   1665

 E   Y   Q   A   Q   V   E   E   M   R   L   M   M   N   Q   L   E   E   D   L     575
GAG TAC CAG GCT CAA GTG GAA GAA ATG AGG TTG ATG ATG AAT CAG TTG GAA GAG GAT CTT   1725

 V   S   A   R   R   R   S   D   L   Y   E   S   E   L   R   E   S   R   L   A     595
GTC TCA GCA AGA AGA CGG AGT GAT CTC TAC GAA TCT GAG CTG AGA GAG TCT CGG CTT GCT   1785

 A   E   E   F   K   R   K   A   T   E   C   Q   H   K   L   L   K   A   K   D     615
GCT GAA GAA TTC AAG CGG AAA GCG ACA GAA TGT CAG CAT AAA CTG TTG AAG GCT AAG GAT   1845

 Q   G   K   P   E   V   G   E   Y   A   K   L   E   K   I   N   A   E   Q   Q     635
CAA GGG AAG CCT GAA GTG GGA GAA TAT GCG AAA CTG GAG AAG ATC AAT GCT GAG CAG CAG   1905
```

Fig. 1D

```
 L   K   I   Q   E   L   Q   E   K   L   E   K   A   A   K   E   R   A   E   R    655
CTC AAA ATT CAG GAG CTC CAA GAG AAA CTG GAG AAG GCT GCA AAG GAG CGA GCC GAG AGG  1965

 E   L   E   K   L   Q   N   R   E   D   S   S   E   G   I   R   K   K   L   V    675
GAG CTG GAG AAG CTG CAG AAC CGA GAG GAT TCT TCT GAA GGC ATC AGA AAG AAG CTG GTG  2025

 E   A   E   E   R   R   H   S   L   E   N   K   V   K   R   L   E   T   M   E    695
GAA GCT GAG GAA CGC CGC CAT TCT CTG GAG AAC AAG GTA AAG AGA CTA GAG ACC ATG GAG  2085

 R   R   E   N   R   L   K   D   D   I   Q   T   K   S   Q   Q   I   Q   Q   M    715
CGT AGA GAA AAC AGA CTG AAG GAT GAC ATC CAG ACA AAA TCC CAA CAG ATC CAG CAG ATG  2145

 A   D   K   I   L   E   L   E   E   K   H   R   E   A   Q   V   S   A   Q   H    735
GCT GAT AAA ATT CTG GAG CTC GAA GAG AAA CAT CGG GAG GCC CAA GTC TCA GCC CAG CAC  2205

 L   E   V   H   L   K   Q   K   E   Q   H   Y   E   E   K   I   K   V   L   D    755
CTA GAA GTG CAC CTG AAA CAG AAA GAG CAG CAC TAT GAG GAA AAG ATT AAA GTG TTG GAC  2265

 N   Q   I   K   K   D   L   A   D   K   E   T   L   E   N   M   M   Q   R   H    775
AAT CAG ATA AAG AAA GAC CTG GCT GAC AAG GAG ACA CTG GAG AAC ATG ATG CAG AGA CAC  2325

 E   E   E   A   H   E   K   G   K   I   L   S   E   Q   K   A   M   I   N   A    795
GAG GAG GAG GCC CAT GAG AAG GGC AAA ATT CTC AGC GAA CAG AAG GCG ATG ATC AAT GCT  2385
```

Fig. 1E

```
 M   D   S   K   I   R   S   L   E   Q   R   I   V   E   L   S   E   A   N   K      815
ATG GAT TCC AAG ATC AGA TCC CTG GAA CAG AGG ATT GTG GAA CTG TCT GAA GCC AAT AAA    2445

 L   A   A   N   S   S   L   F   T   Q   R   N   M   K   A   Q   E   E   M   I      835
CTT GCA GCA AAT AGC AGT CTT TTT ACC CAA AGG AAC ATG AAG GCC CAA GAA GAG ATG ATT    2505

 S   E   L   R   Q   Q   K   F   Y   L   E   T   Q   A   G   K   L   E   A   Q      855
TCT GAA CTC AGG CAA CAG AAA TTT TAC CTG GAG ACA CAG GCT GGG AAG TTG GAG GCC CAG    2565

 N   R   K   L   E   E   Q   L   E   K   I   S   H   Q   D   H   S   D   K   N      875
AAC CGA AAA CTG GAG GAG CAG CTG GAG AAG ATC AGC CAC CAA GAC CAC AGT GAC AAG AAT    2625

 R   L   L   E   L   E   T   R   L   R   E   V   S   L   E   H   E   E   Q   K      895
CGG CTG CTG GAA CTG GAG ACA AGA TTG CGG GAG GTC AGT CTA GAG CAC GAG GAG CAG AAA    2685

 L   E   L   K   R   Q   L   T   E   L   Q   L   S   L   Q   E   R   E   S   Q      915
CTG GAG CTC AAG CGC CAG CTC ACA GAG CTA CAG CTC TCC CTG CAG GAG CGC GAG TCA CAG    2745

 L   T   A   L   Q   A   A   R   A   A   L   E   S   Q   L   R   Q   A   K   T      935
TTG ACA GCC CTG CAG GCT GCA CGG GCG GCC CTG GAG AGC CAG CTT CGC CAG GCG AAG ACA    2805

 E   L   E   E   T   T   A   E   A   E   E   E   I   Q   A   L   T   A   H   R      955
GAG CTG GAA GAG ACC ACA GCA GAA GCT GAA GAG GAG ATC CAG GCA CTC ACG GCA CAT AGA    2865
```

Fig. 1F

```
 D   E   I   Q   R   K   F   D   A   L   R   N   S   C   T   V   I   T   D   L    975
GAT GAA ATC CAG CGC AAA TTT GAT GCT CTT CGT AAC AGC TGT ACT GTA ATC ACA GAC CTG  2925

 E   E   Q   L   N   Q   L   T   E   D   N   A   E   L   N   N   Q   N   F   Y    995
GAG GAG CAG CTA AAC CAG CTG ACC GAG GAC AAC GCT GAA CTC AAC AAC CAA AAC TTC TAC  2985

 L   S   K   Q   L   D   E   A   S   G   A   N   D   E   I   V   Q   L   R   S   1015
TTG TCC AAA CAA CTC GAT GAG GCT TCT GGC GCC AAC GAC GAG ATT GTA CAA CTG CGA AGT  3045

 E   V   D   H   L   R   R   E   I   T   E   R   E   M   Q   L   T   S   Q   K   1035
GAA GTG GAC CAT CTC CGC CGG GAG ATC ACG GAA CGA GAG ATG CAG CTT ACC AGC CAG AAG  3105

 Q   T   M   E   A   L   K   T   T   C   T   M   L   E   E   Q   V   M   D   L   1055
CAA ACG ATG GAG GCT CTG AAG ACC ACG TGC ACC ATG CTG GAG GAA CAG GTC ATG GAT TTG  3165

 E   A   L   N   D   E   L   L   E   K   E   R   Q   W   E   A   W   R   S   V   1075
GAG GCC CTA AAC GAT GAG CTG CTA GAA AAA GAG CGG CAG TGG GAG GCC TGG AGG AGC GTC  3225

 L   G   D   E   K   S   Q   F   E   C   R   V   R   E   L   Q   R   M   L   D   1095
CTG GGT GAT GAG AAA TCC CAG TTT GAG TGT CGG GTT CGA GAG CTG CAG AGA ATG CTG GAC  3285

 T   E   K   Q   S   R   A   R   A   D   Q   R   I   T   E   S   R   Q   V   V   1115
ACC GAG AAA CAG AGC AGG GCG AGA GCC GAT CAG CGG ATC ACC GAG TCT CGC CAG GTG GTG  3345
```

Fig. 1G

```
 E   L   A   V   K   E   H   K   A   E   I   L   A   L   Q   Q   A   L   K   E   1135
GAG CTG GCA GTG AAG GAG CAC AAG GCT GAG ATT CTC GCT CTG CAG CAG GCT CTC AAA GAG  3405

 Q   K   L   K   A   E   S   L   S   D   K   L   N   D   L   E   K   K   H   A   1155
CAG AAG CTG AAG GCC GAG AGC CTC TCT GAC AAG CTC AAT GAC CTG GAG AAG AAG CAT GCT  3465

 M   L   E   M   N   A   R   S   L   Q   Q   K   L   E   T   E   R   E   L   K   1175
ATG CTT GAA ATG AAT GCC CGA AGC TTA CAG CAG AAG CTG GAG ACT GAA CGA GAG CTC AAA  3525

 Q   R   L   L   E   E   Q   A   K   L   Q   Q   Q   M   D   L   Q   K   N   H   1195
CAG AGG CTT CTG GAA GAG CAA GCC AAA TTA CAG CAG CAG ATG GAC CTG CAG AAA AAT CAC  3585

 I   F   R   L   T   Q   G   L   Q   E   A   L   D   R   A   D   L   L   K   T   1215
ATT TTC CGT CTG ACT CAA GGA CTG CAA GAA GCT CTA GAT CGG GCT GAT CTA CTG AAG ACA  3645

 E   R   S   D   L   E   Y   Q   L   E   N   I   Q   V   L   Y   S   H   E   K   1235
GAA AGA AGT GAC TTG GAG TAT CAG CTG GAA AAC ATT CAG GTT CTC TAT TCT CAT GAA AAG  3705

 V   K   M   E   G   T   I   S   Q   Q   T   K   L   I   D   F   L   Q   A   K   1255
GTG AAA ATG GAA GGC ACT ATT TCT CAA CAA ACC AAA CTC ATT GAT TTT CTG CAA GCC AAA  3765

 M   D   Q   P   A   K   K   K   K   G   L   F   S   R   R   K   E   D   P   A   1275
ATG GAC CAA CCT GCT AAA AAG AAA AAG GGT TTA TTT AGT CGA CGG AAA GAG GAC CCT GCT  3825
```

Fig. 1H

```
 L   P   T   Q   V   P   L   Q   Y   N   E   L   K   L   A   L   E   K   E   K    1295
TTA CCC ACA CAG GTT CCT CTG CAG TAC AAT GAG CTG AAG CTG GCC CTG GAG AAG GAG AAA   3885

 A   R   C   A   E   L   E   E   A   L   Q   K   T   R   I   E   L   R   S   A    1315
GCT CGC TGT GCA GAG CTA GAG GAA GCC CTT CAG AAG ACC CGC ATC GAG CTC CGG TCC GCC   3945

 R   E   E   A   A   H   R   K   A   T   D   H   P   H   P   S   T   P   A   T    1335
CGG GAG GAA GCT GCC CAC CGC AAA GCA ACG GAC CAC CCA CAC CCA TCC ACG CCA GCC ACC   4005

 A   R   Q   Q   I   A   M   S   A   I   V   R   S   P   E   H   Q   P   S   A    1355
GCG AGG CAG CAG ATC GCC ATG TCC GCC ATC GTG CGG TCG CCA GAG CAC CAG CCC AGT GCC   4065

 M   S   L   L   A   P   P   S   S   R   R   K   E   S   S   T   P   E   E   F    1375
ATG AGC CTG CTG GCC CCG CCA TCC AGC CGC AGA AAG GAG TCT TCA ACT CCA GAG GAA TTT   4125

 S   R   R   L   K   E   R   M   H   H   N   I   P   H   R   F   N   V   G   L    1395
AGT CGG CGT CTT AAG GAA CGC ATG CAC CAC AAT ATT CCT CAC CGA TTC AAC GTA GGA CTG   4185

 N   M   R   A   T   K   C   A   V   C   L   D   T   V   H   F   G   R   Q   A    1415
AAC ATG CGA GCC ACA AAG TGT GCT GTG TGT CTG GAT ACC GTG CAC TTT GGA CGC CAG GCA   4245

 S   K   C   L   E   C   Q   V   M   C   H   P   K   C   S   T   C   L   P   A    1435
TCC AAA TGT CTC GAA TGT CAG GTG ATG TGT CAC CCC AAG TGC TCC ACG TGC TTG CCA GCC   4305
```

Fig. 1I

```
 T   C   G   L   P   A   E   Y   A   T   H   F   T   E   A   F   C   R   D   K   1455
ACC TGC GGC TTG CCT GCT GAA TAT GCC ACA CAC TTC ACC GAG GCC TTC TGC CGT GAC AAA  4365

 M   N   S   P   G   L   Q   T   K   E   P   S   S   S   L   H   L   E   G   W   1475
ATG AAC TCC CCA GGT CTC CAG ACC AAG GAG CCC AGC AGC AGC TTG CAC CTG GAA GGG TGG  4425

 M   K   V   P   R   N   N   K   R   G   Q   Q   G   W   D   R   K   Y   I   V   1495
ATG AAG GTG CCC AGG AAT AAC AAA CGA GGA CAG CAA GGC TGG GAC AGG AAG TAC ATT GTC  4485

 L   E   G   S   K   V   L   I   Y   D   N   E   A   R   E   A   G   Q   R   P   1515
CTG GAG GGA TCA AAA GTC CTC ATT TAT GAC AAT GAA GCC AGA GAA GCT GGA CAG AGG CCG  4545

 V   E   E   F   E   L   C   L   P   D   G   D   V   S   I   H   G   A   V   G   1535
GTG GAA GAA TTT GAG CTG TGC CTT CCC GAC GGG GAT GTA TCT ATT CAT GGT GCC GTT GGT  4605

 A   S   E   L   A   N   T   A   K   A   E   K   A   E   A   D   A   K   L   L   1555
GCT TCC GAA CTC GCA AAT ACA GCC AAA GCA GAA AAA GCA GAA GCT GAT GCT AAA CTG CTT  4665

 G   N   S   L   L   K   L   E   G   D   D   R   L   D   M   N   C   T   L   P   1575
GGA AAC TCC CTG CTG AAA CTG GAA GGT GAT GAC CGT CTA GAC ATG AAC TGC ACG CTG CCC  4725

 F   S   D   Q   V   V   L   V   G   T   E   E   G   L   Y   A   L   N   V   L   1595
TTC AGT GAC CAG GTG GTG TTG GTG GGC ACC GAG GAA GGG CTC TAC GCC CTG AAT GTC TTG  4785
```

Fig. 1J

```
 K   N   S   L   T   H   V   P   G   I   G   A   V   F   Q   I   Y   I   I   K   1615
AAA AAC TCC CTA ACC CAT GTC CCA GGA ATT GGA GCA GTC TTC CAA ATT TAT ATT ATC AAG  4845

 D   L   E   K   L   L   M   I   A   G   E   E   R   A   L   C   L   V   D   V   1635
GAC CTG GAG AAG CTA CTC ATG ATA GCA GGA GAA GAG CGG GCA CTG TGT CTT GTG GAC GTG  4905

 K   K   V   K   Q   S   L   A   Q   S   H   L   P   A   Q   P   D   I   S   P   1655
AAG AAA GTG AAA CAG TCC CTG GCC CAG TCC CAC CTG CCT GCC CAG CCC GAC ATC TCA CCC  4965

 N   I   F   E   A   V   K   G   C   H   L   F   G   A   G   K   I   E   N   G   1675
AAC ATT TTT GAA GCT GTC AAG GGC TGC CAC TTG TTT GGG GCA GGC AAG ATT GAG AAC GGG  5025

 L   C   I   C   A   A   M   P   S   K   V   V   I   L   R   Y   N   E   N   L   1695
CTC TGC ATC TGT GCA GCC ATG CCC AGC AAA GTC GTC ATT CTC CGC TAC AAC GAA AAC CTC  5085

 S   K   Y   C   I   R   K   E   I   E   T   S   E   P   C   S   C   I   H   F   1715
AGC AAA TAC TGC ATC CGG AAA GAG ATA GAG ACC TCA GAG CCC TGC AGC TGT ATC CAC TTC  5145

 T   N   Y   S   I   L   I   G   T   N   K   F   Y   E   I   D   M   K   Q   Y   1735
ACC AAT TAC AGT ATC CTC ATT GGA ACC AAT AAA TTC TAC GAA ATC GAC ATG AAG CAG TAC  5205

 T   L   E   E   F   L   D   K   N   D   H   S   L   A   P   A   V   F   A   A   1755
ACG CTC GAG GAA TTC CTG GAT AAG AAT GAC CAT TCC TTG GCA CCT GCT GTG TTT GCC GCC  5265
```

Fig. 1K

```
 S   S   N   S   F   P   V   S   I   V   Q   V   N   S   A   G   Q   R   E   E   1775
TCT TCC AAC AGC TTC CCT GTC TCA ATC GTG CAG GTG AAC AGC GCA GGG CAG CGA GAG GAG  5325

 Y   L   L   C   F   H   E   F   G   V   F   V   D   S   Y   G   R   R   S   R   1795
TAC TTG CTG TGT TTC CAC GAA TTT GGA GTG TTC GTG GAT TCT TAC GGA AGA CGT AGC CGC  5385

 T   D   D   L   K   W   S   R   L   P   L   A   F   A   Y   R   E   P   Y   L   1815
ACA GAC GAT CTC AAG TGG AGT CGC TTA CCT TTG GCC TTT GCC TAC AGA GAA CCC TAT CTG  5445

 F   V   T   H   F   N   S   L   E   V   I   E   I   Q   A   R   S   S   A   G   1835
TTT GTG ACC CAC TTC AAC TCA CTC GAA GTA ATT GAG ATC CAG GCA CGC TCC TCA GCA GGG  5505

 T   P   A   R   A   Y   L   D   I   P   N   P   R   Y   L   G   P   A   I   S   1855
ACC CCT GCC CGA GCG TAC CTG GAC ATC CCG AAC CCG CGC TAC CTG GGC CCT GCC ATT TCC  5565

 S   G   A   I   Y   L   A   S   S   Y   Q   D   K   L   R   V   I   C   C   K   1875
TCA GGA GCG ATT TAC TTG GCG TCC TCA TAC CAG GAT AAA TTA AGG GTC ATT TGC TGC AAG  5625

 G   N   L   V   K   E   S   G   T   E   H   H   R   G   P   S   T   S   R   S   1895
GGA AAC CTC GTG AAG GAG TCC GGC ACT GAA CAC CAC CGG GGC CCG TCC ACC TCC CGC AGC  5685

 S   P   N   K   R   G   P   P   T   Y   N   E   H   I   T   K   R   V   A   S   1915
AGC CCC AAC AAG CGA GGC CCA CCC ACG TAC AAC GAG CAC ATC ACC AAG CGC GTG GCC TCC  5745
```

Fig. 1L

```
 S   P   A   P   P   E   G   P   S   H   P   R   E   P   S   T   P   H   R   Y    1935
AGC CCA GCG CCG CCC GAA GGC CCC AGC CAC CCG CGA GAG CCA AGC ACA CCC CAC CGC TAC   5805

 R   E   G   R   T   E   L   R   R   D   K   S   P   G   R   P   L   E   R   E    1955
CGC GAG GGG CGG ACC GAG CTG CGC AGG GAC AAG TCT CCT GGC CGC CCC CTG GAG CGA GAG   5865

 K   S   P   G   R   M   L   S   T   R   R   E   R   S   P   G   R   L   F   E    1975
AAG TCC CCC GGC CGG ATG CTC AGC ACG CGG AGA GAG CGG TCC CCC GGG AGG CTG TTT GAA   5925

 D   S   S   R   G   R   L   P   A   G   A   V   R   T   P   L   S   Q   V   N    1995
GAC AGC AGC AGG GGC CGG CTG CCT GCG GGA GCC GTG AGG ACC CCG CTG TCC CAG GTG AAC   5985

 K   G   R   G   Q   S   A   S   Q   V   F   T   V   N   T   V   T   Y   Y   D    2015
AAG GGA AGA GGG CAG AGT GCC TCT CAA GTT TTC ACG GTT AAC ACT GTC ACC TAT TAT GAC   6045

 W   N   K   K   L   D   N   L   P   A   N   W   S   V   L   R   I   I   Q   L    2035
TGG AAT AAA AAG CTG GAC AAC CTG CCA GCT AAC TGG TCA GTC CTG AGG ATC ATC CAG CTG   6105

 N   G   E   I   R   Q   Q   V   E   K   S   V   L   R   T   D   Y   C   *        2053
AAT GGA GAA ATC CGG CAG CAG GTT GAA AAG TCT GTT CTG AGA ACA GAT TAT TGC TGA       6162
GCAGAGTTCATGTGACTTCTAGACGTGGTGACTTAAAAAATGGCCTTAAGGCTGCAGAGCCAGCCACCTCTGCTTACAA
AAAGAGTACTTAGTGCACATGACTGTAAGAAACAATTGTAAAACCTCATCTAGAAATCAGAAAGCTTCTAATTTCTATA
GAAATGACACCTCCCTGGAGCCGAGAGACAATCTGTTGTTGATTTTGAAGGACAGGCAAGACCAACACTGTATTTAGTT
CCATAGCCAGGCCTCAACAGGGACAAGTGGCTGGCCTTAAAAACACACAGATGACTGGAAATGATGTGTGGCCTCAGTC
CCTGTTTCCCAGAATTTTACTGGCAAAGGAGTTAGCATTCATTTTTGGCTTAAGAAAAATCGAGAATGTAGGTTTAGA
```

```
           1                                                       50
   13245   MLKFKYGARN PLDAGAAEPI ASRASRLNLF FQGKPPFMTQ QQMSPLSREG
AAC72823   MLKFKYGVRN PPEASASEPI ASRASRLNLF FQGKPPLMTQ QQMSALSREG
AAC27933   .......... .......... .......... .......... ..........
  P49025   .......... .......... .......... .......... ..........
  O14578   .......... .......... .......... .......... ..........

           51                                                     100
   13245   ILDALFVLFE ECSQPALMKI KHVSNFVRKY SDTIAELQEL QPSAKDFEVR
AAC72823   MLDALFALFE ECSQPALMKM KHVSSFVQKY SDTIAELREL QPSARDFEVR
AAC27933   .......... .......... .......... .......... ..........
  P49025   .......... .......... .......... .......... ..........
  O14578   .......... .......... .......... .......... ..........

           101                                                    150
   13245   SLVGCGHFAE VQVVREKATG DIYAMKVMKK KALLAQEQVS FFEEERNILS
AAC72823   SLVGCGHFAE VQVVREKATG DVYAMKIMKK KALLAQEQVS FFEEERNILS
AAC27933   .......... .......... .......... .......... ..........
  P49025   .......... .......... .......... .......... ..........
  O14578   .......... .......... .......... .......... ..........

           151                                                    200
   13245   RSTSPWIPQL QYAFQDKNHL YLMEEYQPGG DLLSLLNRYE DQLDENLIQF
AAC72823   RSTSPWIPQL QYAFQDKNNL YLVMEYQPGG DFLSLLNRYE DQLDESMIQF
AAC27933   .......... .......... .......... .......... ..........
  P49025   .......... .......... .......... .......... ..........
  O14578   .......... .......... .......... .......... ..........
```

Fig. 3B

```
          201                                                   250
   13245  YLAELILAVH SVHLMGYVHR DIKPENILVD RTGHIKLVDF GSAAKMNSNK
AAC72823  YLAELILAVH SVHQMGYVHR DIKPENILID RTGEIKLVDF GSAAKMNSNK
AAC27933  .......... .......... .......... .......... ..........
  P49025  .......... .......... .......... .......... ..........
  O14578  .......... .......... .......... .......... ..........

          251                                                   300
   13245  MVNAKLPIGT PDYMAPEVLT VMNGDGKGTY GLDCDWWSVG VIAYEMIYGR
AAC72823  .VDAKLPIGT PDYMAPEVLT VMNEDRRGTY GLDCDWWSVG VVAYEMVYGK
AAC27933  .......... .......... .......... .......... ..........
  P49025  .......... .......... .......... .......... ..........
  O14578  .......... .......... .......... .......... ..........

          301                                                   350
   13245  SPFAEGTSAR TFNNIMNFQR FLKFPDDPKV SSDFLDLIQS LLCGQKERLK
AAC72823  TPFTEGTSAR TFNNIMNFQR FLKFPDDPKV SSELLDLLQS LLCVQKERLK
AAC27933  .......... .......... .......... .......... ..........
  P49025  .......... .......... .......... .......... ..........
  O14578  .......... .......... .......... .......... ..........

          351                                                   400
   13245  FEGLCCHPFF SKIDWNNIRN SPPPFVPTLK SDDDTSNFDE PEKNSWVSSS
AAC72823  FEGLCCHPFF ARTDWNNIRN SPPPFVPTLK SDDDTSNFDE PEKNSWAFIL
AAC27933  .......... .......... ...PFVPTLK SDDDTSNFDE PEKNSWVSSS
  P49025  .......... .......... .......... .......... ..........
  O14578  .......... .......... .......... .......... ..........
```

Fig. 3C

```
          401                                                   450
   13245  PCQLSPSGFS GEELPFVGFS YSKALGILGR SESVVSGLDS PAKTSSMEKK
AAC72823  CVPAEPLAFS GEELPFVGFS YSKALGYLGR SESVVSSLDS PAKVSSMEKK
AAC27933  VCQLSPSGFS GEELPFVGFS YSKALGYLGR SESVVSSLDS PAKVSSMEKK
  P49025  .......... .......... .......... .......... ..........
  O14578  .......... .......... .......... .......... ..........

          451                                                   500
   13245  LLIKSKELQD SQDKCHKMEQ EMTRLHRRVS EVEAVLSQKE VELKASETQR
AAC72823  LLIKSKELQD SQDKCHKMEQ EMTRLHRRVS EVEAVLSQKE VELKASETQR
AAC27933  LLIKSKELQD SQDKCHKMEQ EMTRLHRRVS EVEAVLSQKE VELKASETQR
  P49025  .........M LLGEEAMMEQ EMTRLHRRVS EVEAVLSQKE VELKASETQR
  O14578  .......... .......... .......... .......... ..........

          501                                                   550
   13245  SLLEQDLATY ITECSSLKRS LEQARMEVSQ EDDKALQLLH DIREQSRKLQ
AAC72823  SLLEQDLATY ITECSSLKRS LEQARMEVSQ EDDKALQLLH DIREQSRKLQ
AAC27933  SLLEQDLATY ITECSSLKRS LEQARMEVSQ EDDKALQLLH DIREQSRKLQ
  P49025  SLLEQDLATY ITECSSLKRS LEQARMEVSQ EDDKALQLLH DIREQSRKLQ
  O14578  .......... .......... .......... .......... ..........

          551                                                   600
   13245  EIKEQEYQAQ VEEMRLMMNQ LEEDLVSARR RSDLYESELR ESRLAAEEFK
AAC72823  EIKEQEYQAQ VEEMRLMMNQ LEEDLVSARR RSDLYESELR ESRLAAEEFK
AAC27933  EIKEQEYQAQ VEEMRLMMNQ LEEDLVSARR RSDLYESELR ESRLAAEEFK
  P49025  EIKEQEYQAQ VEEMRLMMNQ LEEDLVSARR RSDLYESELR ESRLAAEEFK
  O14578  .......... .......... .......... .......... ..........
```

Fig. 3D

```
          601                                                650
   13245  RKATECQHKL LKAKDQGKPE VGEYAKLEKI NAEQQLKIQE LQEKLEKA..
AAC72823  RKANECQHKL MKAKDQGKPE VGEYSKLEKI NAEQQLKIQE LQEKLEKAVK
AAC27933  RKANECQHKL MKAKDQGKPE VGEYSKLEKI NAEQQLKIQE LQEKLEKAVK
  P49025  RKANECQHKL MKAKDQGKPE VGEYSKLEKI NAEQQLKIQE LQEKLEKAVK
  O14578  .......... .......... .......... .......... ..........

          651                                                700
   13245  .......... ....AKERAE RELEKLQNRE DSSEGIRKKL VEAEERRHSL
AAC72823  ASTEATELLQ NIRQAKERAE RELEKLHNRE DSSEGIKKKL VEAEERRHSL
AAC27933  ASTEATELLQ NIRQAKERAE RELEKLHNRE DSSEGIKKKL VEAEE.....
  P49025  ASTEATELLQ NIRQAKERAE RELEKLHNRE DSSEGIKKKL VEAEERRHSL
  O14578  .......... .......... .......... .......... ..........

          701                                                750
   13245  ENKVKRLETM ERRENRLKDD IQTKSQQIQQ MADKILELEE KHREAQVSAQ
AAC72823  ENKVKRLETM ERRENRLKDD IQTKSEQIQQ MADKILELEE KHREAQVSAQ
AAC27933  .......... .......... .......... .......LEE KHREAQVSAQ
  P49025  ENKVKRLETM ERRENRLKDD IQTKSEQIQQ MADKILELEE KHREAQVSAQ
  O14578  .......... .......... .......... .......... ..........

          751                                                800
   13245  HLEVHLKQKE QHYEEKIKVL DNQIKKDLAD KETLENMMQR HEEEAHEKGK
AAC72823  HLEVHLKQKE QHYEEKIKVL DNQIKKDLAD KESLENMMQR HEEEAHEKGK
AAC27933  HLEVHLKQKE QHYEEKIKVL DNQIKKDLAD KESLENMMQR HEEEAHEKGK
  P49025  HLEVHLKQKE QHYEEKIKVL DNQIKKDLAD KESLENMMQR HEEEAHEKGK
  O14578  .......... ........VL DNQIKKDLAD KETLENMMQR HEEEAHEKGK
```

Fig. 3E

```
          801                                                850
   13245  ILSEQKAMIN AMDSKIRSLE QRIVELSEAN KLAANSSLFT QRNMKAQEEM
AAC72823  ILSEQKAMIN AMDSKIRSLE QRIVELSEAN KLAANSSLFT QRNMKAQEEM
AAC27933  ILSEQKAMIN AMDSKIRSLE QRIVELSEAN KLAANSSLFT QRNMKAQEEM
  P49025  ILSEQKAMIN AMDSKIRSLE QRIVELSEAN KLAANSSLFT QRNMKAQEEM
  O14578  ILSEQKAMIN AMDSKIRSLE QRIVELSEAN KLAANSSLFT QRNMKAQEEM

          851                                                900
   13245  ISELRQQKFY LETQAGKLEA QNRKLEEQLE KISHQDHSDK NRLLELETRL
AAC72823  ISELRQQKFY LETQAGKLEA QNRKLEEQLE KISHQDHSDK SRLLELETRL
AAC27933  ISELRQQKFY LETQAGKLEA QNRKLEEQLE KISHQDHSDK SRLLELETRL
  P49025  ISELRQQKFY LETQAGKLEA QNRKLEEQLE KISHQDHSDK SRLLELETRL
  O14578  ISELRQQKFY LETQAGKLEA QNRKLEEQLE KISHQDHSDK NRLLELETRL

          901                                                950
   13245  REVSLEHEEQ KLELKRQLTE LQLSLQERES QLTALQAARA ALESQLRQAK
AAC72823  REVSLEHEEQ KLELKRQLTE LQLSLQERES QLTALQAARA ALESQLRQAK
AAC27933  REVSLEHEEQ KLELKRQLTE LQLSLQERES QLTALQAARA ALESQLRQAK
  P49025  REVSLEHEEQ KLELKRQLTE LQLSLQERES QLTALQAARA ALESQLRQAK
  O14578  REVSLEHEEQ KLELKRQLTE LQLSLQERES QLTALQAARA ALESQLRQAK

          951                                               1000
   13245  TELEETTAEA EEEIQALTAH RDEIQRKFDA LRNSCTVITD LEEQLNQLTE
AAC72823  TELEETTAEA EEEIQALTAH RDEIQRKFDA LRNSCTVITD LEEQLNQLTE
AAC27933  TELEETTAEA EEEIQALTAH RDEIQRKFDA LRNSCTVITD LEEQLNQLTE
  P49025  TELEETTAEA EEEIQALTAH RDEIQRKFDA LRNSCTVITD LEEQLNQLTE
  O14578  TELEETTAEA EEEIQALTAH RDEIQRKFDA LRNSCTVITD LEEQLNQLTE
```

Fig. 3F

```
             1001                                                  1050
   13245     DNAELNNQNF YLSKQLDEAS GANDEIVQLR SEVDHLRREI TEREMQLTSQ
AAC72823     DNAELNNQNF YLSKQLDEAS GANDEIVQLR SEVDHLRREI TEREMQLTSQ
AAC27933     DNAELNNQNF YLSKQLDEAS GANDEIVQLR SEVDHLRREI TEREMQLTSQ
  P49025     DNAELNNQNF YLSKQLDEAS GANDEIVQLR SEVDHLRREI TEREMQLTSQ
  O14578     DNAELNNQNF YLSKQLDEAS GANDEIVQLR SEVDHLRREI TEREMQLTSQ

             1051                                                  1100
   13245     KQTMEALKTT CTMLEEQVMD LEALNDELLE KERQWEAWRS VLGDEKSQFE
AAC72823     KQTMEALKTT CTMLEEQVLD LEALNDELLE KERQWEAWRS VLGDEKSQFE
AAC27933     KQTMEALKTT CTMLEEQVLD LEALNDELLE KERQWEAWRS VLGDEKSQFE
  P49025     KQTMEALKTT CTMLEEQVLD LEALNDELLE KERQWEAWRS VLGDEKSQFE
  O14578     KQTMEALKTT CTMLEEQVMD LEALNDELLE KERQWEAWRS VLGDEKSQFE

             1101                                                  1150
   13245     CRVRELQRML DTEKQSRARA DQRITESRQV VELAVKEHKA EILALQQALK
AAC72823     CRVRELQRML DTEKQSRARA DQRITESRQV VELAVKEHKA EILALQQALK
AAC27933     CRVRELQRML DTEKQSRARA DQRITESRQV VELAVKEHKA EILALQQALK
  P49025     CRVRELQRML DTEKQSRARA DQRITESRQV VELAVKEHKA EILALQQALK
  O14578     CRVRELQRML DTEKQSRARA DQRITESRQV VELAVKEHKA EILALQQALK

             1151                                                  1200
   13245     EQKLKAESLS DKLNDLEKKH AMLEMNARSL QQKLETEREL KQRLLEEQAK
AAC72823     EQKLKAESLS DKLNDLEKKH AMLEMNARSL QQKLETEREL KQRLLEEQAK
AAC27933     EQKLKAESLS DKLNDLEKKH AMLEMNARSL QQKLETEREL KQRLLEEQAK
  P49025     EQKLKAESLS DKLNDLEKKH AMLEMNARSL QQKLETEREL KQRLLEEQAK
  O14578     EQKLKAESLS DKLNDLEKKH AMLEMNARSL QQKLETEREL KQRLLEEQAK
```

Fig. 3G

```
          1201                                                  1250
   13245  LQQQMDLQKN HIFRLTQGLQ EALDRADLLK TERSDLEYQL ENIQVLYSHE
AAC72823  LQQQMDLQKN HIFRLTQGLQ EALDRADLLK TERSDLEYQL ENIQVLYSHE
AAC27933  LQQQMDLQKN HIFRLTQGLQ EALDRADLLK TERSDLEYQL ENIQVLYSHE
  P49025  LQQQMDLQKN HIFRLTQGLQ EALDRADLLK TERSDLEYQL ENIQVLYSHE
  O14578  LQQQMDLQKN HIFRLTQGLQ EALDRADLLK TERSDLEYQL ENIQVLYSHE

          1251                                                  1300
   13245  KVKMEGTISQ QTKLIDFLQA KMDQPAKKKK GLFSRRKEDP ALPTQVPLQY
AAC72823  KVKMEGTISQ QTKLIDFLQA KMDQPAKKKK .......... .....VPLQY
AAC27933  KVKMEGTISQ QTKLIDFLQA KMDQPAKKKK .......... .....VPLQY
  P49025  KVKMEGTISQ QTKLIDFLQA KMDQPAKKKK .......... .....VPLQY
  O14578  KVKMEGTISQ QTKLIDFLQA KMDQPAKKKK .......... .....VPLQY

          1301                                                  1350
   13245  NELKLALEKE KARCAELEEA LQKTRIELRS AREEAAHRKA TDHPHPSTPA
AAC72823  NELKLALEKE KARCAELEEA LQKTRIELRS AREEAAHRKA TDHPHPSTPA
AAC27933  NELKLALEKE KARCAELEEA LQKTRIELRS AREEAAHRKA TDHPHPSTPA
  P49025  NELKLALEKE KARCAELEEA LQKTRIELRS AREEAAHRKA TDHPHPSTPA
  O14578  NELKLALEKE KARCAELEEA LQKTRIELRS AREEAAHRKA TDHPHPSTPA

          1351                                                  1400
   13245  TARQQIAMSA IVRSPEHQPS AMSLLAPPSS RRKESSTPEE FSRRLKERMH
AAC72823  TARQQIAMSA IVRSPEHQPS AMSLLAPPSS RRKESSTPEE FSRRLKERMH
AAC27933  TARQQIAMSA IVRSPEHQPS AMSLLAPPSS RRKESSTPEE FSRRLKERMH
  P49025  TARQQIAMSA IVRSPEHQPS AMSLLAPPSS RRKESSTPEE FSRRLKERMH
  O14578  TARQQIAMSA IVRSPEHQPS AMSLLAPPSS RRKESSTPEE FSRRLKERMH
```

Fig. 3H

```
             1401                                                   1450
    13245    HNIPHRFNVG LNMRATKCAV CLDTVHFGRQ ASKCLECQVM CHPKCSTCLP
 AAC72823    HNIPHRFNVG LNMRATKCAV CLDTVHFGRQ ASKCLECQVM CHPKCSTCLP
 AAC27933    HNIPHRFNVG LNMRATKCAV CLDTVHFGRQ ASKCLECQVM CHPKCSTCLP
   P49025    HNIPHRFNVG LNMRATKCAV CLDTVHFGRQ ASKCLECQVM CHPKCSTCLP
   O14578    HNIPHRFNVG LNMRATKCAV CLDTVHFGRQ ASKCLECQVM CHPKCSTCLP

             1451                                                   1500
    13245    ATCGLPAEYA THFTEAFCRD KMNSPGLQTK EPSSSLHLEG WMKVPRNNKR
 AAC72823    ATCGLPAEYA THFTEAFCRD KMNSPGLQSK EPGSSLHLEG WMKVPRNNKR
 AAC27933    ATCGLPAEYA THFTEAFCRD KMNSPGLQSK EPGSSLHLEG WMKVPRNNKR
   P49025    ATCGLPAEYA THFTEAFCRD KMNSPGLQSK EPGSSLHLEG WMKVPRNNKR
   O14578    ATCGLPAEYA THFTEAFCRD KMNSPGLQTK EPSSSLHLEG WMKVPRNNKR

             1501                                                   1550
    13245    GQQGWDRKYI VLEGSKVLIY DNEAREAGQR PVEEFELCLP DGDVSIHGAV
 AAC72823    GQQGWDRKYI VLEGSKVLIY DNEAREAGQR PVEEFELCLP DGDVSIHGAV
 AAC27933    GQQGWDRKYI VLEGSKVLIY DNEAREAGQR PVEEFELCLP DGDVSIHGAV
   P49025    GQQGWDRKYI VLEGSKVLIY DNEAREAGQR PVEEFELCLP DGDVSIHGAV
   O14578    GQQGWDRKYI VLEGSKVLIY DNEAREAGQR PVEEFELCLP DGDVSIHGAV

             1551                                                   1600
    13245    GASELANTAK A......... .......... .......... ..........
 AAC72823    GASELANTAK ADVPYILKME SHPHTTCWPG RTLYLLAPSF PDKQRWVTAL
 AAC27933    GASELANTAK ADVPYILKME SHPHTTCWPG RTLYLLAPSF PDKQRWVTAL
   P49025    GASELANTAK ADVPYILKME SHPHTTCWPG RTLYLLAPSF PDKQRWVTAL
   O14578    GASELANTAK ADVPYILKME SHPHTTCWPG RTLYLLAPSF PDKQRWVTAL
```

Fig. 3I

```
            1601                                                   1650
   13245    .......... .EKAEADAKL LGNSLLKLEG DDRLDMNCTL PFSDQVVLVG
AAC72823    ESVVAGGRVS REKAEADAKL LGNSLLKLEG DDRLDMNCTL PFSDQVVLVG
AAC27933    ESVVAGGRVS REKAEADAKL LGNSLLKLEG DDRLDMNCTL PFSDQVVLVG
  P49025    ESVVAGGRVS REKAEADAKL LGNSLLKLEG DDRLDMNCTL PFSDQVVLVG
  O14578    ESVVAGGRVS REKAEADAKL LGNSLLKLEG DDRLDMNCTL PFSDQVVLVG

            1651                                                   1700
   13245    TEEGLYALNV LKNSLTHVPG IGAVFQIYII KDLEKLLMIA GEERALCLVD
AAC72823    TEEGLYALNV LKNSLTHIPG IGAVFQIYII KDLEKLLMIA GEERALCLVD
AAC27933    TEEGLYALNV LKNSLTHIPG IGAVFQIYII KDLEKLLMIA GEERALCLVD
  P49025    TEEGLYALNV LKNSLTHIPG IGAVFQIYII KDLEKLLMIA GEERALCLVD
  O14578    TEEGLYALNV LKNSLTHVPG IGAVFQIYII KDLEKLLMIA GEERALCLVD

            1701                                                   1750
   13245    VKKVKQSLAQ SHLPAQPDIS PNIFEAVKGC HLFGAGKIEN GLCICAAMPS
AAC72823    VKKVKQSLAQ SHLPAQPDVS PNIFEAVKGC HLFAAGKIEN SLCICAAMPS
AAC27933    VKKVKQSLAQ SHLPAQPDVS PNIFEAVKGC HLFAAGKIEN SLCICAAMPS
  P49025    VKKVKQSLAQ SHLPAQPDVS PNIFEAVKGC HLFAAGKIEN SLCICAAMPS
  O14578    VKKVKQSLAQ SHLPAQPDIS PNIFEAVKGC HLFGAGKIEN GLCICAAMPS

            1751                                                   1800
   13245    KVVILRYNEN LSKYCIRKEI ETSEPCSCIH FTNYSILIGT NKFYEIDMKQ
AAC72823    KVVILRYNDN LSKYCIRKEI ETSEPCSCIH FTNYSILIGT NKFYEIDMKQ
AAC27933    KVVILRYNDN LSKYCIRKEI ETSEPCSCIH FTNYSILIGT NKFYEIDMKQ
  P49025    KVVILRYNDN LSKYCIRKEI ETSEPCSCIH FTNYSILIGT NKFYEIDMKQ
  O14578    KVVILRYNEN LSKYCIRKEI ETSEPCSCIH FTNYSILIGT NKFYEIDMKQ
```

Fig. 3J

```
          1801                                                  1850
   13245  YTLEEFLDKN DHSLAPAVFA ASSNSFPVSI VQVNSAGQRE EYLLCFHEFG
AAC72823  YTLDEFLDKN DHSLAPAVFA SSSNSFPVSI VQANSAGQRE EYLLCFHEFG
AAC27933  YTLDEFLDKN DHSLAPAVFA SSSNSFPVSI VQANSAGQRE EYLLCFHEFG
  P49025  YTLDEFLDKN DHSLAPAVFA SSSNSFPVSI VQANSAGQRE EYLLCFHEFG
  O14578  YTLEEFLDKN DHSLAPAVFA ASSNSFPVSI VQVNSAGQRE EYLLCFHEFG

          1851                                                  1900
   13245  VFVDSYGRRS RTDDLKWSRL PLAFAYREPY LFVTHFNSLE VIEIQARSSA
AAC72823  VFVDSYGRRS RTDDLKWSRL PLAFAYREPY LFVTHFNSLE VIEIQARSSL
AAC27933  VFVDSYGRRS RTDDLKWSRL PLAFAYREPY LFVTHFNSLE VIEIQARSSL
  P49025  VFVDSYGRRS RTDDLKWSRL PLAFAYREPY LFVTHFNSLE VIEIQARSSL
  O14578  VFVDSYGRRS RTDDLKWSRL PLAFAYREPY LFVTHFNSLE VIEIQARSSA

          1901                                                  1950
   13245  GTPARAYLDI PNPRYLGPAI SSGAIYLASS YQDKLRVICC KGNLVKESGT
AAC72823  GSPARAYLEI PNPRYLGPAI SSGAIYLASS YQDKLRVICC KGNLVKESGT
AAC27933  GSPARAYLEI PNPRYLGPAI SSGAIYLASS YQDKLRVICC KGNLVKESGT
  P49025  GSPARAYLEI PNPRYLGPAI SSGAIYLASS YQDKLRVICC KGNLVKESGT
  O14578  GTPARAYLDI PNPRYLGPAI SSGAIYLASS YQDKLRVICC KGNLVKESGT

          1951                                                  2000
   13245  EHHRGPSTSR SSPNKRGPPT YNEHITKRVA SSPAPPEGPS HPREPSTPHR
AAC72823  EQHRVPSTSR SSPNKRGPPT YNEHITKRVA SSPAPPEGPS HPREPSTPHR
AAC27933  EQHRVPSTSR SSPNKRGPPT YNEHITKRVA SSPAPPEGPS HPREPSTPHR
  P49025  EQHRVPSTSR SSPNKRGPPT YNEHITKRVA SSPAPPEGPS HPREPSTPHR
  O14578  EHHRGPSTSR SSPNKRGPPT YNEHITKRVA SSPAPPEGPS HPREPSTPHR
```

Fig. 3K

```
           2001                                                       2050
    13245  YR..EGRTEL RRDKSPGRPL EREKSPGRML STRRERSPGR LFEDSSRGRL
 AAC72823  YRDREGRTEL RRDKSPGRPL EREKSPGRML STRRERSPGR LFEDSSRGRL
 AAC27933  YRDREGRTEL RRDKSPGRPL EREKSPGRML STRRERSPGR LFEDSSRGRL
   P49025  YRDREGRTEL RRDKSPGRPL EREKSPGRML STRRERSPGR LFEDSSRGRL
   O14578  YR..EGRTEL RRDKSPGRPL EREKSPGRML STRRERSPGR LFEDSSRGRL

           2051                                                       2100
    13245  PAGAVRTPLS QVNKGRGQSA SQVFTVNTVT YYDWNKKLDN LPANWSVLRI
 AAC72823  PAGAVRTPLS QVNKVWDQSS V......... .......... ..........
 AAC27933  PAGAVRTPLS QVNKVWDQSS V......... .......... ..........
   P49025  PAGAVRTPLS QVNKVWDQSS V......... .......... ..........
   O14578  PAGAVRTPLS QVNKVWDQSS V......... .......... ..........

           2101                  2121
    13245  IQLNGEIRQQ VEKSVLRTDY C
 AAC72823  .......... .......... .
 AAC27933  .......... .......... .
   P49025  .......... .......... .
   O14578  .......... .......... .
```

13245, A NOVEL HUMAN MYOTONIC DYSTROPHY TYPE PROTEIN KINASE AND USES THEREFOR

CROSS-REFERENCE TO RELATED APPLICATIONS

This application is entitled to priority pursuant to 35 U.S.C. § 119(e) to U.S. provisional patent application 60/242,429 which was filed on Oct. 23, 2000.

STATEMENT REGARDING FEDERALLY SPONSORED RESEARCH OR DEVELOPMENT

Not Applicable

REFERENCE TO MICROFICHE APPENDIX

Not Applicable

BACKGROUND OF THE INVENTION

Protein phosphorylation, for example at serine, threonine, and tyrosine residues, is a key regulatory mechanism for a variety of cellular processes. Protein phosphorylation is influenced primarily by enzymes of two types, namely protein kinases (PKs) and protein phosphatases (PPs). PKs catalyze addition of a phosphate moiety to a protein amino acid residue (generally a serine, threonine, or tyrosine residue), and PPs catalyze removal of such moieties. The catalytic activities of PKs and PPs are, in turn, influenced by the state of the cell and the environment in which it finds itself.

Myotonic dystrophy type PKs (MDPKs) are associated with modulation of cell morphology, shape, and contractility. MDPKs are also known to modulate the activity of skeletal muscle voltage-gated sodium channels, but not cardiac muscle voltage-gated sodium channels. MDPKs thus have a role in a variety of musculodegenerative and other musculoskeletal disorders including, for example, muscular dystrophy (MD) of various types (e.g., Duchenne's MD, limb-girdle MD, Becker MD, facioscapulohumerol MD, mitochondrial myopathy, and congenital myopathy) and myotonic dystrophies (e.g., Steinert's disease and Thomsen's disease).

Numerous MDPKs have been described, and many more are believed to exist. In view of the widespread and critical nature of MDPK activities in normal and pathological physiological processes, a need exists for identification of further members of this protein family. The present invention satisfies this need by providing a novel human MDPK.

SUMMARY OF THE INVENTION

The present invention is based, in part, on the discovery of a novel gene encoding a MDPK, the gene being referred to herein as "13245". The nucleotide sequence of a cDNA encoding 13245 is shown in SEQ ID NO: 1, and the amino acid sequence of a 13245 polypeptide is shown in SEQ ID NO: 2. In addition, the nucleotide sequence of the coding region is depicted in SEQ ID NO: 3.

Accordingly, in one aspect, the invention features a nucleic acid molecule that encodes a 13245 protein or polypeptide, e.g., a biologically active portion of the 13245 protein. In a preferred embodiment the isolated nucleic acid molecule encodes a polypeptide having the amino acid sequence SEQ ID NO: 2. In other embodiments, the invention provides isolated 13245 nucleic acid molecules having the nucleotide sequence of either of SEQ ID NOs: 1 and 3.

In still other embodiments, the invention provides nucleic acid molecules that have sequences that are substantially identical (e.g., naturally occurring allelic variants) to the nucleotide sequence of either of SEQ ID NOs: 1 and 3. In other embodiments, the invention provides a nucleic acid molecule which hybridizes under stringent hybridization conditions with a nucleic acid molecule having a sequence comprising the nucleotide sequence of either of SEQ ID NOs: 1 and 3, wherein the nucleic acid encodes a full length 13245 protein or an active fragment thereof.

In a related aspect, the invention further provides nucleic acid constructs that include a 13245 nucleic acid molecule described herein. In certain embodiments, the nucleic acid molecules of the invention are operatively linked to native or heterologous regulatory sequences. Also included are vectors and host cells containing the 13245 nucleic acid molecules of the invention, e.g., vectors and host cells suitable for producing 13245 nucleic acid molecules and polypeptides.

In another related aspect, the invention provides nucleic acid fragments suitable as primers or hybridization probes for detection of 13245-encoding nucleic acids.

In still another related aspect, isolated nucleic acid molecules that are antisense to a 13245-encoding nucleic acid molecule are provided.

In another aspect, the invention features 13245 polypeptides, and biologically active or antigenic fragments thereof that are useful, e.g., as reagents or targets in assays applicable to treatment and diagnosis of 13245-mediated or related disorders (e.g., MDPK-mediated disorders such as those described herein). In another embodiment, the invention provides 13245 polypeptides having protein kinase activity. Preferred polypeptides are 13245 proteins including at least one pkinase domain, and preferably having a 13245 activity, e.g., a 13245 activity as described herein. Preferred polypeptides are 13245 proteins including at least one CNH domain and at least one pkinase domain. Other preferred polypeptides are 13245 proteins including at least one CNH domain, at least one pkinase domain, at least one phorbol ester/diacylglycerol binding domain, at least one PH domain, and at least one leucine zipper domain.

In other embodiments, the invention provides 13245 polypeptides, e.g., a 13245 polypeptide having the amino acid sequence shown in SEQ ID NO: 2, an amino acid sequence that is substantially identical to the amino acid sequence shown in SEQ ID NO: 2, or an amino acid sequence encoded by a nucleic acid molecule having a nucleotide sequence which hybridizes under stringent hybridization conditions to a nucleic acid molecule comprising the nucleotide sequence of either of SEQ ID NOs: 1 and 3, wherein the nucleic acid encodes a full length 13245 protein or an active fragment thereof.

In a related aspect, the invention further provides nucleic acid constructs that include a 13245 nucleic acid molecule described herein.

In a related aspect, the invention provides 13245 polypeptides or fragments operatively linked to non-13245 polypeptides to form fusion proteins.

In another aspect, the invention features antibodies and antigen-binding fragments thereof, that react with, or more preferably, specifically bind, 13245 polypeptides.

In another aspect, the invention provides methods of screening for compounds that modulate the expression or activity of the 13245 polypeptides or nucleic acids.

In still another aspect, the invention provides a process for modulating 13245 polypeptide or nucleic acid expression or activity, e.g., using the screened compounds. In certain embodiments, the methods involve treatment of conditions related to aberrant activity or expression of the 13245 polypeptides or nucleic acids, such as conditions involving aberrant or deficient protein phosphorylation or aberrant or deficient cell process regulation (e.g., aberrant or deficient cell signaling or aberrant or deficient muscular function).

The invention also provides assays for determining the activity of or the presence or absence of 13245 polypeptides or nucleic acid molecules in a biological sample, including for disease diagnosis.

In further aspect the invention provides assays for determining the presence or absence of a genetic alteration in a 13245 polypeptide or nucleic acid molecule, including for disease diagnosis.

The invention also includes a method of modulating the ability of a cell to catalyze interconversion of the phosphorylated and de-phosphorylated forms a GTPase protein. The method comprises modulating 13245 protein activity in the cell. The activity of 13245 protein can be modulated by inhibiting expression of the 13245 gene in the cell, for example by administering to the cell an antisense oligonucleotide which hybridizes under stringent conditions with a transcript (e.g., an mRNA) of the 13245 gene, an antisense oligonucleotide which hybridizes under stringent conditions with a polynucleotide having the nucleotide sequence SEQ ID NO: 1, or an antisense oligonucleotide which hybridizes under stringent conditions with a polynucleotide having the nucleotide sequence SEQ ID NO: 3. Alternatively the activity of 13245 protein can be inhibited without significantly affecting 13245 gene expression in the cell. For example, the activity of 13245 protein can be inhibited by administering to the cell an agent which inhibits an activity of 13245 protein, such as an antibody which specifically binds with 13245 protein. In a related aspect, the activity of 13245 can be modulated by enhancing expression of 13245 in the cell. For example, expression of 13245 in a cell can be enhanced by administering to the cell an agent that enhances expression of 13245, such as an expression vector encoding 13245 protein.

The invention further includes a method for assessing whether a test compound is useful for modulating at least one phenomenon selected from the group consisting of (1) interconversion of the phosphorylated and de-phosphorylated forms of a serine, threonine, or tyrosine residue of a GTPase protein; (2) cell contractility; (3) cell growth; (4) cell conductivity; (5) entry of a cell into the cell cycle; (6) progression of a cell through the cell cycle; (7) mitogenesis; (8) cell metabolism; (9) gene transcription; (11) cytokinesis; (12) cell shape; (13) cell movement; (14) integration of a viral genome into a host cell genome; (15) maintenance of a viral genome within a host cell genome; (16) a cytological change in a virus-infected host cell; (17) virus production in a virus-infected host cell; (18) interaction of a virion with a membrane of a virus-infected host cell; and (19) encapsulation of a virion within a portion of a membrane of a virus-infected host cell. The method comprises:

a) adding the test compound to a first composition comprising a polypeptide that has an amino acid sequence at least 90% identical to SEQ ID NO: 2 and that exhibits a 13245 activity; and b) comparing the 13245 activity in the first composition and in a second composition that is substantially identical to the first composition except that it does not comprise the test compound.

A difference in the 13245 activity in the first and second compositions is an indication that the test compound is useful for modulating the phenomenon.

The invention also includes another method for assessing whether a test compound is useful for modulating at least one phenomenon selected from the group consisting of (1) interconversion of the phosphorylated and de-phosphorylated forms of a serine, threonine, or tyrosine residue of a GTPase protein; (2) cell contractility; (3) cell growth; (4) cell conductivity; (5) entry of a cell into the cell cycle; (6) progression of a cell through the cell cycle; (7) mitogenesis; (8) cell metabolism; (9) gene transcription; (11) cytokinesis; (12) cell shape; (13) cell movement; (14) integration of a viral genome into a host cell genome; (15) maintenance of a viral genome within a host cell genome; (16) a cytological change in a virus-infected host cell; (17) virus production in a virus-infected host cell; (18) interaction of a virion with a membrane of a virus-infected host cell; and (19) encapsulation of a virion within a portion of a membrane of a virus-infected host cell. This method comprises:

a) adding the test compound to a first composition comprising a cell which comprises a nucleic acid that encodes a polypeptide that has an amino acid sequence at least 90% identical to SEQ ID NO: 2 and that exhibits a 13245 activity; and b) comparing 13245 activity in the first composition and in a second composition that is substantially identical to the first composition except that it does not comprise the test compound.

A difference in the 13245 activity in the first and second compositions is an indication that the test compound is useful for modulating the phenomenon.

Compounds identified using these methods can be used to make a pharmaceutical composition for modulating the phenomenon, for example by combining it with a pharmaceutically acceptable carrier. Such compositions can be used to modulate the phenomenon in a human.

The invention includes another method for identifying a compound useful for modulating at least one phenomenon selected from the group consisting of (1) interconversion of the phosphorylated and de-phosphorylated forms of a serine, threonine, or tyrosine residue of a GTPase protein; (2) cell contractility; (3) cell growth; (4) cell conductivity; (5) entry of a cell into the cell cycle; (6) progression of a cell through the cell cycle; (7) mitogenesis; (8) cell metabolism; (9) gene transcription; (11) cytokinesis; (12) cell shape; (13) cell movement; (14) integration of a viral genome into a host cell genome; (15) maintenance of a viral genome within a host cell genome; (16) a cytological change in a virus-infected host cell; (17) virus production in a virus-infected host cell; (18) interaction of a virion with a membrane of a virus-infected host cell; and (19) encapsulation of a virion within a portion of a membrane of a virus-infected host cell. This method comprises:

a) contacting the test compound and a polypeptide selected from the group consisting of i) a polypeptide which is encoded by a nucleic acid molecule comprising a portion having a nucleotide sequence which is at least 90% identical to one of SEQ ID NOs: 1 and 3; and ii) a fragment of a polypeptide having either an amino acid sequence comprising SEQ ID NO: 2, wherein the fragment comprises at least 25 contiguous amino acid residues of SEQ ID NO: 2 or a cell that expresses the polypeptide; and b) determining whether the polypeptide binds with the test compound.

Binding of the polypeptide and the test compound is an indication that the test compound is useful for modulating the phenomenon.

Other features and advantages of the invention will be apparent from the following detailed description, and from the claims.

BRIEF DESCRIPTION OF THE DRAWINGS

FIGS. 1A–1M depict a cDNA sequence (SEQ ID NO: 1) and predicted amino acid sequence (SEQ ID NO: 2) of human 13245. The methionine-initiated open reading frame of human 13245 (without the 5'- and 3'-non-translated regions) starts at nucleotide 19 of SEQ ID NO: 1, and the coding region (not including the terminator codon; shown in SEQ ID NO: 3) extends through nucleotide 6178 of SEQ ID NO: 1.

FIGS. 3A–3K display alignment of the amino acid sequence (SEQ ID NO: 2) of 13245, murine rho/rac-interacting citron kinase (“AAC72823”; GENBANK® accession no. AAC72823; SEQ ID NO: 4), murine citron-K kinase (“AAC27933”; GENBANK® accession no. AAC27933; SEQ ID NO: 5), murine citron protein (“P49025”; GENBANK® accession no. P49025; SEQ ID NO: 6), and human citron protein (“O14578”; GENBANK® accession no. O14578; SEQ ID NO: 7). The alignment was made using the Multalin v4ersion 5.4.1 software using the blosum62 symbol comparison table, a gap weight of 12, and a gap length weight of 2.

DETAILED DESCRIPTION

Figure 2:
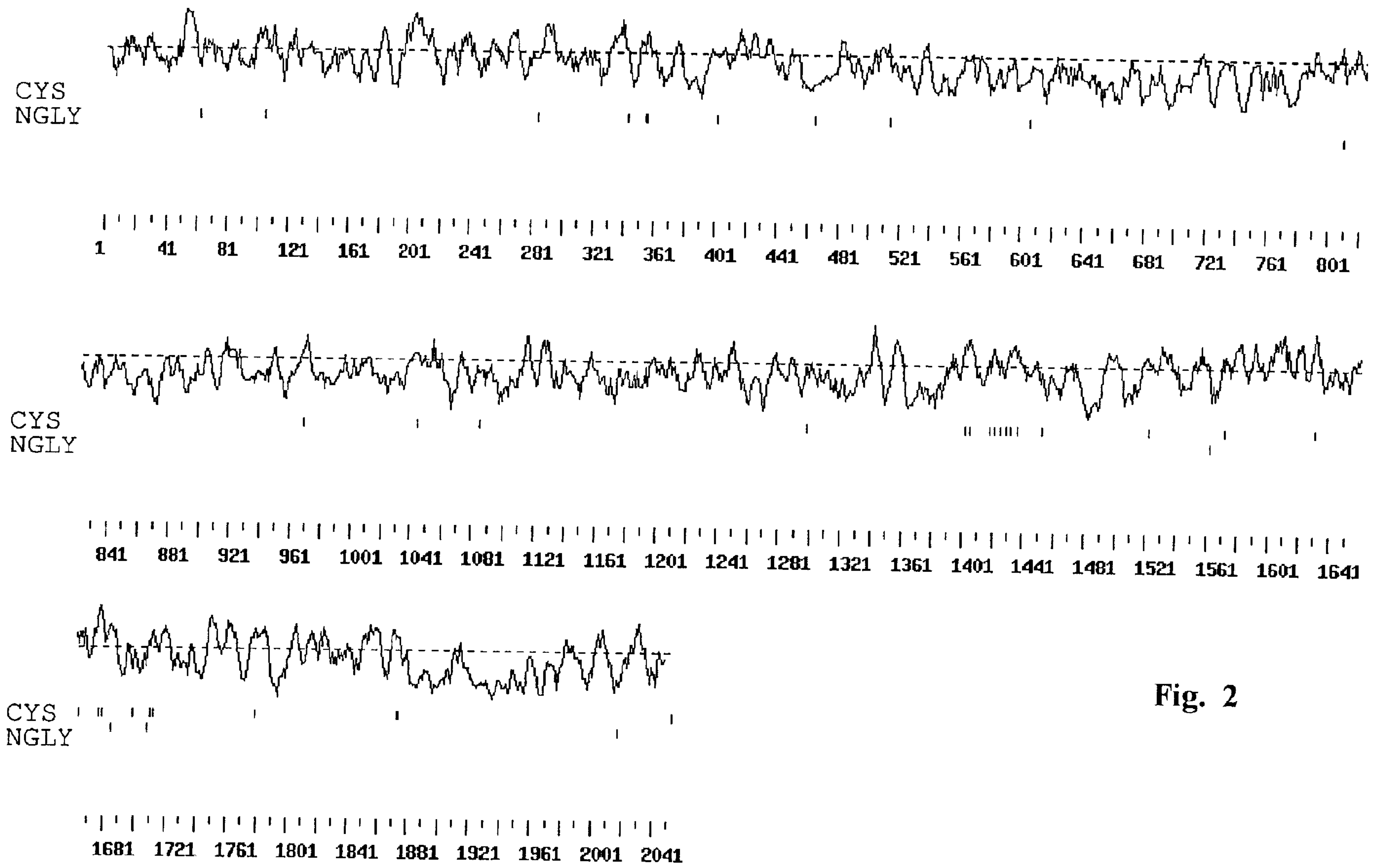
FIG. 2 depicts a hydropathy plot of human 13245. Relatively hydrophobic residues are shown above the dashed horizontal line, and relative hydrophilic residues are below the dashed horizontal line. The cysteine residues (cys) are indicated by short vertical lines below the hydropathy trace. The numbers corresponding to the amino acid sequence of human 13245 are indicated. Polypeptides of the invention include fragments which include: all or part of a hydrophobic sequence, i.e., a sequence above the dashed line, e.g., the sequence of about residues 195–210 of SEQ ID NO: 2; all or part of a hydrophilic sequence, i.e., a sequence below the dashed line, e.g., the sequence of residues 455–475 of SEQ ID NO: 2; a sequence which includes a cysteine residue; or a glycosylation site.

The human 13245 cDNA sequence (FIG. 1; SEQ ID NO: 1), which is approximately 6575 nucleotide residues long including non-translated regions, contains a predicted methionine-initiated coding sequence of about 6160 nucleotide residues, excluding termination codon (i.e., nucleotide residues 19–6178 of SEQ ID NO: 1; also shown in SEQ ID NO: 3). The coding sequence encodes a 2053 amino acid protein having the amino acid sequence SEQ ID NO: 2.

Human 13245 contains the following regions or other structural features: a predicted pkinase domain (PF00069) at about amino acid residues 97–360 of SEQ ID NO: 2, a predicted protein kinase C terminal domain at residues 361–390 of SEQ ID NO: 2, a serine/threonine protein kinase active site signature sequence at residues 217–229 of SEQ ID NO: 2, predicted leucine zipper domains at residues 838–859, 975–996, 1041–1062, and 1143–1164 of SEQ ID NO: 2, a predicted carbamoyl-phosphate synthase subdomain signature sequence at residues 1156–1163 of SEQ ID NO: 2, a predicted phorbol ester/diacylglycerol binding domain at residues 1389–1437 of SEQ ID NO: 2, a predicted pleckstrin homology (PH) domain at residues 1470–1525 of SEQ ID NO: 2, and a predicted CNH domain at residues 1568–1865 of SEQ ID NO: 2.

The human 13245 protein has predicted N-glycosylation sites (Pfam accession number PS00001) at about amino acid residues 819–822, 1571–1574, 1694–1697, 1717–1720, and 2026–2029 of SEQ ID NO: 2; predicted cAMP-/cGMP-dependent protein kinase phosphorylation sites (Pfam accession number PS00004) at about amino acid residues 78–81, 477–480, 579–582, 601–604, 680–683, 1322–1325, and 1366–1369 of SEQ ID NO: 2; predicted protein kinase C phosphorylation sites (Pfam accession number PS00005) at about amino acid residues 93–95, 248–250, 308–310, 378–380, 487–489, 498–500, 516–518, 546–548, 577–579, 824–826, 872–874, 1025–1027, 1033–1035, 1096–1098, 1144–1146, 1170–1172, 1215–1217, 1268–1270, 1314–1316, 1335–1337, 1363–1365, 1376–1378, 1542–1544, 1724–1726, 1892–1894, 1910–1912, 1963–1965, and 1977–1979 of SEQ ID NO: 2; predicted casein kinase II phosphorylation sites (Pfam accession number PS00006) located at about amino acid residues 83–86, 93–96, 140–143, 361–364, 381–384, 386–389, 410–413, 436–439, 445–448, 480–483, 487–490, 501–504, 529–532, 867–870, 908–911, 935–938, 940–943, 973–976, 1015–1018, 1025–1028, 1046–4049, 1081–1084, 1142–1145, 1170–1173, 1218–1221, 1308–1311, 1314–1317, 1370–1373, 1736–1739, 1794–1797, 1864–1867, 1882–1885, 1904–1907, 1964–1967, and 2012–2015 of SEQ ID NO: 2; a predicted tyrosine kinase phosphorylation site at residues 741–747of SEQ ID NO: 2; predicted N-myristoylation sites (Pfam accession number PS00008) at about amino acid residues 50–5, 1202–1207, 1532–1537, 1584–1589, 1675–1680, and 1999–2004 of SEQ ID NO: 2; a predicted amidation site (Pfam accession number PS00009) at about amino acid residues 134–136 of SEQ ID NO: 2.

For general information regarding PFAM identifiers, PS prefix and PF prefix domain identification numbers, refer to Sonnhammer et al. (1997, Protein 28:405–420) and http://www.psc.edu/general/software/packages/pfam/pfam.html.

The 13245 protein contains a significant number of structural characteristics in common with members of the MDPK family. The term “family” when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., MDPK proteins for any species described in the art. Members of a family can also have common functional characteristics.

A 13245 polypeptide can include a pkinase domain. As used herein, the term “pkinase domain” refers to a protein domain having an amino acid sequence of about 200–300 amino acid residues in length, preferably, at least about 225–300 amino acids, more preferably about 264 amino acid residues and has a bit score for the alignment of the sequence to the pkinase domain (HMM) of at least 100 or greater, preferably 150 or greater, and more preferably 200 or greater. The pkinase domain has been assigned the PFAM accession PF00069 (http://genome.wustl.edu/Pfam/html).

A 13245 polypeptide can include a pkinase domain. As used herein, the term “CNH domain” refers to a protein domain having an amino acid sequence of about 250–350 amino acid residues in length, preferably, at least about 275–325 amino acids, more preferably about 298 amino acid residues and has a bit score for the alignment of the sequence to the pkinase domain (HMM) of at least 100 or greater, preferably 200 or greater, and more preferably 300 or greater. The pkinase domain has been assigned the PFAM accession PF00780 (http://genome.wustl.edu/Pfam/html).

In a preferred embodiment, 13245 polypeptide or protein has a pkinase domain or a region which includes at least about 200–300, more preferably about 225–300, or 264 amino acid residues and has at least about 60%, 70%, 80%, 90%, 95%, 99%, or 100% homology with a pkinase domain, e.g., the pkinase domain of human 13245 (e.g., residues 97–360 of SEQ ID NO: 2).

In another preferred embodiment, 13245 polypeptide or protein has a CNH domain or a region which includes at least about 250–350, more preferably about 275–325, or 298 amino acid residues and has at least about 60%, 70%, 80%, 90%, 95%, 99%, or 100% homology with a CNH domain, e.g., the CNH domain of human 13245 (e.g., residues 1568–1865 of SEQ ID NO: 2).

To identify the presence of a pkinase or CNH domain profile in a 13245 receptor, the amino acid sequence of the protein is searched against a database of HMMs (e.g., the Pfam database, release 2.1) using the default parameters (http://www.sanger.ac.uk/Software/Pfam/HMM_search). For example, the hmmsf program, which is available as part of the HMMER package of search programs, is a family specific default program for PF00069 or PF00780 and score of 100 is the default threshold score for determining a hit. For example, using ORF Analyzer software, a pkinase domain profile was identified in the amino acid sequence of SEQ ID NO: 2 (e.g., amino acids 53–303 of SEQ ID NO: 2). Accordingly, a 13245 protein having at least about 60–70%, more preferably about 70–80%, or about 80–90% homology with the pkinase domain profile or the CNH domain profile of human 13245 is within the scope of the invention.

While not being bound by any particular theory of operation, 13245 protein is believed to be, in at least one embodiment, a nuclear membrane protein having its carboxyl-terminal domain oriented within the nuclear envelope. In this embodiment, 13245 protein is capable of transmitting signaling information from the cytoplasm to the nucleus, whereby, for example, gene transcription can be regulated.

In one embodiment of the invention, a 13245 polypeptide includes at least one pkinase domain. In another embodiment, the 13245 polypeptide includes at least one pkinase domain and at least one CNH domain. The 13245 molecules of the present invention can further include one or more of the N-glycosylation, cAMP-/cGMP-dependent protein kinase phosphorylation, protein kinase C phosphorylation, casein kinase II phosphorylation, tyrosine kinase phosphorylation, N-myristoylation, amidation, leucine zipper, serine/threonine protein kinase active site, carbamoyl-phosphate synthase sub-domain signature, protein kinase C terminal domain phorbol ester/diacylglycerol binding, and pleckstrin homology domains and sites described herein, and preferably comprises most or all of them.

As shown in FIG. 3, 13245 protein exhibits significant sequence homology with several proteins related to citron protein, which is known to interact with GTPase enzymes of the Rho family. These GTPases include, for example, Rho-A, -B, and -C, Rac-1 and -2, and CDC42. These GTPases regulate cell structure, including cell shape, cell contraction, cell movement, distribution of structural proteins (e.g., actin) within the cell, formation of focal adhesions, cytokinesis, and cell division. These GTPases are also known to modulate gene expression in a phosphorylation-dependent manner. Proteins that are able to interact with, catalyze interconversion of phosphorylated and non-phosphorylated Rho GTPase isoforms, or both, are able to modulate these cellular processes.

Occurrence of pkinase, pkinase_C, a protein kinase ATP-binding region signature, a serine/threonine protein kinase active site signature, a tyrosine kinase phosphorylation site, multiple potential phosphorylation sites, and similarity with citron proteins indicates that 13245 protein is able to interact with Rho GTPases and catalyze interconversion of their phosphorylated and non-phosphorylated forms. Ability of 13245 to modulate the phosphorylation state of Rho GTPases indicates that 13245 is able to modulate one or more of cell shape, cell contraction, cell movement, distribution of structural proteins (e.g., actin) within the cell, formation of focal adhesions, cytokinesis, and cell division in cells in which it is expressed. Furthermore, these characteristics indicate that 13245 protein is involved in disorders in which one or more of these processes are aberrant. 13245 molecules described herein can therefore be used to predict, diagnose, inhibit, prevent, alleviate, or cure these disorders. Examples of disorders in which one or more of these processes are aberrant include tumorigenesis, tumor growth, tumor metastasis, and viral infection of a cell.

Expression of 13245 is greater in peripheral blood cells than in many other cell types, and enhanced expression of 13245 is observed in HIV-1-infected cells, including cells of the CCRF cell line that have been infected with this virus. HIV-1-infected cells undergo various morphological changes, and the pattern of gene expression in HIV-1-infected cells differs from the pattern observed in non-infected cells of the same type. These observations indicate that 13245 has a role in the effects of HIV-1 infection on host cells (e.g., peripheral blood mononuclear cells). Modulating 13245 expression, activity, or both in HIV-1-infected cells can modulate the processes listed above, thereby alleviating or reversing the effects of HIV-1 infection. By way of example 13245 molecules described herein can be used to inhibit insertion of the HIV-1 genome into the host cell genome, inhibit or reverse maintenance of the HIV-1 genome within the host cell genome, inhibit or reverse cytological changes induced by HIV-1 infection, inhibit HIV-1 virus production in infected cells, inhibit interaction of HIV-1 virions with the host cell cytoplasmic membrane, inhibit encapsulation of HIV-1 virus particles in portions of the host cell membrane, or inhibit HIV-1 virus release from infected cells. 13245 molecules can therefore be used to treat individuals who are infected with HIV-1 (e.g., individuals afflicted with acquired immune deficiency syndrome) or with other pathogenic viruses or to inhibit transmission of the virus from one individual to another.

Because the 13245 polypeptides of the invention can modulate 13245-mediated activities, they can be used to develop novel diagnostic and therapeutic agents for 13245-mediated or related disorders, as described below.

As used herein, a "13245 activity," "biological activity of 13245," or "functional activity of 13245," refers to an activity exerted by a 13245 protein, polypeptide or nucleic acid molecule on, for example, a 13245-responsive cell or on a 13245 substrate (e.g., a protein substrate such as a skeletal muscle voltage-gated sodium channel protein) as determined in vivo or in vitro. In one embodiment, a 13245 activity is a direct activity, such as association with a 13245 target molecule. A "target molecule" or "binding partner" of a 13245 protein is a molecule (e.g., a protein or nucleic acid)

with which the 13245 protein binds or interacts in nature. In an exemplary embodiment, such a target molecule is a 13245 receptor. A 13245 activity can also be an indirect activity, such as a cellular signaling activity mediated by interaction of the 13245 protein with a 13245 receptor.

The 13245 molecules of the present invention are predicted to have similar biological activities as MDPK family members. For example, the 13245 proteins of the present invention can have one or more of the following activities:

(1) catalyzing formation of a covalent bond within or between an amino acid residue and a phosphate moiety;

(2) modulating cell contractility;

(3) modulating cell growth;

(4) modulating cell conductivity;

(5) modulating entry of a cell into the cell cycle;

(6) modulating progression of a cell through the cell cycle;

(7) modulating mitogenesis;

(8) modulating cell metabolism;

(9) modulating gene transcription;

(10) catalyzing interconversion of phosphorylated and non-phosphorylated forms of a GTPase, such as a Rho GTPase;

(11) modulating cytokinesis;

(12) modulating cell shape;

(13) modulating cell movement (e.g., tumor metastasis);

(14) modulating integration of a viral genome into a host cell genome;

(15) modulating maintenance of a viral genome within a host cell genome;

(16) modulating cytological changes in a virus-infected host cell;

(17) modulating virus production in a virus-infected host cell;

(18) modulating interaction of a virion with a membrane of a virus-infected host cell; and

(19) modulating encapsulation of a virion within a portion of a membrane of a virus-infected host cell.

Thus, 13245 molecules described herein can act as novel diagnostic targets and therapeutic agents for prognosticating, diagnosing, preventing, inhibiting, alleviating, or curing MDPK-related disorders.

Other activities, as described below, include the ability to modulate function, survival, morphology, proliferation and/or differentiation of cells of tissues in which 13245 molecules are expressed. Thus, the 13245 molecules can act as novel diagnostic targets and therapeutic agents for controlling disorders involving aberrant activities of these cells.

The 13245 molecules can also act as novel diagnostic targets and therapeutic agents for controlling various disorders, including skeletal muscle disorders (e.g., muscular and myotonic dystrophies as described herein and in the art).

The 13245 protein, fragments thereof, and derivatives and other variants of the sequence in SEQ ID NO: 2 thereof are collectively referred to as "polypeptides or proteins of the invention" or "13245 polypeptides or proteins". Nucleic acid molecules encoding such polypeptides or proteins are collectively referred to as "nucleic acids of the invention" or "13245 nucleic acids." 13245 molecules refer to 13245 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules that are separated from other nucleic acid molecules that are present in the natural source of the nucleic acid. For example, with regards to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5'- and/or 3'-ends of the nucleic acid) in the genomic DNA of the organism from which the nucleic acid is derived. For example, in various embodiments, the isolated nucleic acid molecule can contain less than about 5 kilobases, 4 kilobases, 3 kilobases, 2 kilobases, 1 kilobase, 0.5 kilobase or 0.1 kilobase of 5'- and/or 3'-nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in available references (e.g., Current Protocols in Molecular Biology, John Wiley & Sons, N.Y., 1989, 6.3.1–6.3.6). Aqueous and non-aqueous methods are described in that reference and either can be used. A preferred example of stringent hybridization conditions are hybridization in 6×sodium chloride/sodium citrate (SSC) at about 45° C., followed by one or more washes in 0.2×SSC, 0.1% (w/v) SDS at 50° C. Another example of stringent hybridization conditions are hybridization in 6×SSC at about 45° C., followed by one or more washes in 0.2×SSC, 0.1% (w/v) SDS at 55° C. A further example of stringent hybridization conditions are hybridization in 6×SSC at about 45° C., followed by one or more washes in 0.2×SSC, 0.1% (w/v) SDS at 60° C. Preferably, stringent hybridization conditions are hybridization in 6×SSC at about 45° C., followed by one or more washes in 0.2×SSC, 0.1% (w/v) SDS at 65° C. Particularly preferred stringency conditions (and the conditions that should be used if the practitioner is uncertain about what conditions should be applied to determine if a molecule is within a hybridization limitation of the invention) are 0.5 molar sodium phosphate, 7% (w/v) SDS at 65° C., followed by one or more washes at 0.2×SSC, 0.1% (w/v) SDS at 65° C. Preferably, an isolated nucleic acid molecule of the invention that hybridizes under stringent conditions to the sequence of SEQ ID NO: 1 or SEQ ID NO: 3, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene " and "recombinant gene" refer to nucleic acid molecules which include an open reading frame encoding a 13245 protein, preferably a mammalian 13245 protein, and can further include non-coding regulatory sequences and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 13245 protein having less than about 30%, 20%, 10% and more preferably 5% (by dry weight), of non-13245 protein (also referred to herein as a "contaminating protein"), or of chemical precursors or non-13245 chemicals. When the 13245 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 13245 (e.g., the sequence of either of SEQ ID NOs: 1 and 3) without abolishing or, more preferably, without substantially altering a biological activity, whereas an "essential" amino acid residue results in such a change. For example, amino acid residues that are conserved among the polypeptides of the present invention, e.g., those present in the pkinase domain are predicted to be particularly non-amenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 13245 protein is preferably replaced with another amino acid residue from the same side chain family. Alternatively, in another embodiment, mutations can be introduced randomly along all or part of a 13245 coding sequence, such as by saturation mutagenesis, and the resultant mutants can be screened for 13245 biological activity to identify mutants that retain activity. Following mutagenesis of SEQ ID NO: 1 or 3, the encoded protein can be expressed recombinantly and the activity of the protein can be determined.

As used herein, a "biologically active portion" of a 13245 protein includes a fragment of a 13245 protein that participates in an interaction between a 13245 molecule and a non-13245 molecule. Biologically active portions of a 13245 protein include peptides comprising amino acid sequences sufficiently homologous to or derived from the amino acid sequence of the 13245 protein, e.g., the amino acid sequence shown in SEQ ID NO: 2, which include less amino acids than the full length 13245 proteins, and exhibit at least one activity of a 13245 protein. Typically, biologically active portions comprise a domain or motif with at least one activity of the 13245 protein, e.g., a domain or motif capable of catalyzing an activity described herein, such as covalent addition of a phosphate moiety to a protein amino acid residue (e.g., to a serine or threonine hydroxyl group).

A biologically active portion of a 13245 protein can be a polypeptide that for example, 10, 25, 50, 100, 200, 300, or 400, 500, 1000, 1500, or 2000 or more amino acids in length. Biologically active portions of a 13245 protein can be used as targets for developing agents that modulate a 13245-mediated activity, e.g., a biological activity described herein.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 13245 amino acid sequence of SEQ ID NO: 2, 100 amino acid residues, preferably at least 200, 300, 400, 500, 1000, 1500, or 2000 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970, J. Mol. Biol. 48:444–453) algorithm which has been incorporated into the GAP program in the GCG software package (available at http://www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

The percent identity between two amino acid or nucleotide sequences can be determined using the algorithm of Meyers et al. (1989, CABIOS, 4:11–17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990, J. Mol. Biol. 215:403–410). BLAST nucleotide searches can be performed with the NBLAST program, score=100, wordlength=12 to obtain nucleotide sequences homologous to 13245 nucleic acid molecules of the invention. BLAST protein searches can be performed with the XBLAST program, score=50, wordlength=3 to obtain amino acid sequences homologous to 13245 protein molecules of the invention. To obtain gapped alignments for comparison purposes, gapped BLAST can be utilized as described in Altschul et al. (1997, Nucl. Acids Res. 25:3389–3402). When using BLAST and gapped BLAST programs, the default parameters of the respective programs (e.g., XBLAST and NBLAST) can be used. See <http://www.ncbi.nlm.nih.gov>.

"Malexpression or aberrant expression," as used herein, refers to a non-wild-type pattern of gene expression, at the RNA or protein level. It includes: expression at non-wild-type levels, i.e., over- or under-expression; a pattern of expression that differs from wild-type in terms of the time or stage at which the gene is expressed, e.g., increased or decreased expression (as compared with wild-type) at a predetermined developmental period or stage; a pattern of expression that differs from wild-type in terms of decreased expression (as compared with wild-type) in a predetermined cell type or tissue type; a pattern of expression that differs from wild-type in terms of the splicing size, amino acid sequence, post-transitional modification, or biological activity of the expressed polypeptide; a pattern of expression that differs from wild-type in terms of the effect of an environmental stimulus or extracellular stimulus on expression of the gene, e.g., a pattern of increased or decreased expression (as compared with wild-type) in the presence of an increase or decrease in the strength of the stimulus.

"Subject," as used herein, can refer to a mammal, e.g., a human, or to an experimental or animal or disease model. The subject can also be a non-human animal, e.g., a horse, cow, goat, or other domestic animal.

A "purified preparation of cells," as used herein, refers to, in the case of plant or animal cells, an in vitro preparation of cells and not an entire intact plant or animal. In the case of cultured cells or microbial cells, it consists of a preparation of at least 10%, and more preferably, 50% of the subject cells.

Various aspects of the invention are described in further detail below.

Isolated Nucleic Acid Molecules

In one aspect, the invention provides, an isolated or purified, nucleic acid molecule that encodes a 13245 polypeptide described herein, e.g., a full-length 13245 protein or a fragment thereof, e.g., a biologically active portion of 13245 protein. Also included is a nucleic acid fragment suitable for use as a hybridization probe, which can be used, e.g., to a identify nucleic acid molecule encoding a polypeptide of the invention, 13245 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO: 1, or a portion thereof. In one embodiment, the nucleic acid molecule includes sequences encoding the human 13245 protein (i.e., "the coding region," from nucleotides 19–6178 of SEQ ID NO: 1), as well as 5'-non-translated sequences (nucleotides 1–18 of SEQ ID NO: 1) or 3'-non-translated sequences (nucleotides 6179–6575 of SEQ ID NO: 1). Alternatively, the nucleic acid molecule can include only the coding region of SEQ ID NO: 1 (e.g., nucleotides 19–6178, corresponding to SEQ ID NO: 3) and, e.g., no flanking sequences which normally accompany the subject sequence. In another embodiment, the nucleic acid molecule encodes a sequence corresponding to the 2053 amino acid residue protein of SEQ ID NO: 2.

In another embodiment, an isolated nucleic acid molecule of the invention includes a nucleic acid molecule which is a complement of the nucleotide sequence shown in either of SEQ ID NOs: 1 and 3, and a portion of either of these sequences. In other embodiments, the nucleic acid molecule of the invention is sufficiently complementary to the nucleotide sequence shown in either of SEQ ID NOs: 1 and 3 that it can hybridize with a nucleic acid having that sequence, thereby forming a stable duplex.

In one embodiment, an isolated nucleic acid molecule of the invention includes a nucleotide sequence which is at least about 60%, 65%, 70%, 75%, 80%, 80%, 90%, 91%, 92%, 93%, 94%, 95%, 96%, 97%, 98%, or 99% or more homologous to the entire length of the nucleotide sequence shown in either of SEQ ID NOs: 1 and 3, or a portion, preferably of the same length, of either of these nucleotide sequences.

13245 Nucleic Acid Fragments

A nucleic acid molecule of the invention can include only a portion of the nucleic acid sequence of one of SEQ ID NOs: 1 and 3. For example, such a nucleic acid molecule can include a fragment that can be used as a probe or primer or a fragment encoding a portion of a 13245 protein, e.g., an immunogenic or biologically active portion of a 13245 protein. A fragment can comprise nucleotides corresponding to residues 97–360 of SEQ ID NO: 2, which encodes a pkinase domain of human 13245, or to residues 1568–1865 of SEQ ID NO: 2, which encodes a CNH domain of human 13245. The nucleotide sequence determined from the cloning of the 13245 gene facilitates generation of probes and primers for use in identifying and/or cloning other 13245 family members, or fragments thereof, as well as 13245 homologues, or fragments thereof, from other species.

In another embodiment, a nucleic acid includes a nucleotide sequence that includes part, or all, of the coding region and extends into either (or both) the 5'- or 3'-non-coding region. Other embodiments include a fragment that includes a nucleotide sequence encoding an amino acid fragment described herein. Nucleic acid fragments can encode a specific domain or site described herein or fragments thereof, particularly fragments thereof that are at least about 250 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein.

13245 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of either of SEQ ID NOs: 1 and 3, or a naturally occurring allelic variant or mutant of either of SEQ ID NOs: 1 and 3.

In a preferred embodiment the nucleic acid is a probe which is at least 5 or 10, and less than 200, more preferably less than 100, or less than 50, base pairs in length. It should be identical, or differ by 1, or fewer than 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid that encodes a pkinase domain at about amino acid residues 97 to 360 of SEQ ID NO: 2 or the predicted CNH domain at about amino acid residues 1568 to 1865 of SEQ ID NO: 2.

In another embodiment a set of primers is provided, e.g., primers suitable for use in a PCR, which can be used to amplify a selected region of a 13245 sequence. The primers should be at least 5, 10, or 50 base pairs in length and less than 100, or less than 200, base pairs in length. The primers should be identical, or differs by one base from a sequence disclosed herein or from a naturally occurring variant. Primers suitable for amplifying all or a portion of any of the following regions are provided: e.g., one or more a pkinase domain and the predicted CNH domain, as defined above relative to SEQ ID NO: 2.

A nucleic acid fragment can encode an epitope bearing region of a polypeptide described herein.

A nucleic acid fragment encoding a "biologically active portion of a 13245 polypeptide" can be prepared by isolating a portion of the nucleotide sequence of either of SEQ ID NOs: 1 and 3, which encodes a polypeptide having a 13245 biological activity (e.g., the biological activities of the 13245 proteins are described herein), expressing the encoded portion of the 13245 protein (e.g., by recombinant expression in vitro) and assessing the activity of the encoded portion of the 13245 protein. For example, a nucleic acid fragment encoding a biologically active portion of 13245 includes a pkinase domain, e.g., amino acid residues 97 to 360 of SEQ ID NO: 2, or a CNH domain, e.g., amino acid residues 1568 to 1865 of SEQ ID NO: 2. A nucleic acid fragment encoding a biologically active portion of a 13245 polypeptide can comprise a nucleotide sequence that is greater than 25 or more nucleotides in length.

In one embodiment, a nucleic acid includes one that has a nucleotide sequence which is greater than 260, 300, 400, 500, 600, 700, 800, 900, 1000, 1100, 1200, 1300, 1400, 1500, 2000, 2500, 3000, 4000, 5000, or 6000 or more nucleotides in length and that hybridizes under stringent hybridization conditions with a nucleic acid molecule having the sequence of either of SEQ ID NOs: 1 and 3.

13245 Nucleic Acid Variants

The invention further encompasses nucleic acid molecules having a sequence that differs from the nucleotide sequence shown in either of SEQ ID NOs: 1 and 3. Such differences can be attributable to degeneracy of the genetic code (i.e., differences which result in a nucleic acid that encodes the same 13245 proteins as those encoded by the nucleotide sequence disclosed herein). In another embodiment, an isolated nucleic acid molecule of the invention encodes a protein having an amino acid sequence which differs by at least 1, but by fewer than 5, 10, 20, 50, or 100, amino acid residues from SEQ ID NO: 2. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. For example, the nucleic acid can be one in which at least one codon, at preferably at least 10%, or 20% of the codons has been altered such that the sequence is optimized for expression in *E. coli*, yeast, human, insect, or CHO cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid has a sequence that differs from that of either of SEQ ID NOs: 1 and 3, e.g., as follows: by at least one, but by fewer than 10, 20, 30, or 40, nucleotide residues; or by at least one but by fewer than 1%, 5%, 10% or 20% of the nucleotide residues in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the nucleotide sequence shown in either of SEQ ID NOs: 1 and 3, or a fragment of either of these sequences. Such nucleic acid molecules can readily be identified as being able to hybridize under stringent conditions, to the nucleotide sequence shown in either of SEQ ID NOs: 1 and 3, or a fragment of either of these sequences. Nucleic acid molecules corresponding to orthologs, homologs, and allelic variants of the 13245 cDNAs of the invention can further be isolated by mapping to the same chromosome or locus as the 13245 gene.

Preferred variants include those that are correlated with any of the 13245 biological activities described herein, e.g., catalyzing formation of a covalent bond between an amino acid residue of a protein (e.g., a serine or threonine residue) and a phosphate moiety.

Allelic variants of 13245 (e.g., human 13245) include both functional and non-functional proteins. Functional allelic variants are naturally occurring amino acid sequence variants of the 13245 protein within a population that maintain the ability to mediate any of the 13245 biological activities described herein.

Functional allelic variants will typically contain only conservative substitution of one or more amino acids of SEQ ID NO: 2, or substitution, deletion or insertion of non-critical residues in non-critical regions of the protein. Non-functional allelic variants are naturally-occurring amino acid sequence variants of the 13245 (e.g., human 13245) protein within a population that do not have the ability to mediate any of the 13245 biological activities described herein. Non-functional allelic variants will typically contain a non-conservative substitution, a deletion, or insertion, or premature truncation of the amino acid sequence of SEQ ID NO: 2, or a substitution, insertion, or deletion in critical residues or critical regions of the protein.

Moreover, nucleic acid molecules encoding other 13245 family members and, thus, which have a nucleotide sequence which differs from the 13245 sequences of either of SEQ ID NOs: 1 and 3 are within the scope of the invention.

Antisense Nucleic Acid Molecules, Ribozymes and Modified 13245 Nucleic Acid Molecules In another aspect, the invention features, an isolated nucleic acid molecule that is antisense to 13245. An "antisense" nucleic acid can include a nucleotide sequence that is complementary to a "sense" nucleic acid encoding a protein, e.g., complementary to the coding strand of a double-stranded cDNA molecule or complementary to an mRNA sequence. The antisense nucleic acid can be complementary to an entire 13245 coding strand, or to only a portion thereof (e.g., the coding region of human 13245 corresponding to SEQ ID NO: 3). In another embodiment, the antisense nucleic acid molecule is antisense to a "non-coding region" of the coding strand of a nucleotide sequence encoding 13245 (e.g., the 5'- and 3'-non-translated regions).

An antisense nucleic acid can be designed such that it is complementary to the entire coding region of 13245 mRNA, but more preferably is an oligonucleotide that is antisense to only a portion of the coding or non-coding region of 13245 mRNA. For example, the antisense oligonucleotide can be complementary to the region surrounding the translation start site of 13245 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, or 80 or more nucleotide residues in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 13245 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an alpha-anomeric nucleic acid molecule. An alpha-anomeric nucleic acid molecule forms specific double-stranded hybrids with complementary RNA in which, contrary to the usual beta-units, the strands run parallel to each other (Gaultier et al., 1987, Nucl. Acids. Res. 15:6625–6641). The antisense nucleic acid molecule can also comprise a 2'-o-methylribonucleotide (Inoue et al., 1987, Nucl. Acids Res. 15:6131–6148) or a chimeric RNA-DNA analogue (Inoue et al., 1987, FEBS Lett. 215:327–330).

In still another embodiment, an antisense nucleic acid of the invention is a ribozyme. A ribozyme having specificity for a 13245-encoding nucleic acid can include one or more sequences complementary to the nucleotide sequence of a 13245 cDNA disclosed herein (i.e., SEQ ID NO: 1 or SEQ ID NO: 3), and a sequence having known catalytic sequence responsible for mRNA cleavage (see, for example, U.S. Pat. No. 5,093,246 or Haselhoff et al. (1988, Nature 334:585–591). For example, a derivative of a Tetrahymena L-19 IVS RNA can be constructed in which the nucleotide sequence of the active site is complementary to the nucleotide sequence to be cleaved in a 13245-encoding mRNA (e.g., U.S. Pat. No. 4,987,071; and U.S. Pat. No. 5,116,742). Alternatively, 13245 mRNA can be used to select a catalytic RNA having a specific ribonuclease activity from a pool of RNA molecules (e.g., Bartel et al., 1993, Science 261:1411–1418).

13245 gene expression can be inhibited by targeting nucleotide sequences complementary to the regulatory region of the 13245 (e.g., the 13245 promoter and/or enhancers) to form triple helical structures that prevent transcription of the 13245 gene in target cells (Helene, 1991, Anticancer Drug Des. 6:569–584; Helene, et al., 1992, Ann. N.Y. Acad. Sci. 660:27–36; Maher, 1992, Bioassays 14:807–815). The potential sequences that can be targeted for triple helix formation can be increased by creating a so-called "switchback" nucleic acid molecule. Switchback molecules are synthesized in an alternating 5' to 3', 3' to 5' manner, such that they hybridize with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 13245 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (Hyrup et al., 1996, Bioorg. Med. Chem. 4:5–23). As used herein, the terms "peptide nucleic acid" (PNA) refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al. (1996, supra; Perry-O'Keefe et al., Proc. Natl. Acad. Sci. USA 93:14670–14675).

PNAs of 13245 nucleic acid molecules can be used in therapeutic and diagnostic applications. For example, PNAs can be used as antisense or anti-gene agents for sequence-specific modulation of gene expression by, for example, inducing transcription or translation arrest or inhibiting replication. PNAs of 13245 nucleic acid molecules can also be used in the analysis of single base pair mutations in a gene, (e.g., by PNA-directed PCR clamping); as 'artificial restriction enzymes' when used in combination with other enzymes, (e.g., S1 nucleases, as described in Hyrup et al., 1996, supra); or as probes or primers for DNA sequencing or hybridization (Hyrup et al., 1996, supra; Perry-O'Keefe, supra).

In other embodiments, the oligonucleotide can include other appended groups such as peptides (e.g., for targeting host cell receptors in vivo), or agents facilitating transport across the cell membrane (e.g., Letsinger et al., 1989, Proc. Natl. Acad. Sci. USA 86:6553–6556; Lemaitre et al., 1987, Proc. Natl. Acad. Sci. USA 84:648–652; PCT publication number WO 88/09810) or the blood-brain barrier (see, e.g., PCT publication number WO 89/10134). In addition, oligonucleotides can be modified with hybridization-triggered cleavage agents (e.g., Krol et al., 1988, Bio-Techniques 6:958–976) or intercalating agents (e.g., Zon, 1988, Pharm. Res. 5:539–549). To this end, the oligonucleotide can be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 13245 nucleic acid of the invention, two complementary regions, one having a fluorophore and the other having a quencher, such that the molecular beacon is useful for quantitating the presence of the 13245 nucleic acid of the invention in a sample. Molecular beacon nucleic acids are described, for example, in U.S. Pat. Nos. 5,854,033, 5,866,336, and 5,876,930.

Isolated 13245 Polypeptides

In another aspect, the invention features, an isolated 13245 protein, or fragment, e.g., a biologically active portion, for use as immunogens or antigens to raise or test (or more generally to bind) anti-13245 antibodies. 13245 protein can be isolated from cells or tissue sources using standard protein purification techniques. 13245 protein or fragments thereof can be produced by recombinant DNA techniques or synthesized chemically.

Polypeptides of the invention include those that arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when the polypeptide is expressed in a native cell, or in systems which result in the alteration or omission of post-translational modifications, e.g., glycosylation or cleavage, present when expressed in a native cell.

In a preferred embodiment, a 13245 polypeptide has one or more of the following characteristics:

(1) it catalyzes formation of a covalent bond within or between an amino acid residue and a phosphate moiety;

(2) it modulates cell contractility;

(3) it modulates cell growth;

(4) it modulates cell conductivity;

(5) it modulates entry of a cell into the cell cycle;

(6) it modulates progression of a cell through the cell cycle;

(7) it modulates mitogenesis;

(8) it modulates cell metabolism; and (9) it modulates gene transcription;

(10) it catalyzes interconversion of phosphorylated and non-phosphorylated forms of a GTPase, such as a Rho GTPase;

(11) it modulates cytokinesis;

(12) it modulates cell shape;

(13) it modulates cell movement (e.g., tumor metastasis);

(14) it modulates integration of a viral genome into a host cell genome;

(15) it modulates maintenance of a viral genome within a host cell genome;

(16) it modulates cytological changes in a virus-infected host cell;

(17) it modulates virus production in a virus-infected host cell;

(18) it modulates interaction of a virion with a membrane of a virus-infected host cell;

(19) it modulates encapsulation of a virion within a portion of a membrane of a virus-infected host cell

(20) it has a molecular weight, amino acid composition or other physical characteristic of a 13245 protein of SEQ ID NO: 2;

(21) it has an overall sequence similarity (identity) of at least 60–65%, preferably at least 70%, more preferably at least 75, 80, 85, 86, 87, 88, 89, 90, 91, 92, 93, 94, 95, 96, 97, 98, or 99% or more, with a portion of SEQ ID NO: 2;

(22) it has a CNH domain which is preferably about 70%, 80%, 90%, 95%, 96%, 97%, 98%, or 99% or more, identical with amino acid residues 1568–1865 of SEQ ID NO:2; or

(23) it has at least one pkinase domain which is preferably about 70%, 80%, 90%, 95%, 96%, 97%, 98%, or 99% or more, identical with amino acid residues 97–360 of SEQ ID NO: 2.

In a preferred embodiment, the 13245 protein or fragment thereof differs only insubstantially, if at all, from the corresponding sequence in SEQ ID NO: 2. In one embodiment, it differs by at least one, but by fewer than 15, 10 or 5 amino acid residues. In another, it differs from the corresponding sequence in SEQ ID NO: 2 by at least one residue but fewer than 20%, 15%, 10% or 5% of the residues differ from the corresponding sequence in SEQ ID NO: 2 (if this comparison requires alignment the sequences should be aligned for maximum homology. "Looped" out sequences from deletions or insertions, or mismatches, are considered differences). The differences are, preferably, differences or changes at a non-essential amino acid residues or involve a conservative substitution of one residue for another. In a preferred embodiment the differences are not in residues 97–360 or 1568–1865 of SEQ ID NO: 2.

Other embodiments include a protein that has one or more changes in amino acid sequence, relative to SEQ ID NO: 2 (e.g., a change in an amino acid residue which is not essential for activity). Such 13245 proteins differ in amino acid sequence from SEQ ID NO: 2, yet retain biological activity.

In one embodiment, the protein includes an amino acid sequence at least about 60%, 65%, 70%, 75%, 80%, 85%, 90%, 95%, 98% or more homologous to SEQ ID NO: 2.

A 13245 protein or fragment is provided which has an amino acid sequence which varies from SEQ ID NO: 2 in one or both of the regions corresponding to residues 1–96, 361–1567, and 1866–2053 of SEQ ID NO: 2 by at least one, but by fewer than 15, 10 or 5 amino acid residues, but which does not differ from SEQ ID NO: 2 in the region corresponding to residues 97–360 and 1568–1865 of SEQ ID NO: 2 (if this comparison requires alignment the sequences should be aligned for maximum homology. "Looped" out sequences from deletions or insertions, or mismatches, are considered differences). In some embodiments the difference is at a non-essential residue or is a conservative substitution, while in others the difference is at an essential residue or is a non-conservative substitution.

A biologically active portion of a 13245 protein should include the 13245 pkinase domain, the 13245 CNH domain, or both. Moreover, other biologically active portions, in which other regions of the protein are deleted, can be prepared by recombinant techniques and evaluated for one or more of the functional activities of a native 13245 protein.

In a preferred embodiment, the 13245 protein has the amino acid sequence SEQ ID NO: 2. In other embodiments, the 13245 protein is substantially identical to SEQ ID NO: 2. In yet another embodiment, the 13245 protein is substantially identical to SEQ ID NO: 2 and retains the functional activity of the protein of SEQ ID NO: 2.

13245 Chimeric or Fusion Proteins

In another aspect, the invention provides 13245 chimeric or fusion proteins. As used herein, a 13245 "chimeric protein" or "fusion protein" includes a 13245 polypeptide linked to a non-13245 polypeptide. A "non-13245 polypeptide" refers to a polypeptide having an amino acid sequence corresponding to a protein which is not substantially homologous to the 13245 protein, e.g., a protein which is different from the 13245 protein and which is derived from the same or a different organism. The 13245 polypeptide of the fusion protein can correspond to all or a portion e.g., a fragment described herein of a 13245 amino acid sequence. In a preferred embodiment, a 13245 fusion protein includes at least one or more biologically active portions of a 13245 protein. The non-13245 polypeptide can be fused to the amino or carboxyl terminus of the 13245 polypeptide.

The fusion protein can include a moiety that has a high affinity for a ligand. For example, the fusion protein can be a GST-13245 fusion protein in which the 13245 sequences are fused to the carboxyl terminus of the GST sequences. Such fusion proteins can facilitate the purification of recombinant 13245. Alternatively, the fusion protein can be a 13245 protein containing a heterologous signal sequence at its amino terminus. In certain host cells (e.g., mammalian host cells), expression and/or secretion of 13245 can be increased through use of a heterologous signal sequence.

Fusion proteins can include all or a part of a serum protein, e.g., an IgG constant region, or human serum albumin.

The 13245 fusion proteins of the invention can be incorporated into pharmaceutical compositions and administered to a subject in vivo. The 13245 fusion proteins can be used to affect the bioavailability of a 13245 substrate. 13245 fusion proteins can be useful therapeutically for the treatment of disorders caused by, for example, (i) aberrant modification or mutation of a gene encoding a 13245 protein; (ii) mis-regulation of the 13245 gene; and (iii) aberrant post-translational modification of a 13245 protein.

Moreover, the 13245-fusion proteins of the invention can be used as immunogens to produce anti-13245 antibodies in a subject, to purify 13245 ligands and in screening assays to identify molecules that inhibit the interaction of 13245 with a 13245 substrate.

Expression vectors are commercially available that already encode a fusion moiety (e.g., a GST polypeptide). A 13245-encoding nucleic acid can be cloned into such an expression vector such that the fusion moiety is linked in-frame to the 13245 protein.

Variants of 13245 Proteins

In another aspect, the invention also features a variant of a 13245 polypeptide, e.g., which functions as an agonist (mimetics) or as an antagonist. Variants of the 13245 proteins can be generated by mutagenesis, e.g., discrete point mutation, the insertion or deletion of sequences or the truncation of a 13245 protein. An agonist of the 13245 proteins can retain substantially the same, or a subset, of the biological activities of the naturally occurring form of a 13245 protein. An antagonist of a 13245 protein can inhibit one or more of the activities of the naturally occurring form of the 13245 protein by, for example, competitively modulating a 13245-mediated activity of a 13245 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 13245 protein.

Variants of a 13245 protein can be identified by screening combinatorial libraries of mutants, e.g., truncation mutants, of a 13245 protein for agonist or antagonist activity.

Libraries of fragments e.g., amino-terminal, carboxyl-terminal, or internal fragments, of a 13245 protein coding sequence can be used to generate a variegated population of fragments for screening and subsequent selection of variants of a 13245 protein.

Variants in which a cysteine residue is added or deleted or in which a residue that is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a technique which enhances the frequency of functional mutants in the libraries, can be used in combination with the screening assays to identify 13245 variants (Arkin et al., 1992, Proc. Natl. Acad. Sci. USA 89:7811–7815; Delgrave et al., 1993, Protein Engr. 6:327–331).

Cell based assays can be exploited to analyze a variegated 13245 library. For example, a library of expression vectors can be transfected into a cell line, e.g., a cell line, which ordinarily responds to 13245 in a substrate-dependent manner. The transfected cells are then contacted with 13245 and the effect of the expression of the mutant on signaling by the 13245 substrate can be detected, e.g., by measuring changes in cell growth and/or enzymatic activity. Plasmid DNA can then be recovered from the cells that score for inhibition, or alternatively, potentiation of signaling by the 13245 substrate, and the individual clones further characterized.

In another aspect, the invention features a method of making a 13245 polypeptide, e.g., a peptide having a non-wild-type activity, e.g., an antagonist, agonist, or super agonist of a naturally-occurring 13245 polypeptide, e.g., a naturally-occurring 13245 polypeptide. The method includes: altering the sequence of a 13245 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 13245 polypeptide a biological activity of a naturally occurring 13245 polypeptide. The method includes: altering the sequence, e.g., by substitution or deletion of one or more residues, of a 13245 polypeptide, e.g., altering the sequence of a non-conserved region, or a domain or residue described herein, and testing the altered polypeptide for the desired activity.

Anti-13245 Antibodies

In another aspect, the invention provides an anti-13245 antibody. The term "antibody" as used herein refers to an immunoglobulin molecule or immunologically active portion thereof, i.e., an antigen-binding portion. Examples of immunologically active portions of immunoglobulin molecules include F(ab) and $F(ab')_2$ fragments which can be generated by treating the antibody with an enzyme such as pepsin.

The antibody can be a polyclonal, monoclonal, recombinant, e.g., a chimeric or humanized, fully-human, non-human, e.g., murine, or single chain antibody. In a preferred embodiment, it has effector function and can fix complement. The antibody can be coupled to a toxin or imaging agent.

A full-length 13245 protein or, antigenic peptide fragment of 13245 can be used as an immunogen or can be used to identify anti-13245 antibodies made with other immunogens, e.g., cells, membrane preparations, and the like. The antigenic peptide of 13245 should include at least 8 amino acid residues of the amino acid sequence shown in SEQ ID NO: 2 and encompasses an epitope of 13245. Preferably, the antigenic peptide includes at least 10 amino acid residues, more preferably at least 15 amino acid residues, even more preferably at least 20 amino acid residues, and most preferably at least 30 amino acid residues.

Fragments of 13245 which include about residues 195–210 of SEQ ID NO: 2 can be used to make antibodies, e.g., for use as immunogens or to characterize the specificity of an antibody, against hydrophobic regions of the 13245 protein. Similarly, a fragment of 13245 which include about residues 455–475 of SEQ ID NO: 2 can be used to make an antibody against a hydrophilic region of the 13245 protein.

Antibodies reactive with, or specific for, any of these regions, or other regions or domains described herein are provided.

Preferred epitopes encompassed by the antigenic peptide are regions of 13245 are located on the surface of the protein, e.g., hydrophilic regions, as well as regions with high antigenicity. For example, an Emini surface probability analysis of the human 13245 protein sequence can be used to indicate the regions that have a particularly high probability of being localized to the surface of the 13245 protein and are thus likely to constitute surface residues useful for targeting antibody production.

In a preferred embodiment the antibody binds an epitope on any domain or region on 13245 proteins described herein.

Chimeric, humanized, but most preferably, completely human antibodies are desirable for applications which include repeated administration, e.g., therapeutic treatment (and some diagnostic applications) of human patients.

The anti-13245 antibody can be a single chain antibody. A single-chain antibody (scFV) can be engineered (e.g., Colcher et al., 1999, Ann. N.Y. Acad. Sci. 880:263–280; Reiter, 1996, Clin. Cancer Res. 2:245–252). The single chain antibody can be dimerized or multimerized to generate multivalent antibodies having specificities for different epitopes of the same target 13245 protein.

In a preferred embodiment, the antibody has reduced or no ability to bind an Fc receptor. For example, it can be an isotype, subtype, fragment or other mutant, which does not support binding to an Fc receptor, e.g., it can have a mutated or deleted Fc receptor binding region.

An anti-13245 antibody (e.g., monoclonal antibody) can be used to isolate 13245 by standard techniques, such as affinity chromatography or immunoprecipitation. Moreover, an anti-13245 antibody can be used to detect 13245 protein (e.g., in a cellular lysate or cell supernatant) in order to evaluate the abundance and pattern of expression of the protein. Anti-13245 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 13245 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 13245 proteins, mutant forms of 13245 proteins, fusion proteins, and the like).

The recombinant expression vectors of the invention can be designed for expression of 13245 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel (1990, Gene Expression Technology: Methods in Enzymology 185, Academic Press, San Diego). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase, Typical fusion expression vectors include pGEX (Pharmacia Biotech Inc; Smith et al., 1988, Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 13245 activity assays, (e.g., direct assays or competitive assays described in detail below), or to generate antibodies specific for 13245 proteins. In a preferred embodiment, a fusion protein expressed in a retroviral expression vector of the present invention can be used to infect bone marrow cells that are subsequently transplanted into irradiated recipients. The pathology of the subject recipient is then examined after sufficient time has passed (e.g., six weeks).

To maximize recombinant protein expression in *E. coli*, the protein is expressed in a host bacterial strain with an impaired capacity to proteolytically cleave the recombinant protein (Gottesman, 1990, Gene Expression Technology: Methods in Enzymology 185, Academic Press, San Diego, 119–128). Another strategy is to alter the nucleic acid sequence of the nucleic acid to be inserted into an expression vector so that the individual codons for each amino acid are those preferentially utilized in *E. coli* (Wada et al., 1992, Nucl. Acids Res. 20:2111–2118). Such alteration of nucleic acid sequences of the invention can be carried out by standard DNA synthesis techniques.

The 13245 expression vector can be a yeast expression vector, a vector for expression in insect cells, e.g., a baculovirus expression vector, or a vector suitable for expression in mammalian cells.

When used in mammalian cells, the expression vector's control functions are often provided by viral regulatory elements. For example, commonly used viral promoters are derived from polyoma, adenovirus 2, cytomegalovirus and simian virus 40 (SV40).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al., 1987, Genes Dev. 1:268–277), lymphoid-specific promoters (Calame et al., 1988, Adv. Immunol. 43:235–275), in particular promoters of T cell receptors (Winoto et al., 1989, EMBO J. 8:729–733) and immunoglobulins (Banerji et al., 1983, Cell 33:729–740; Queen et al., 1983, Cell 33:741–748), neuron-specific promoters (e.g., the neurofilament promoter; Byrne et al., 1989, Proc. Natl. Acad. Sci. USA 86:5473–5477), pancreas-specific promoters (Edlund et al., 1985, Science 230:912–916), and mammary gland-specific promoters (e.g., milk whey promoter; U.S. Pat. No. 4,873,316 and European Patent Application publication number 264,166). Developmentally-regulated promoters are also encompassed, for example, the murine hox promoters (Kessel et al., 1990, Science 249:374–379) and the alpha-fetoprotein promoter (Campes et al., 1989, Genes Dev. 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes, see Weintraub, H. et al. (1986, Trends Genet. 1: Review).

Another aspect the invention provides a host cell which includes a nucleic acid molecule described herein, e.g., a 13245 nucleic acid molecule within a recombinant expression vector or a 13245 nucleic acid molecule containing sequences which allow it to homologously recombine into a specific site of the host cell's genome. The terms "host cell" and "recombinant host cell" are used interchangeably herein. Such terms refer not only to the particular subject cell, but also to the progeny or potential progeny of such a cell. Because certain modifications can occur in succeeding generations due to either mutation or environmental influences, such progeny may not, in fact, be identical to the parent cell, but are included within the scope of the term as used herein.

A host cell can be any prokaryotic or eukaryotic cell. For example, a 13245 protein can be expressed in bacterial cells such as *E. coli*, insect cells, yeast or mammalian cells (such as Chinese hamster ovary (CHO) cells) or COS cells. Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 13245 protein. Accordingly, the invention farther provides methods for producing a 13245 protein using the host cells of the invention. In one embodiment, the method includes culturing the host cell of the invention (into which a recombinant expression vector encoding a 13245 protein has been introduced) in a suitable medium such that a 13245 protein is produced. In another embodiment, the method further includes isolating a 13245 protein from the medium or the host cell.

In another aspect, the invention features, a cell or purified preparation of cells which include a 13245 transgene, or which otherwise mal-express 13245. The cell preparation can consist of human or non-human cells, e.g., rodent cells, e.g., mouse or rat cells, rabbit cells, or pig cells. In preferred embodiments, the cell or cells include a 13245 transgene, e.g., a heterologous form of a 13245, e.g., a gene derived from humans (in the case of a non-human cell). The 13245 transgene can be mal-expressed, e.g., over-expressed or under-expressed. In other preferred embodiments, the cell or cells include a gene that mal-expresses an endogenous 13245, e.g., a gene the expression of which is disrupted, e.g., a knockout. Such cells can serve as a model for studying disorders that are related to mutated or mal-expressed 13245 alleles or for use in drug screening.

In another aspect, the invention includes, a human cell, e.g., a hematopoietic stem cell, transformed with nucleic acid that encodes a subject 13245 polypeptide.

Also provided are cells, preferably human cells, e.g., human hematopoietic or fibroblast cells, in which an endogenous 13245 is under the control of a regulatory sequence that does not normally control expression of the endogenous 13245 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 13245 gene. For example, an endogenous 13245 gene that is "transcriptionally silent," e.g., not normally expressed, or expressed only at very low levels, can be activated by inserting a regulatory element that is capable of promoting the expression of a normally expressed gene product in that cell. Techniques such as targeted homologous recombination, can be used to insert the heterologous DNA as described (e.g., U.S. Pat. No. 5,272,071; PCT publication number WO 91/06667).

Transgenic Animals

The invention provides non-human transgenic animals. Such animals are useful for studying the function and/or activity of a 13245 protein and for identifying and/or evaluating modulators of 13245 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 13245 gene has been altered, e.g., by homologous recombination between the endogenous gene and an exogenous DNA molecule introduced into a cell of the animal (e.g., an embryonic cell of the animal, prior to development of the animal).

Intronic sequences and polyadenylation signals can also be included in the transgene to increase the efficiency of expression of the transgene. A tissue-specific regulatory sequence(s) can be operably linked to a transgene of the invention to direct expression of a 13245 protein to particular cells. A transgenic founder animal can be identified based upon the presence of a 13245 transgene in its genome and/or expression of 13245 mRNA in tissues or cells of the animals. A transgenic founder animal can then be used to breed additional animals carrying the transgene. Moreover, transgenic animals carrying a transgene encoding a 13245 protein can further be bred to other transgenic animals carrying other transgenes.

13245 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk- or egg-specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express a 13245 protein (e.g., via a recombinant expression vector in a host cell in gene therapy applications), to detect a 13245 mRNA (e.g., in a biological sample), to detect a genetic alteration in a 13245 gene and to modulate 13245 activity, as described further below. The 13245 proteins can be used to treat disorders characterized by insufficient or excessive production of a 13245 substrate or production of 13245 inhibitors. In addition, the 13245 proteins can be used to screen for naturally occurring 13245 substrates, to screen for drugs or compounds which modulate 13245 activity, as well as to treat disorders characterized by insufficient or excessive production of 13245 protein or production of 13245 protein forms which have decreased, aberrant or unwanted activity compared to 13245 wild-type protein. Exemplary disorders include those in which protein phosphorylation is aberrant (e.g., muscular and myotonic dystrophies). Moreover, the anti-13245 antibodies of the invention can be used to detect and isolate 13245 proteins, regulate the bioavailability of 13245 proteins, and modulate 13245 activity.

A method of evaluating a compound for the ability to interact with, e.g., bind to, a subject 13245 polypeptide is provided. The method includes: contacting the compound with the subject 13245 polypeptide; and evaluating the ability of the compound to interact with, e.g., to bind or form a complex with, the subject 13245 polypeptide. This method can be performed in vitro, e.g., in a cell free system, or in vivo, e.g., in a two-hybrid interaction trap assay. This method can be used to identify naturally-occurring molecules that interact with a subject 13245 polypeptide. It can also be used to find natural or synthetic inhibitors of a subject 13245 polypeptide. Screening methods are discussed in more detail below.

Screening Assays

The invention provides screening methods (also referred to herein as "assays") for identifying modulators, i.e., candidate or test compounds or agents (e.g., proteins, peptides, peptidomimetics, peptoids, small molecules or other drugs) which bind with 13245 proteins, have a stimulatory or inhibitory effect on, for example, 13245 expression or 13245 activity, or have a stimulatory or inhibitory effect on, for example, the expression or activity of a 13245 substrate. Compounds thus identified can be used to modulate the activity of target gene products (e.g., 13245 genes) in a therapeutic protocol, to elaborate the biological function of the target gene product, or to identify compounds that disrupt normal target gene interactions.

In one embodiment, the invention provides assays for screening candidate or test compounds that are substrates of a 13245 protein or polypeptide or a biologically active portion thereof. In another embodiment, the invention provides assays for screening candidate or test compounds that bind to or modulate the activity of a 13245 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; e.g., Zuckermann et al., 1994, J. Med. Chem. 37:2678–2685); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries have been described (e.g., DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233).

Libraries of compounds can be presented in solution (e.g., Houghten, 1992, Biotechniques 13:412–421), or on beads (Lam, 1991, Nature 354:82–84), chips (Fodor, 1993, Nature 364:555–556), bacteria (U.S. Pat. No. 5,223,409), spores (U.S. Pat. No. 5,223,409), plasmids (Cull et al., 1992, Proc. Natl. Acad. Sci. USA 89:1865–1869), or on phage (Scott et al., 1990, Science 249:386–390; Devlin, 1990, Science 249:404–406; Cwirla et al., 1990, Proc. Natl. Acad. Sci. USA 87:6378–6382; Felici, 1991, J. Mol. Biol. 222:301–310; U.S. Pat. No. 5,223,409).

In one embodiment, an assay is a cell-based assay in which a cell which expresses a 13245 protein or biologically active portion thereof is contacted with a test compound, and the ability of the test compound to modulate 13245 activity is determined. Determining the ability of the test compound to modulate 13245 activity can be accomplished by monitoring, for example, changes in enzymatic activity. The cell, for example, can be of mammalian origin.

The ability of the test compound to modulate 13245 binding to a compound, e.g., a 13245 substrate, or to bind to 13245 can also be evaluated. This can be accomplished, for example, by coupling the compound, e.g., the substrate, with a radioisotope or enzymatic label such that binding of the compound, e.g., the substrate, to 13245 can be determined by detecting the labeled compound, e.g., substrate, in a complex. Alternatively, 13245 could be coupled with a radioisotope or enzymatic label to monitor the ability of a test compound to modulate 13245 binding to a 13245 substrate in a complex. For example, compounds (e.g., 13245 substrates) can be labeled with $^{125}I$, $^{35}S$, $^{14}C$, or $^{3}H$, either directly or indirectly, and the radioisotope detected by direct counting of radio-emission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 13245 substrate) to interact with 13245 with or without the labeling of any of the interactants can be evaluated. For example, a microphysiometer can be used to detect the interaction of a compound with 13245 without the labeling of either the compound or the 13245 (McConnell et al., 1992, Science 257:1906–1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 13245.

In yet another embodiment, a cell-free assay is provided in which a 13245 protein or biologically active portion thereof is contacted with a test compound and the ability of the test compound to bind to the 13245 protein or biologically active portion thereof is evaluated. Preferred biologically active portions of the 13245 proteins to be used in assays of the present invention include fragments that participate in interactions with non-13245 molecules, e.g., fragments with high surface probability scores.

Soluble and/or membrane-bound forms of isolated proteins (e.g., 13245 proteins or biologically active portions thereof) can be used in the cell-free assays of the invention. When membrane-bound forms of the protein are used, it can be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-{(3-cholamidopropyl)dimethylamminio}-1-propane sulfonate (CHAPS), 3-{(3-cholamidopropyl)dimethylamminio}-2-hydroxy-1-propane sulfonate (CHAPSO), or N-dodecyl-N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET; e.g., U.S. Pat. Nos. 5,631,169; 4,868,103). A fluorophore label is selected such that a first donor molecule's emitted fluorescent energy will be absorbed by a fluorescent label on a second, 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 13245 protein to bind to a target molecule can be accomplished using real-time biomolecular interaction analysis (BIA; e.g., Sjolander et al., 1991, Anal. Chem. 63:2338–2345; Szabo et al., 1995, Curr. Opin. Struct. Biol. 5:699–705). "Surface plasmon resonance" (SPR) or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of SPR), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It can be desirable to immobilize either 13245, an anti-13245 antibody or its target molecule to facilitate separation of complexed from non-complexed forms of one or both of the proteins, as well as to accommodate automation of the assay. Binding of a test compound to a 13245 protein, or interaction of a 13245 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/13245 fusion proteins or glutathione-S-transferase/target fusion proteins can be adsorbed onto glutathione Sepharose™ beads (Sigma Chemical, St. Louis, Mo.) or glutathione-derivatized microtiter plates, which are then combined with the test compound or the test compound and either the non-adsorbed target protein or 13245 protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 13245 binding or activity determined using standard techniques.

Other techniques for immobilizing either a 13245 protein or a target molecule on matrices include using conjugation of biotin and streptavidin. Biotinylated 13245 protein or target molecules can be prepared from biotin-N-hydroxy-succinimide using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, non-reacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 13245 protein or target molecules but which do not interfere with binding of the 13245 protein to its target molecule. Such antibodies can be derivatized to the wells of the plate, and unbound target or 13245 protein trapped in the wells by antibody conjugation. Methods for detecting such complexes, in addition to those described above for the GST-immobilized complexes, include immunodetection of complexes using antibodies reactive with the 13245 protein or target molecule, as well as enzyme-linked assays which rely on detecting an enzymatic activity associated with the 13245 protein or target molecule.

Alternatively, cell free assays can be conducted in a liquid phase. In such an assay, the reaction products are separated from non-reacted components, by any of a number of standard techniques, including, but not limited to: differential centrifugation (e.g., Rivas et al., 1993, Trends Biochem. Sci. 18:284–287); chromatography (e.g., gel filtration chromatography or ion-exchange chromatography); electrophoresis (e.g., Ausubel et al., eds., 1999, Current Protocols in Molecular Biology, S. Wiley, New York); and immunoprecipitation (e.g., Ausubel, supra). Such resins and chromatographic techniques are known to one skilled in the art (e.g., Heegaard, 1998, J. Mol. Recognit. 11:141–148; Hage et al., 1997, J. Chromatogr. B Biomed. Sci. Appl. 699:499–525). Further, fluorescence energy transfer can also be conveniently utilized, as described herein, to detect binding without further purification of the complex from solution.

In a preferred embodiment, the assay includes contacting the 13245 protein or biologically active portion thereof with a known compound which binds 13245 to form an assay mixture, contacting the assay mixture with a test compound, and determining the ability of the test compound to interact with a 13245 protein, wherein determining the ability of the test compound to interact with a 13245 protein includes determining the ability of the test compound to preferentially bind to 13245 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 13245 genes herein identified. In an alternative embodiment, the invention provides methods for determining the ability of the test compound to modulate the activity of a 13245 protein through modulation of the activity of a downstream effector of a 13245 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, non-reacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from non-reacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 13245 proteins can be used as "bait proteins" in a two-hybrid assay or three-hybrid assay (e.g., U.S. Pat. No. 5,283,317; Zervos et al., 1993, Cell 72:223–232; Madura et al., 1993, J. Biol. Chem. 268:12046–12054; Bartel et al., 1993, Biotechniques 14:920–924; Iwabuchi et al., 1993, Oncogene 8:1693–1696; PCT publication number WO 94/10300), to identify other proteins, which bind to or interact with 13245 ("13245-binding proteins" or "13245-bp") and are involved in 13245 activity. Such 13245-bps can be activators or inhibitors of signals by the 13245 proteins or 13245 targets as, for example, downstream elements of a 13245-mediated signaling pathway.

The two-hybrid system is based on the modular nature of most transcription factors, which consist of separable DNA-binding and activation domains. Briefly, the assay utilizes two different DNA constructs. In one construct, the gene that codes for a 13245 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively, the 13245 protein can be fused to the activator domain). If the "bait" and the "prey" proteins are able to interact in vivo forming a 13245-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein that interacts with the 13245 protein.

In another embodiment, modulators of 13245 expression are identified. For example, a cell or cell free mixture is contacted with a candidate compound and the expression of 13245 mRNA or protein evaluated relative to the level of expression of 13245 mRNA or protein in the absence of the candidate compound. When expression of 13245 mRNA or protein is greater in the presence of the candidate compound than in its absence, the candidate compound is identified as a stimulator of 13245 mRNA or protein expression. Alternatively, when expression of 13245 mRNA or protein is less (i.e., statistically significantly less) in the presence of the candidate compound than in its absence, the candidate compound is identified as an inhibitor of 13245 mRNA or protein expression. The level of 13245 mRNA or protein expression can be determined by methods described herein for detecting 13245 mRNA or protein.

In another aspect, the invention pertains to a combination of two or more of the assays described herein. For example, a modulating agent can be identified using a cell-based or a cell free assay, and the ability of the agent to modulate the activity of a 13245 protein can be confirmed in vivo, e.g., in an animal such as an animal model for a disease.

This invention further pertains to novel agents identified by the above-described screening assays. Accordingly, it is within the scope of this invention to further use an agent identified as described herein (e.g., a 13245 modulating agent, an antisense 13245 nucleic acid molecule, a 13245-specific antibody, or a 13245-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome, e.g., to locate gene regions associated with genetic disease or to associate 13245 with a disease; (ii) identify an individual from a minute biological sample (tissue typing); and (iii) aid in forensic identification of a biological sample. These applications are described in the subsections below.

Chromosome Mapping

The 13245 nucleotide sequences or portions thereof can be used to map the location of the 13245 genes on a chromosome. This process is called chromosome mapping. Chromosome mapping is useful in correlating the 13245 sequences with genes associated with disease.

Briefly, 13245 genes can be mapped to chromosomes by preparing PCR primers (preferably 15–25 base pairs in length) from the 13245 nucleotide sequence (e.g., SEQ ID NO: 1 or SEQ ID NO: 3). These primers can then be used for PCR screening of somatic cell hybrids containing individual human chromosomes. Only those hybrids containing the human gene corresponding to the 13245 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes (D'Eustachio et al., 1983, Science 220:919–924).

Other mapping strategies e.g., in situ hybridization as described (Fan et al., 1990, Proc. Natl. Acad. Sci. USA 87:6223–6227), pre-screening with labeled flow-sorted chromosomes, and pre-selection by hybridization to chromosome specific cDNA libraries can be used to map 13245 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of FISH, see Verma et al. (1988, Human Chromosomes: A Manual of Basic Techniques, Pergamon Press, New York).

Reagents for chromosome mapping can be used individually to mark a single chromosome or a single site on that chromosome, or panels of reagents can be used for marking multiple sites and/or multiple chromosomes. Reagents corresponding to non-coding regions of the genes are typically preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), as described (e.g., Egeland et al., 1987, Nature, 325:783–787).

Moreover, differences in the DNA sequences between individuals affected and unaffected with a disease associated with the 13245 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 13245 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 13245 nucleotide sequence described herein can be used to prepare PCR primers homologous to the 5'- and 3'-ends of the sequence. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the non-coding regions. Each of the sequences described herein can, to some degree, be used as a standard against which DNA from an individual can be compared for identification purposes. Because greater numbers of polymorphisms occur in the non-coding regions, fewer sequences are necessary to differentiate individuals. The non-coding sequences of SEQ ID NO: 1 can provide positive individual identification with a panel of perhaps 10 to 1,000 primers which each yield a non-coding amplified sequence of 100 bases. If predicted coding sequences are used, such as those in SEQ ID NO: 3, a more appropriate number of primers for positive individual identification would be 500–2,000.

If a panel of reagents from 13245 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 13245 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual nucleotide sequence information can be used for identification as an accurate alternative to patterns formed by restriction enzyme generated fragments. Sequences targeted to non-coding regions of SEQ ID NO: 1 (e.g., fragments having a length of at least 20 nucleotide residues, preferably at least 30 nucleotide residues) are particularly appropriate for this use.

The 13245 nucleotide sequences described herein can further be used to provide polynucleotide reagents, e.g., labeled or label-able probes which can be used in, for example, an in situ hybridization technique, to identify a specific tissue, e.g., a tissue containing hematopoietic cells. This can be very useful in cases where a forensic pathologist is presented with a tissue of unknown origin. Panels of such 13245 probes can be used to identify tissue by species and/or by organ type.

In a similar fashion, these reagents, e.g., 13245 primers or probes can be used to screen tissue culture for contamination (i.e., to screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides a method of determining if a subject is at risk for a disorder related to a lesion in, or the malexpression of, a gene that encodes a 13245 polypeptide.

Such disorders include, e.g., a disorder associated with the malexpression of a 13245 polypeptide, e.g., an immune disorder or a neoplastic disorder.

The method includes one or more of the following:

(i) detecting, in a tissue of the subject, the presence or absence of a mutation which affects the expression of the 13245 gene, or detecting the presence or absence of a mutation in a region which controls the expression of the gene, e.g., a mutation in the 5'-control region;

(ii) detecting, in a tissue of the subject, the presence or absence of a mutation which alters the structure of the 13245 gene;

(iii) detecting, in a tissue of the subject, the malexpression of the 13245 gene at the mRNA level, e.g., detecting a non-wild-type level of a mRNA; and (iv) detecting, in a tissue of the subject, the malexpression of the gene at the protein level, e.g., detecting a non-wild-type level of a 13245 polypeptide.

In preferred embodiments the method includes: ascertaining the existence of at least one of: a deletion of one or more nucleotides from the 13245 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO: 1, or naturally occurring mutants thereof, or 5'- or 3'-flanking sequences naturally associated with the 13245 gene; (ii) exposing the probe/primer to nucleic acid of the tissue; and detecting the presence or absence of the genetic lesion by hybridization of the probe/primer to the nucleic acid, e.g., by in situ hybridization.

In preferred embodiments, detecting the malexpression includes ascertaining the existence of at least one of: an alteration in the level of a messenger RNA transcript of the 13245 gene; the presence of a non-wild-type splicing pattern of a messenger RNA transcript of the gene; or a non-wild-type level of 13245 RNA or protein.

Methods of the invention can be used for prenatal screening or to determine if a subject's offspring will be at risk for a disorder.

In preferred embodiments the method includes determining the structure of a 13245 gene, an abnormal structure being indicative of risk for the disorder.

In preferred embodiments the method includes contacting a sample form the subject with an antibody to the 13245 protein or a nucleic acid, which hybridizes specifically with the gene. These and other embodiments are discussed below.

Diagnostic and Prognostic Assays

The presence, level, or absence of 13245 protein or nucleic acid in a biological sample can be evaluated by obtaining a biological sample from a test subject and contacting the biological sample with a compound or an agent capable of detecting 13245 protein or nucleic acid (e.g., mRNA, genomic DNA) that encodes 13245 protein such that the presence of 13245 protein or nucleic acid is detected in the biological sample. The term "biological sample" includes tissues, cells and biological fluids isolated from a subject, as well as tissues, cells and fluids present within a subject. A preferred biological sample is serum. The level of expression of the 13245 gene can be measured in a number of ways, including, but not limited to:

measuring the mRNA encoded by the 13245 genes; measuring the amount of protein encoded by the 13245 genes; or measuring the activity of the protein encoded by the 13245 genes.

The level of mRNA corresponding to the 13245 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 13245 nucleic acid, such as the nucleic acid of SEQ ID NO: 1, or a portion thereof, such as an oligonucleotide of at least 7, 15, 30, 50, 100, 250 or 500 nucleotides in length and sufficient to specifically hybridize under stringent conditions to 13245 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 13245 genes.

The level of mRNA in a sample that is encoded by 13245 can be evaluated with nucleic acid amplification, e.g., by RT-PCR (U.S. Pat. No. 4,683,202), ligase chain reaction (Barany, 1991, Proc. Natl. Acad. Sci. USA 88:189–193), self-sustained sequence replication (Guatelli et al., 1990, Proc. Natl. Acad. Sci. USA 87:1874–1878), transcriptional amplification system (Kwoh et al., 1989, Proc. Natl. Acad. Sci. USA 86:1173–1177), Q-Beta Replicase (Lizardi et al., 1988, Bio/Technology 6:1197), rolling circle replication (U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5'- or 3'-regions of a 13245 gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence between the primers.

For in situ methods, a cell or tissue sample can be prepared/processed and immobilized on a support, typically a glass slide, and then contacted with a probe that can hybridize to mRNA that encodes the 13245 gene being analyzed.

In another embodiment, the methods include further contacting a control sample with a compound or agent capable of detecting 13245 mRNA, or genomic DNA, and comparing the presence of 13245 mRNA or genomic DNA in the control sample with the presence of 13245 mRNA or genomic DNA in the test sample.

A variety of methods can be used to determine the level of protein encoded by 13245. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or $F(ab')_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 13245 protein in a biological sample in vitro as well as in vivo. In vitro techniques for detection of 13245 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 13245 protein include introducing into a subject a labeled anti-13245 antibody. For example, the antibody can be labeled with a radioactive marker whose presence and location in a subject can be detected by standard imaging techniques.

In another embodiment, the methods further include contacting the control sample with a compound or agent capable of detecting 13245 protein, and comparing the presence of 13245 protein in the control sample with the presence of 13245 protein in the test sample.

The invention also includes kits for detecting the presence of 13245 in a biological sample. For example, the kit can include a compound or agent capable of detecting 13245 protein or mRNA in a biological sample, and a standard. The compound or agent can be packaged in a suitable container. The kit can further comprise instructions for using the kit to detect 13245 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably-labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein-stabilizing agent. The kit can also includes components necessary for detecting the detectable agent (e.g., an enzyme or a substrate). The kit can also contain a control sample or a series of control samples that can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with malexpressed, aberrant or unwanted 13245 expression or activity. As used herein, the term "unwanted" includes an unwanted phenomenon involved in a biological response such as induction of an inappropriate immune response or deregulated cell proliferation.

In one embodiment, a disease or disorder associated with aberrant or unwanted 13245 expression or activity is identified. A test sample is obtained from a subject and 13245 protein or nucleic acid (e.g., mRNA or genomic DNA) is evaluated, wherein the level, e.g., the presence or absence, of 13245 protein or nucleic acid is diagnostic for a subject having or at risk of developing a disease or disorder associated with aberrant or unwanted 13245 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 13245 expression or activity. For example, such methods can be used to determine whether a subject can be effectively treated with an agent that modulates 13245 expression or activity.

The methods of the invention can also be used to detect genetic alterations in a 13245 gene, thereby determining if a subject with the altered gene is at risk for a disorder characterized by misregulation in 13245 protein activity or nucleic acid expression, such as a disorder associated with tumorigenesis or induction of an inappropriate immune response. In preferred embodiments, the methods include detecting, in a sample from the subject, the presence or absence of a genetic alteration characterized by at least one of an alteration affecting the integrity of a gene encoding a 13245 protein, or the malexpression of the 13245 gene. For example, such genetic alterations can be detected by ascertaining the existence of at least one of 1) a deletion of one or more nucleotides from a 13245 gene; 2) an addition of one or more nucleotides to a 13245 gene; 3) a substitution of one or more nucleotides of a 13245 gene, 4) a chromosomal rearrangement of a 13245 gene; 5) an alteration in the level of a messenger RNA transcript of a 13245 gene, 6) aberrant modification of a 13245 gene, such as of the methylation pattern of the genomic DNA, 7) the presence of a non-wild-type splicing pattern of a messenger RNA transcript of a 13245 gene, 8) a non-wild-type level of a 13245 protein, 9) allelic loss of a 13245 gene, and 10) inappropriate post-translational modification of a 13245 protein.

An alteration can be detected without a probe/primer in a polymerase chain reaction, such as anchor PCR or RACE-PCR, or, alternatively, in a ligation chain reaction (LCR), the latter of which can be particularly useful for detecting point mutations in the 13245 gene. This method can include the steps of collecting a sample of cells from a subject, isolating nucleic acid (e.g., genomic, mRNA or both) from the sample, contacting the nucleic acid sample with one or more primers which specifically hybridize to a 13245 gene under conditions such that hybridization and amplification of the 13245 gene occurs (if present), and detecting the presence or absence of an amplification product, or detecting the size of the amplification product and comparing the length to a control sample. It is anticipated that PCR and/or LCR can be desirable to use as a preliminary amplification step in conjunction with any of the techniques used for detecting mutations described herein.

Alternative amplification methods include: self sustained sequence replication (Guatelli et al., 1990, Proc. Natl. Acad. Sci. USA 87:1874–1878), transcriptional amplification system (Kwoh et al., 1989, Proc. Natl. Acad. Sci. USA 86:1173–1177), Q-Beta Replicase (Lizardi et al., 1988, Bio/Technology 6:1197), or other nucleic acid amplification methods, followed by the detection of the amplified molecules using techniques known to those of skill in the art.

In another embodiment, mutations in a 13245 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis, and compared. Differences in fragment length sizes between sample and control DNA indicates mutations in the sample DNA. Moreover, the use of sequence specific ribozymes (e.g., U.S. Pat. No. 5,498,531) can be used to score for the presence of specific mutations by development or loss of a ribozyme cleavage site.

In other embodiments, genetic mutations in 13245 can be identified by hybridizing a sample to control nucleic acids, e.g., DNA or RNA, by, e.g., two-dimensional arrays, or, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin et al., 1996, Hum. Mutat. 7:244–255; Kozal et al., 1996, Nature Med. 2:753–759). For example, genetic mutations in 13245 can be identified in two-dimensional arrays containing light-generated DNA probes as described (Cronin et al., supra). Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 13245 gene and detect mutations by comparing the sequence of the sample 13245 with the corresponding wild-type (control) sequence. Automated sequencing procedures can be utilized when performing the diagnostic assays (1995, Biotechniques 19:448), including sequencing by mass spectrometry.

Other methods for detecting mutations in the 13245 gene include methods in which protection from cleavage agents is used to detect mismatched bases in RNA/RNA or RNA/DNA heteroduplexes (Myers et al., 1985, Science 230:1242; Cotton et al., 1988, Proc. Natl. Acad. Sci. USA 85:4597; Saleeba et al., 1992, Meth. Enzymol. 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 13245 cDNAs obtained from samples of cells. For example, the mutY enzyme of *E. coli* cleaves A at G/A mismatches and the thymidine DNA glycosylase from HeLa cells cleaves T at G/T mismatches (Hsu et al., 1994, Carcinogenesis 15:1657–1662; U.S. Pat. No. 5,459,039).

In other embodiments, alterations in electrophoretic mobility will be used to identify mutations in 13245 genes. For example, single strand conformation polymorphism (SSCP) can be used to detect differences in electrophoretic mobility between mutant and wild-type nucleic acids (Orita et al., 1989, Proc. Natl. Acad. Sci. USA 86:2766; Cotton, 1993, Mutat. Res. 285:125–144; Hayashi, 1992, Genet. Anal. Tech. Appl. 9:73–79). Single-stranded DNA fragments of sample and control 13245 nucleic acids will be denatured and allowed to re-nature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., 1991, Trends Genet 7:5).

In yet another embodiment, the movement of mutant or wild-type fragments in polyacrylamide gels containing a gradient of denaturant is assayed using denaturing gradient gel electrophoresis (DGGE) (Myers et al., 1985, Nature 313:495). When DGGE is used as the method of analysis, DNA will be modified to insure that it does not completely denature, for example by adding a GC clamp of approximately 40 base pairs of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension (Saiki et al., 1986, Nature 324:163; Saiki et al., 1989, Proc. Natl. Acad. Sci. USA 86:6230).

Alternatively, allele specific amplification technology that depends on selective PCR amplification can be used in conjunction with the instant invention. Oligonucleotides used as primers for specific amplification can carry the mutation of interest in the center of the molecule (so that amplification depends on differential hybridization; Gibbs et al., 1989, Nucl. Acids Res. 17:2437–2448) or at the extreme 3'-end of one primer where, under appropriate conditions, mismatch can prevent, or reduce polymerase extension (Prossner, 1993, Tibtech 11:238). In addition, it can be desirable to introduce a novel restriction site in the region of the mutation to create cleavage-based detection (Gasparini et al., 1992, Mol. Cell Probes 6:1). It is anticipated that in certain embodiments, amplification can also be performed using Taq ligase for amplification (Barany, 1991, Proc. Natl. Acad. Sci. USA 88:189). In such cases, ligation will occur only if there is a perfect match at the 3'-end of the 5'-sequence making it possible to detect the presence of a known mutation at a specific site by looking for the presence or absence of amplification.

The methods described herein can be performed, for example, using pre-packaged diagnostic kits comprising at least one probe nucleic acid or antibody reagent described herein, which can be conveniently used, e.g., in clinical settings to diagnose patients exhibiting symptoms or family history of a disease or illness involving a 13245 gene.

Use of 13245 Molecules as Surrogate Markers

The 13245 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 13245 molecules of the invention can be detected, and can be correlated with one or more biological states in vivo. For example, the 13245 molecules of the invention can serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers can serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease can be made using cholesterol levels as a surrogate marker, and an analysis of HIV infection can be made using HIV RNA levels as a surrogate marker, well in advance of the undesirable clinical outcomes of myocardial infarction or fully-developed AIDS). Examples of the use of surrogate markers have been described (e.g., Koomen et al., 2000, J. Mass. Spectrom. 35:258–264; James, 1994, AIDS Treat. News Arch. 209)

The 13245 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker can be indicative of the concentration of the drug in a biological tissue, in that the marker is either expressed or transcribed or not expressed or transcribed in that tissue in relationship to the level of the drug. In this fashion, the distribution or uptake of the drug can be monitored by the pharmacodynamic marker. Similarly, the presence or quantity of the pharmacodynamic marker can be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug can be sufficient to activate multiple rounds of marker (e.g., a 13245 marker) transcription or expression, the amplified marker can be in a quantity which is more readily detectable than the drug itself. Also, the marker can be more easily detected due to the nature of the marker itself; for example, using the methods described herein, anti-13245 antibodies can be employed in an immune-based detection system for a 13245 protein marker, or 13245-specific radiolabeled probes can be used to detect a 13245 mRNA marker. Furthermore, the use of a pharmacodynamic marker can offer mechanism-based prediction of risk due to drug treatment beyond the range of possible direct observations. Examples of the use of pharmacodynamic markers have been described (e.g., U.S. Pat. No. 6,033,862; Hattis et al., 1991, Env. Health Perspect. 90: 229–238; Schentag, 1999, Am. J. Health-Syst. Pharm. 56 Suppl. 3: S21–S24; Nicolau, 1999, Am, J. Health-Syst. Pharm. 56 Suppl. 3: S16–S20).

The 13245 molecules of the invention are also useful as pharmacogenomic markers. As used herein, a "pharmacogenomic marker" is an objective biochemical marker which correlates with a specific clinical drug response or susceptibility in a subject (e.g., McLeod et al., 1999, Eur. J. Cancer 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, can be selected. For example, based on the presence or quantity of RNA, or protein (e.g., 13245 protein or RNA) for specific tumor markers in a subject, a drug or course of treatment can be selected that is optimized for the treatment of the specific tumor likely to be present in the subject. Similarly, the presence or absence of a specific sequence mutation in 13245 DNA can correlate 13245 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-13245 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamninetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including an agent in the composition that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents and/or adjuvant materials can be included as part of the composition. The tablets, pills, capsules, troches and the like can contain any of the following ingredients, or compounds of a similar nature: a binder, such as microcrystalline cellulose, gum tragacanth or gelatin; an excipient, such as starch or lactose; a disintegrating agent, such as alginic acid, Primogel™, or corn starch; a lubricant, such as magnesium stearate or Sterotes™; a glidant, such as colloidal silicon dioxide; a sweetening agent, such as sucrose or saccharin; or a flavoring agent, such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells using monoclonal antibodies directed towards viral antigens) can also be used as pharmaceutically acceptable carriers. These can be prepared according to described methods (e.g., U.S. Pat. No. 4,522,811).

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 milligrams per kilogram body weight, preferably about 0.01 to 25 milligrams per kilogram body weight, more preferably about 0.1 to 20 milligrams per kilogram body weight, and even more preferably about 1 to 10 milligrams per kilogram, 2 to 9 milligrams per kilogram, 3 to 8 milligrams per kilogram, 4 to 7 milligrams per kilogram, or 5 to 6 milligrams per kilogram body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 milligrams per kilogram of body weight (generally 10 to 20 milligrams per kilogram). If the antibody is to act in the brain, a dosage of 50 to 100 milligrams per kilogram is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for the lipidation of antibodies is described by Cruikshank et al. (1997, J. AIDS Hum. Retrovir. 14:193).

The present invention encompasses agents that modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including hetero-organic and organo-metallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) can be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, and the drug moiety is not to be construed as limited to classical chemical therapeutic agents. For example, the drug moiety can be a protein or polypeptide possessing a desired biological activity. Such proteins can include, for example, a toxin such as abrin, ricin A, gelonin, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukins-1, -2, and -6, granulocyte macrophage colony stimulating factor, granulocyte colony stimulating factor, or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (e.g., Chen et al., 1994, Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 13245 expression or activity. With regards to both prophylactic and therapeutic methods of treatment, such treatments can be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype".) Thus, another aspect of the invention provides methods for tailoring an individual's prophylactic or therapeutic treatment with either the 13245 molecules of the present invention or 13245 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Treatment is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

A therapeutic agent includes, but is not limited to, small molecules, peptides, antibodies, ribozymes and antisense oligonucleotides.

In one aspect, the invention provides a method for preventing a disease or condition in a subject associated with an aberrant or unwanted 13245 expression or activity, by administering to the subject a 13245 or an agent which modulates 13245 expression, or at least one 13245 activity. Subjects at risk for a disease which is caused or contributed to by aberrant or unwanted 13245 expression or activity can be identified by, for example, any or a combination of diagnostic or prognostic assays as described herein. Administration of a prophylactic agent can occur prior to the manifestation of symptoms characteristic of the 13245 aberrance, such that a disease or disorder is prevented or, alternatively, delayed in its progression. Depending on the type of 13245 aberrance, for example, a 13245 protein, 13245 agonist or 13245 antagonist agent can be used for treating the subject. The appropriate agent can be determined based on screening assays described herein.

It is possible that some 13245 disorders can be caused, at least in part, by an abnormal level of gene product, or by the presence of a gene product exhibiting abnormal activity. As such, the reduction in the level and/or activity of such gene products would bring about the amelioration of disorder symptoms As discussed, successful treatment of 13245 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 13245 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, $F(ab')_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity Another method by which nucleic acid molecules can be utilized in treating or preventing a disease characterized by 13245 expression is through the use of aptamer molecules specific for 13245 protein. Aptamers are nucleic acid molecules having a tertiary structure that permits them to specifically bind to protein ligands (e.g., Osborne et al., 1997, Curr. Opin. Chem. Biol. 1:5–9; Patel, 1997, Curr. Opin. Chem. Biol. 1:32–46). Since nucleic acid molecules can in many cases be more conveniently introduced into target cells than therapeutic protein molecules can be, aptamers offer a method by which 13245 protein activity can be specifically decreased without the introduction of drugs or other molecules which can have pluripotent effects.

Antibodies can be generated that are both specific for target gene product and that reduce target gene product activity. Such antibodies may, therefore, by administered in instances whereby negative modulatory techniques are appropriate for the treatment of 13245 disorders.

In circumstances wherein injection of an animal or a human subject with a 13245 protein or epitope for stimulating antibody production is harmful to the subject, it is possible to generate an immune response against 13245 through the use of anti-idiotypic antibodies (e.g., Herlyn, 1999, Ann. Med. 31:66–78; Bhattacharya-Chatteijee et al., 1998, Cancer Treat. Res. 94:51–68). If an anti-idiotypic antibody is introduced into a mammal or human subject, it should stimulate the production of anti-anti-idiotypic antibodies, which should be specific to the 13245 protein. Vaccines directed to a disease characterized by 13245 expression can also be generated in this fashion.

In instances where the target antigen is intracellular and whole antibodies are used, internalizing antibodies can be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (e.g., Marasco et al., 1993, Proc. Natl. Acad. Sci. USA 90:7889–7893).

The identified compounds that inhibit target gene expression, synthesis and/or activity can be administered to a patient at therapeutically effective doses to prevent, treat or ameliorate 13245 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of “free” and “bound” compound in the serum of the test subject. Such assays can utilize antibody mimics and/or “biosensors” that have been created through molecular imprinting techniques. The compound which is able to modulate 13245 activity is used as a template, or “imprinting molecule,” to spatially organize polymerizable monomers prior to their polymerization with catalytic reagents. The subsequent removal of the imprinted molecule leaves a polymer matrix that contains a repeated “negative image” of the compound and is able to selectively rebind the molecule under biological assay conditions. Detailed reviews of this technique appear in the art (Ansell et al., 1996, Curr. Opin. Biotechnol. 7:89–94; Shea, 1994, Trends Polymer Sci. 2:166–173). Such “imprinted” affinity matrixes are amenable to ligand-binding assays, whereby the immobilized monoclonal antibody component is replaced by an appropriately imprinted matrix (e.g., a matrix described in Vlatakis et al., 1993, Nature 361:645–647. Through the use of isotope-labeling, the “free” concentration of compound which modulates the expression or activity of 13245 can be readily monitored and used in calculations of $IC_{50}$.

Such “imprinted” affinity matrixes can also be designed to include fluorescent groups whose photon-emitting properties measurably change upon local and selective binding of target compound. These changes can be readily assayed in real time using appropriate fiber optic devices, in turn allowing the dose in a test subject to be quickly optimized based on its individual $IC_{50}$. A rudimentary example of such a “biosensor” is discussed in Kriz et al. (1995, Anal. Chem. 67:2142–2144).

Another aspect of the invention pertains to methods of modulating 13245 expression or activity for therapeutic purposes. Accordingly, in an exemplary embodiment, the modulatory method of the invention involves contacting a cell with a 13245 or agent that modulates one or more of the activities of 13245 protein activity associated with the cell. An agent that modulates 13245 protein activity can be an agent as described herein, such as a nucleic acid or a protein, a naturally-occurring target molecule of a 13245 protein (e.g., a 13245 substrate or receptor), a 13245 antibody, a 13245 agonist or antagonist, a peptidomimetic of a 13245 agonist or antagonist, or other small molecule.

In one embodiment, the agent stimulates one or 13245 activities. Examples of such stimulatory agents include active 13245 protein and a nucleic acid molecule encoding 13245. In another embodiment, the agent inhibits one or more 13245 activities. Examples of such inhibitory agents include antisense 13245 nucleic acid molecules, anti-13245 antibodies, and 13245 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 13245 protein or nucleic acid molecule. In one embodiment, the method involves administering an agent (e.g., an agent identified by a screening assay described herein), or combination of agents that modulates (e.g., up-regulates or down-regulates) 13245 expression or activity. In another embodiment, the method involves administering a 13245 protein or nucleic acid molecule as therapy to compensate for reduced, aberrant, or unwanted 13245 expression or activity.

Stimulation of 13245 activity is desirable in situations in which 13245 is abnormally down-regulated and/or in which increased 13245 activity is likely to have a beneficial effect. For example, stimulation of 13245 activity is desirable in situations in which a 13245 is down-regulated and/or in which increased 13245 activity is likely to have a beneficial effect. Likewise, inhibition of 13245 activity is desirable in situations in which 13245 is abnormally up-regulated and/or in which decreased 13245 activity is likely to have a beneficial effect.

Pharmacogenomics

The 13245 molecules of the present invention, as well as agents, or modulators which have a stimulatory or inhibitory effect on 13245 activity (e.g., 13245 gene expression) as identified by a screening assay described herein can be administered to individuals to treat (prophylactically or therapeutically) 13245-associated disorders associated with aberrant or unwanted 13245 activity (e.g., disorders associated with tumorigenesis or induction of an inappropriate immune response). In conjunction with such treatment, pharmacogenomics (i.e., the study of the relationship between an individual’s genotype and that individual’s response to a foreign compound or drug) can be considered.

Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a 13245 molecule or 13245 modulator as well as tailoring the dosage and/or therapeutic regimen of treatment with a 13245 molecule or 13245 modulator.

Pharmacogenomics deals with clinically significant hereditary variations in the response to drugs due to altered drug disposition and abnormal action in affected persons (e.g., Eichelbaum et al., 1996, Clin. Exp. Pharmacol. Physiol. 23:983–985; Linder et al., 1997, Clin. Chem. 43:254–266). In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is hemolysis after ingestion of oxidant drugs (anti-malarials, sulfonamides, analgesics, nitrofurans) and consumption of fava beans.

One pharmacogenomics approach to identifying genes that predict drug response, known as "a genome-wide association," relies primarily on a high-resolution map of the human genome consisting of already known gene-related markers (e.g., a "bi-allelic" gene marker map which consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP can be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that can be common among such genetically similar individuals.

Alternatively, a method termed the "candidate gene approach" can be utilized to identify genes that predict drug response. According to this method, if a gene that encodes a drug's target is known (e.g., a 13245 protein of the present invention), all common variants of that gene can be fairly easily identified in the population and it can be determined if having one version of the gene versus another is associated with a particular drug response.

Alternatively, a method termed "gene expression profiling," can be utilized to identify genes that predict drug response. For example, the gene expression of an animal dosed with a drug (e.g., a 13245 molecule or 13245 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 13245 molecule or 13245 modulator, such as a modulator identified by one of the exemplary screening assays described herein.

The present invention further provides methods for identifying new agents, or combinations, that are based on identifying agents that modulate the activity of one or more of the gene products encoded by one or more of the 13245 genes of the present invention, wherein these products can be associated with resistance of the cells to a therapeutic agent. Specifically, the activity of the proteins encoded by the 13245 genes of the present invention can be used as a basis for identifying agents for overcoming agent resistance. By blocking the activity of one or more of the resistance proteins, target cells, e.g., cells of the immune system, will become sensitive to treatment with an agent that the unmodified target cells were resistant to.

Monitoring the influence of agents (e.g., drugs) on the expression or activity of a 13245 protein can be applied in clinical trials. For example, the effectiveness of an agent determined by a screening assay as described herein to increase 13245 gene expression, protein levels, or up-regulate 13245 activity, can be monitored in clinical trials of subjects exhibiting decreased 13245 gene expression, protein levels, or down-regulated 13245 activity. Alternatively, the effectiveness of an agent determined by a screening assay to decrease 13245 gene expression, protein levels, or down-regulate 13245 activity, can be monitored in clinical trials of subjects exhibiting increased 13245 gene expression, protein levels, or up-regulated 13245 activity. In such clinical trials, the expression or activity of a 13245 gene, and preferably, other genes that have been implicated in, for example, a 13245-associated disorder can be used as a "read out" or markers of the phenotype of a particular cell.

Other Embodiments

In another aspect, the invention features, a method of analyzing a plurality of capture probes. The method can be used, e.g., to analyze gene expression. The method includes: providing a two-dimensional array having a plurality of addresses, each address of the plurality being positionally distinguishable from each other address of the plurality, and each address of the plurality having a unique capture probe, e.g., a nucleic acid or peptide sequence; contacting the array with a 13245, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 13245 nucleic acid, polypeptide, or antibody.

The capture probes can be a set of nucleic acids from a selected sample, e.g., a sample of nucleic acids derived from a control or non-stimulated tissue or cell.

The method can include contacting the 13245 nucleic acid, polypeptide, or antibody with a first array having a plurality of capture probes and a second array having a different plurality of capture probes. The results of hybridization can be compared, e.g., to analyze differences in expression between a first and second sample. The first plurality of capture probes can be from a control sample, e.g., a wild-type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 13245. Such methods can be used to diagnose a subject, e.g., to evaluate risk for a disease or disorder, to evaluate suitability of a selected treatment for a subject, to evaluate whether a subject has a disease or disorder. 13245 is associated with protein phosphorylation, thus it is useful for evaluating disorders relating to aberrant protein phosphorylation, such as tumorigenesis and inappropriate cell signaling.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 13245 or from a cell or subject in which a 13245 mediated response has been elicited, e.g., by contact of the cell with 13245 nucleic acid or protein, or administration to the cell or subject 13245 nucleic acid or protein; contacting the array with one or more inquiry probe, wherein an inquiry probe can be a nucleic acid, polypeptide, or antibody (which is preferably other than 13245 nucleic acid, polypeptide, or antibody); providing a two-dimensional array having a plurality of addresses, each address of the plurality being positionally distinguishable from each other address of the plurality, and each address of the plurality having a unique capture probe, e.g., wherein the capture probes are from a cell or subject which does not express 13245 (or does not express as highly as in the case of the 13245 positive plurality of capture probes) or from a cell or subject which in which a 13245 mediated response has not been elicited (or has been elicited to a lesser extent than in the first sample); contacting the array with one or more inquiry probes (which is preferably other than a 13245 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing a plurality of probes or a sample. The method is useful, e.g., for analyzing gene expression. The method includes:

providing a two dimensional array having a plurality of addresses, each address of the plurality being positionally distinguishable from each other address of the plurality having a unique capture probe, contacting the array with a first sample from a cell or subject which express or malexpress 13245 or from a cell or subject in which a 13245-mediated response has been elicited, e.g., by contact of the cell with 13245 nucleic acid or protein, or administration to the cell or subject 13245 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 13245 (or does not express as highly as in the case of the 13245 positive plurality of capture probes) or from a cell or subject which in which a 13245 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 13245, e.g., analyzing structure, function, or relatedness to other nucleic acid or amino acid sequences. The method includes: providing a 13245 nucleic acid or amino acid sequence, e.g., nucleotide sequence from 13245 or a portion thereof; comparing the 13245 sequence with one or more preferably a plurality of sequences from a collection of sequences, e.g., a nucleic acid or protein sequence database; to thereby analyze 13245.

The method can include evaluating the sequence identity between a 13245 sequence and a database sequence. The method can be performed by accessing the database at a second site, e.g., via the internet.

In another aspect, the invention features, a set of oligonucleotides, useful, e.g., for identifying SNPs, or identifying specific alleles of 13245. The set includes a plurality of oligonucleotides, each of which has a different nucleotide at an interrogation position, e.g., an SNP or the site of a mutation. In a preferred embodiment, the plurality of oligonucleotides are identical in sequence with one another (except for differences in length). The oligonucleotides can be provided with differential labels, such that an oligonucleotide that hybridizes to one allele provides a signal that is distinguishable from an oligonucleotide that hybridizes to a second allele.

The sequence of a 13245 molecules is provided in a variety of mediums to facilitate use thereof. A sequence can be provided as a manufacture, other than an isolated nucleic acid or amino acid molecule, which contains a 13245. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form.

A 13245 nucleotide or amino acid sequence can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect™ and Microsoft Word™, or represented in the form of an ASCII file, stored in a database application, such as DB2, Sybase™, Oracle™, or the like. The skilled artisan can readily adapt any number of data processor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention that match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, can be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBIA).

Thus, the invention features a method of making a computer readable record of a sequence of a 13245 sequence that includes recording the sequence on a computer readable matrix. In a preferred embodiment, the record includes one or more of the following: identification of an open reading frame; identification of a domain, region, or site; identification of the start of transcription; identification of the transcription terminator; the full length amino acid sequence of the protein, or a mature form thereof; the 5'-end of the translated region; or 5'- and/or 3'-regulatory regions.

In another aspect, the invention features, a method of analyzing a sequence. The method includes: providing a 13245 sequence or record, in computer readable form; comparing a second sequence to the gene name sequence; thereby analyzing a sequence. Comparison can include comparing to sequences for sequence identity or determining if one sequence is included within the other, e.g., determining if the 13245 sequence includes a sequence being compared. In a preferred embodiment, the 13245 or second sequence is stored on a first computer, e.g., at a first site and the comparison is performed, read, or recorded on a second computer, e.g., at a second site. E.g., the 13245 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5'-end of the translated region; or 5'- and/or 3'-regulatory regions.

This invention is further illustrated by the following examples that should not be construed as limiting. The contents of all references, patents and published patent applications cited throughout this application are incorporated herein by reference.

EXAMPLES

Example 1

Identification and Characterization of Human 13245 cDNA

The human 13245 nucleotide sequence (FIG. 1; SEQ ID NO: 1), which is approximately 6575 nucleotides in length including non-translated regions, contains a predicted methionine-initiated coding sequence at about nucleotide residues 19–6178. The coding sequence encodes a 2053 amino acid protein (SEQ ID NO: 2).

Example 2

Tissue Distribution of 13245 mRNA

Northern blot hybridizations with various RNA samples can be performed under standard conditions and washed under stringent conditions, i.e., 0.2×SSC at 65° C. A DNA probe corresponding to all or a portion of the 13245 cDNA (SEQ ID NO: 1) can be used. The DNA can, for example, be radioactively labeled with $^{32}$P-dCTP using the Prime-It™ Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb™ hybridization solution (Clontech) and washed at high stringency according to manufacturer's recommendations.

Example 3

Recombinant Expression of 13245 in Bacterial Cells

In this example, 13245 is expressed as a recombinant glutathione-S-transferase (GST) fusion polypeptide in *E. coli* and the fusion polypeptide is isolated and characterized. Specifically, 13245 nucleic acid sequences are fused to GST nucleic acid sequences and this fusion construct is expressed in *E. coli*, e.g., strain PEB199. Expression of the GST-13245 fusion construct in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant 13245 Protein in COS Cells

To express the 13245 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 13245 protein and an HA tag (Wilson et al., 1984, Cell 37:767) or a FLAG® tag fused in-frame to its 3'-end of the fragment is cloned into the polylinker region of the vector, thereby placing the expression of the recombinant protein under the control of the CMV promoter.

To construct the plasmid, the 13245 DNA sequence is amplified by PCR using two primers. The 5' primer contains the restriction site of interest followed by approximately twenty nucleotides of the 13245 coding sequence starting from the initiation codon; the 3'-end sequence contains complementary sequences to the other restriction site of interest, a translation stop codon, the HA tag or FLAG® tag and the last 20 nucleotides of the 13245 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 13245 gene is inserted in the desired orientation. The ligation mixture is transformed into *E. coli* cells (strains HB101, DH5alpha, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 13245-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook et al., (1989, Molecular Cloning: A Laboratory Manual. 2nd ed., Cold Spring Harbor Laboratory Press, Cold Spring Harbor, N.Y.). The expression of the 13245 polypeptide is detected by radiolabeling ($^{35}$S-methionine or $^{35}$S-cysteine, available from NEN, Boston, Mass., can be used) and immunoprecipitation (Harlow et al., 1988, Antibodies: A Laboratory Manual, Cold Spring Harbor Laboratory Press, Cold Spring Harbor, N.Y.) using an HA-specific monoclonal antibody. Briefly, the cells are labeled for 8 hours with $^{35}$S-methionine (or $^{35}$S-cysteine). The culture media are then collected and the cells are lysed using detergents (RIPA buffer, 150 millimolar NaCl, 1% NP-40, 0.1% SDS, 0.5% DOC, 50 millimolar Tris, pH 7.5). Both the cell lysate and the culture media are precipitated with an HA-specific monoclonal antibody. Precipitated polypeptides are then analyzed by SDS-PAGE.

Alternatively, DNA containing the 13245 coding sequence is cloned directly into the polylinker of the pcDNA/Amp vector using the appropriate restriction sites. The resulting plasmid is transfected into COS cells in the manner described above, and the expression of the 13245 polypeptide is detected by radiolabeling and immunoprecipitation using a 13245-specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule selected from the group consisting of:

a) a nucleic acid molecule comprising a nucleotide sequence which is at least 95% identical to the nucleotide sequence of either of SEQ ID NOs: 1 and 3, wherein the polypetide encoded by the nucleic acid molecule has kinase activity;

b) a nucleic acid molecule comprising a fragment of at least 1400 nucleotides of the nucleotide sequence of either of SEQ ID NOs: 1 and 3, wherein the polypeptide encoded by the nucleic acid molecule has kinase activity;

c) a nucleic acid molecule which encodes a polypeptide comprising the amino acid sequence of SEQ ID NO: 2; and d) a nucleic acid molecule which encodes a fragment of a polypeptide comprising the amino acid sequence of SEQ ID NO: 2, wherein the fragment comprises at least 1000 contiguous amino acids of SEQ ID NO: 2, wherein the fragment has kinase activity.

2. The isolated nucleic acid molecule of claim 1, which is selected from the group consisting of:

a) a nucleic acid comprising the nucleotide sequence of either of SEQ ID NOs: 1 and 3; and b) a nucleic acid molecule which encodes a polypeptide comprising the amino acid sequence of SEQ ID NO: 2.

3. The nucleic acid molecule of claim 1 further comprising a vector nucleic acid sequence.

4. The nucleic acid molecule of claim 1 further comprising a nucleic acid sequence encoding a heterologous polypeptide.

5. A host cell that contains the nucleic acid molecule of claim 1.

6. The host cell of claim 5, wherein the host cell is a mammalian host cell.

7. A non-human mammalian host cell containing the nucleic acid molecule of claim 1.

8. A method for producing a polypeptide selected from the group consisting of:

a) a polypeptide comprising the amino acid sequence of SEQ ID NO: 2; and b) a polypeptide comprising a fragment of the amino acid sequence of SEQ ID NO: 2, wherein the fragment comprises at least 1000 contiguous amino acids of SEQ ID NO: 2, wherein the fragment has kinase activity;

the method comprising culturing the host cell of claim 5 under conditions in which the nucleic acid molecule is expressed.

9. A kit comprising the molecule of claim 1 and instructions for use.

* * * * *

SEQUENCE LISTING

<160> NUMBER OF SEQ ID NOS: 7

<210> SEQ ID NO 1
<211> LENGTH: 6574
<212> TYPE: DNA
<213> ORGANISM: Homo sapiens

<400> SEQUENCE: 1
agagccgcca gtggggagat gttgaagttc aaatatggag cgcggaatcc tttggatgct 60
ggtgctgctg aacccattgc cagccgggcc tccaggctga atctgttctt ccaggggaaa 120
ccacccttta tgactcaaca gcagatgtct cctctttccc gagaagggat attagatgcc 180
ctctttgttc tctttgaaga atgcagtcag cctgctctga tgaagattaa gcacgtgagc 240
aactttgtcc ggaagtattc cgacaccata gctgagttac aggagctcca gccttcggca 300
aaggacttcg aagtcagaag tcttgtaggt tgtggtcact ttgctgaagt gcaggtggta 360
agagagaaag caaccgggga catctatgct atgaaagtga tgaagaagaa ggctttattg 420
gcccaggagc aggtttcatt ttttgaggaa gagcggaaca tattatctcg aagcacaagc 480
ccgtggatcc cccaattaca gtatgccttt caggacaaaa atcaccttta tctgatggag 540
gaatatcagc ctggagggga cttgctgtca cttttgaata gatatgagga ccagttagat 600
gaaaacctga tacagtttta cctagctgag ctgattttgg ctgttcacag cgttcatctg 660
atgggatacg tgcatcgaga catcaagcct gagaacattc tcgttgaccg cacaggacac 720
atcaagctgg tggattttgg atctgccgcg aaaatgaatt caaacaagat ggtgaatgcc 780
aaactcccga ttgggacccc agattacatg gctcctgaag tgctgactgt gatgaacggg 840
gatggaaaag gcacctacgg cctggactgt gactggtggt cagtgggcgt gattgcctat 900
gagatgattt atgggagatc cccottcgca gagggaacct ctgccagaac cttcaataac 960

-continued

```
attatgaatt tccagcggtt tttgaaattt ccagatgacc ccaaagtgag cagtgacttt   1020
cttgatctga ttcaaagctt gttgtgcggc cagaaagaga gactgaagtt tgaaggtctt   1080
tgctgccatc ctttcttctc taaaattgac tggaacaaca ttcgtaactc tcctcccccc   1140
ttcgttccca ccctcaagtc tgacgatgac acctccaatt ttgatgaacc agagaagaat   1200
tcgtgggttt catcctctcc gtgccagctg agcccctcag gcttctcggg tgaagaactg   1260
ccgtttgtgg ggttttcgta cagcaaggca ctggggattc ttggtagatc tgagtctgtt   1320
gtgtcgggtc tggactcccc tgccaagact agctccatgg aaaagaaact tctcatcaaa   1380
agcaaagagc tacaagactc tcaggacaag tgtcacaaga tggagcagga aatgacccgg   1440
ttacatcgga gagtgtcaga ggtggaggct gtgcttagtc agaaggaggt ggagctgaag   1500
gcctctgaga ctcagagatc cctcctggag caggaccttg ctacctacat cacagaatgc   1560
agtagcttaa agcgaagttt ggagcaagca cggatggagg tgtcccagga ggatgacaaa   1620
gcactgcagc ttctccatga tatcagagag cagagccgga agctccaaga aatcaaagag   1680
caggagtacc aggctcaagt ggaagaaatg aggttgatga tgaatcagtt ggaagaggat   1740
cttgtctcag caagaagacg gagtgatctc tacgaatctg agctgagaga gtctcggctt   1800
gctgctgaag aattcaagcg gaaagcgaca gaatgtcagc ataaactgtt gaaggctaag   1860
gatcaaggga agcctgaagt gggagaatat gcgaaactgg agaagatcaa tgctgagcag   1920
cagctcaaaa ttcaggagct ccaagagaaa ctggagaagg ctgcaaagga gcgagccgag   1980
agggagctgg agaagctgca gaaccgagag gattcttctg aaggcatcag aaagaagctg   2040
gtggaagctg aggaacgccg ccattctctg gagaacaagg taaagagact agagaccatg   2100
gagcgtagag aaaacagact gaaggatgac atccagacaa aatcccaaca gatccagcag   2160
atggctgata aaattctgga gctcgaagag aaacatcggg aggcccaagt ctcagcccag   2220
cacctagaag tgcacctgaa acagaaagag cagcactatg aggaaaagat taaagtgttg   2280
gacaatcaga taaagaaaga cctggctgac aaggagacac tggagaacat gatgcagaga   2340
cacgaggagg aggcccatga gaagggcaaa attctcagcg aacagaaggc gatgatcaat   2400
gctatggatt ccaagatcag atccctggaa cagaggattg tggaactgtc tgaagccaat   2460
aaacttgcag caaatagcag tctttttacc caaaggaaca tgaaggccca agaagagatg   2520
atttctgaac tcaggcaaca gaaattttac ctggagacac aggctgggaa gttggaggcc   2580
cagaaccgaa aactggagga gcagctggag aagatcagcc accaagacca cagtgacaag   2640
aatcggctgc tggaactgga gacaagattg cgggaggtca gtctagagca cgaggagcag   2700
aaactggagc tcaagcgcca gctcacagag ctacagctct ccctgcagga gcgcgagtca   2760
cagttgacag ccctgcaggc tgcacgggcg gccctggaga gccagcttcg ccaggcgaag   2820
acagagctgg aagagaccac agcagaagct gaagaggaga tccaggcact cacggcacat   2880
agagatgaaa tccagcgcaa atttgatgct cttcgtaaca gctgtactgt aatcacagac   2940
ctggaggagc agctaaacca gctgaccgag gacaacgctg aactcaacaa ccaaaacttc   3000
tacttgtcca aacaactcga tgaggcttct ggcgccaacg acgagattgt acaactgcga   3060
agtgaagtgg accatctccg ccgggagatc acggaacgag agatgcagct taccagccag   3120
aagcaaacga tggaggctct gaagaccacg tgcaccatgc tggaggaaca ggtcatggat   3180
ttggaggccc taaacgatga gctgctagaa aaagagcggc agtgggaggc ctggaggagc   3240
gtcctgggtg atgagaaatc ccagtttgag tgtcgggttc gagagctgca gagaatgctg   3300
```

-continued

```
gacaccgaga aacagagcag ggcgagagcc gatcagcgga tcaccgagtc tcgccaggtg   3360
gtggagctgg cagtgaagga gcacaaggct gagattctcg ctctgcagca ggctctcaaa   3420
gagcagaagc tgaaggccga gagcctctct gacaagctca atgacctgga gaagaagcat   3480
gctatgcttg aaatgaatgc ccgaagctta cagcagaagc tggagactga acgagagctc   3540
aaacagaggc ttctggaaga gcaagccaaa ttacagcagc agatggacct gcagaaaaat   3600
cacattttcc gtctgactca aggactgcaa gaagctctag atcgggctga tctactgaag   3660
acagaaagaa gtgacttgga gtatcagctg gaaaacattc aggttctcta ttctcatgaa   3720
aaggtgaaaa tggaaggcac tatttctcaa caaaccaaac tcattgattt tctgcaagcc   3780
aaaatggacc aacctgctaa aaagaaaaag ggtttattta gtcgacggaa agaggaccct   3840
gctttaccca cacaggttcc tctgcagtac aatgagctga agctggccct ggagaaggag   3900
aaagctcgct gtgcagagct agaggaagcc cttcagaaga cccgcatcga gctccggtcc   3960
gcccgggagg aagctgccca ccgcaaagca acggaccacc cacacccatc cacgccagcc   4020
accgcgaggc agcagatcgc catgtccgcc atcgtgcggt cgccagagca ccagcccagt   4080
gccatgagcc tgctggcccc gccatccagc cgcagaaagg agtcttcaac tccagaggaa   4140
tttagtcggc gtcttaagga acgcatgcac cacaatattc ctcaccgatt caacgtagga   4200
ctgaacatgc gagccacaaa gtgtgctgtg tgtctggata ccgtgcactt tggacgccag   4260
gcatccaaat gtctcgaatg tcaggtgatg tgtcacccca agtgctccac gtgcttgcca   4320
gccacctgcg gcttgcctgc tgaatatgcc acacacttca ccgaggcctt ctgccgtgac   4380
aaaatgaact ccccaggtct ccagaccaag gagcccagca gcagcttgca cctggaaggg   4440
tggatgaagg tgcccaggaa taacaaacga ggacagcaag gctgggacag gaagtacatt   4500
gtcctggagg gatcaaaagt cctcatttat gacaatgaag ccagagaagc tggacagagg   4560
ccggtggaag aatttgagct gtgccttccc gacggggatg tatctattca tggtgccgtt   4620
ggtgcttccg aactcgcaaa tacagccaaa gcagaaaaag cagaagctga tgctaaactg   4680
cttggaaact ccctgctgaa actggaaggt gatgaccgtc tagacatgaa ctgcacgctg   4740
cccttcagtg accaggtggt gttggtgggc accgaggaag ggctctacgc cctgaatgtc   4800
ttgaaaaact ccctaaccca tgtcccagga attggagcag tcttccaaat ttatattatc   4860
aaggacctgg agaagctact catgatagca ggagaagagc gggcactgtg tcttgtggac   4920
gtgaagaaag tgaaacagtc cctggcccag tcccacctgc ctgcccagcc cgacatctca   4980
cccaacattt ttgaagctgt caagggctgc cacttgtttg gggcaggcaa gattgagaac   5040
gggctctgca tctgtgcagc catgcccagc aaagtcgtca ttctccgcta caacgaaaac   5100
ctcagcaaat actgcatccg gaaagagata gagacctcag agccctgcag ctgtatccac   5160
ttcaccaatt acagtatcct cattggaacc aataaattct acgaaatcga catgaagcag   5220
tacacgctcg aggaattcct ggataagaat gaccattcct tggcacctgc tgtgtttgcc   5280
gcctcttcca acagcttccc tgtctcaatc gtgcaggtga acagcgcagg gcagcgagag   5340
gagtacttgc tgtgtttcca cgaatttgga gtgttcgtgg attcttacgg aagacgtagc   5400
cgcacagacg atctcaagtg gagtcgctta cctttggcct ttgcctacag agaaccctat   5460
ctgtttgtga cccacttcaa ctcactcgaa gtaattgaga tccaggcacg ctcctcagca   5520
gggacccctg cccgagcgta cctggacatc ccgaacccgc gctacctggg ccctgccatt   5580
tcctcaggag cgatttactt ggcgtcctca taccaggata aattaagggt catttgctgc   5640
aagggaaacc tcgtgaagga gtccggcact gaacaccacc ggggcccgtc cacctcccgc   5700
```

```
agcagcccca acaagcgagg cccacccacg tacaacgagc acatcaccaa gcgcgtggcc   5760

tccagcccag cgccgcccga aggccccagc cacccgcgag agccaagcac accccaccgc   5820

taccgcgagg ggcggaccga gctgcgcagg gacaagtctc ctggccgccc cctggagcga   5880

gagaagtccc ccggccggat gctcagcacg cggagagagc ggtcccccgg gaggctgttt   5940

gaagacagca gcaggggccg gctgcctgcg ggagccgtga ggaccccgct gtcccaggtg   6000

aacaagggaa gagggcagag tgcctctcaa gttttcacgg ttaacactgt cacctattat   6060

gactggaata aaaagctgga caacctgcca gctaactggt cagtcctgag gatcatccag   6120

ctgaatggag aaatccggca gcaggttgaa aagtctgttc tgagaacaga ttattgctga   6180

gcagagttca tgtgacttct agacgtggtg acttaaaaaa tggccttaag gctgcagagc   6240

cagccacctc tgcttacaaa aagagtactt agtgcacatg actgtaagaa acaattgtaa   6300

aacctcatct agaaatcaga aagcttctaa tttctataga aatgacacct ccctggagcc   6360

gagagacaat ctgttgttga ttttgaagga caggcaagac caacactgta tttagttcca   6420

tagccaggcc tcaacaggga caagtggctg gccttaaaaa cacacagatg actggaaatg   6480

atgtgtggcc tcagtccctg tttcccagaa ttttactggc aaaggagtta gcattcattt   6540

ttggcttaag aaaaatcgag aatgtaggtt taga                                 6574
```

<210> SEQ ID NO 2
<211> LENGTH: 2053
<212> TYPE: PRT
<213> ORGANISM: Homo sapiens

<400> SEQUENCE: 2

```
Met Leu Lys Phe Lys Tyr Gly Ala Arg Asn Pro Leu Asp Ala Gly Ala
  1               5                  10                  15

Ala Glu Pro Ile Ala Ser Arg Ala Ser Arg Leu Asn Leu Phe Phe Gln
             20                  25                  30

Gly Lys Pro Pro Phe Met Thr Gln Gln Gln Met Ser Pro Leu Ser Arg
         35                  40                  45

Glu Gly Ile Leu Asp Ala Leu Phe Val Leu Phe Glu Glu Cys Ser Gln
     50                  55                  60

Pro Ala Leu Met Lys Ile Lys His Val Ser Asn Phe Val Arg Lys Tyr
 65                  70                  75                  80

Ser Asp Thr Ile Ala Glu Leu Gln Glu Leu Gln Pro Ser Ala Lys Asp
                 85                  90                  95

Phe Glu Val Arg Ser Leu Val Gly Cys Gly His Phe Ala Glu Val Gln
            100                 105                 110

Val Val Arg Glu Lys Ala Thr Gly Asp Ile Tyr Ala Met Lys Val Met
        115                 120                 125

Lys Lys Lys Ala Leu Leu Ala Gln Glu Gln Val Ser Phe Phe Glu Glu
    130                 135                 140

Glu Arg Asn Ile Leu Ser Arg Ser Thr Ser Pro Trp Ile Pro Gln Leu
145                 150                 155                 160

Gln Tyr Ala Phe Gln Asp Lys Asn His Leu Tyr Leu Met Glu Glu Tyr
                165                 170                 175

Gln Pro Gly Gly Asp Leu Leu Ser Leu Leu Asn Arg Tyr Glu Asp Gln
            180                 185                 190

Leu Asp Glu Asn Leu Ile Gln Phe Tyr Leu Ala Glu Leu Ile Leu Ala
        195                 200                 205

Val His Ser Val His Leu Met Gly Tyr Val His Arg Asp Ile Lys Pro
```

-continued

```
    210                 215                 220

Glu Asn Ile Leu Val Asp Arg Thr Gly His Ile Lys Leu Val Asp Phe
225                 230                 235                 240

Gly Ser Ala Ala Lys Met Asn Ser Asn Lys Met Val Asn Ala Lys Leu
                245                 250                 255

Pro Ile Gly Thr Pro Asp Tyr Met Ala Pro Glu Val Leu Thr Val Met
            260                 265                 270

Asn Gly Asp Gly Lys Gly Thr Tyr Gly Leu Asp Cys Asp Trp Trp Ser
        275                 280                 285

Val Gly Val Ile Ala Tyr Glu Met Ile Tyr Gly Arg Ser Pro Phe Ala
    290                 295                 300

Glu Gly Thr Ser Ala Arg Thr Phe Asn Asn Ile Met Asn Phe Gln Arg
305                 310                 315                 320

Phe Leu Lys Phe Pro Asp Asp Pro Lys Val Ser Ser Asp Phe Leu Asp
                325                 330                 335

Leu Ile Gln Ser Leu Leu Cys Gly Gln Lys Glu Arg Leu Lys Phe Glu
            340                 345                 350

Gly Leu Cys Cys His Pro Phe Phe Ser Lys Ile Asp Trp Asn Asn Ile
        355                 360                 365

Arg Asn Ser Pro Pro Pro Phe Val Pro Thr Leu Lys Ser Asp Asp Asp
    370                 375                 380

Thr Ser Asn Phe Asp Glu Pro Glu Lys Asn Ser Trp Val Ser Ser Ser
385                 390                 395                 400

Pro Cys Gln Leu Ser Pro Ser Gly Phe Ser Gly Glu Glu Leu Pro Phe
                405                 410                 415

Val Gly Phe Ser Tyr Ser Lys Ala Leu Gly Ile Leu Gly Arg Ser Glu
            420                 425                 430

Ser Val Val Ser Gly Leu Asp Ser Pro Ala Lys Thr Ser Ser Met Glu
        435                 440                 445

Lys Lys Leu Leu Ile Lys Ser Lys Glu Leu Gln Asp Ser Gln Asp Lys
    450                 455                 460

Cys His Lys Met Glu Gln Glu Met Thr Arg Leu His Arg Arg Val Ser
465                 470                 475                 480

Glu Val Glu Ala Val Leu Ser Gln Lys Glu Val Glu Leu Lys Ala Ser
                485                 490                 495

Glu Thr Gln Arg Ser Leu Leu Glu Gln Asp Leu Ala Thr Tyr Ile Thr
            500                 505                 510

Glu Cys Ser Ser Leu Lys Arg Ser Leu Glu Gln Ala Arg Met Glu Val
        515                 520                 525

Ser Gln Glu Asp Asp Lys Ala Leu Gln Leu Leu His Asp Ile Arg Glu
    530                 535                 540

Gln Ser Arg Lys Leu Gln Glu Ile Lys Glu Gln Glu Tyr Gln Ala Gln
545                 550                 555                 560

Val Glu Glu Met Arg Leu Met Met Asn Gln Leu Glu Glu Asp Leu Val
                565                 570                 575

Ser Ala Arg Arg Arg Ser Asp Leu Tyr Glu Ser Glu Leu Arg Glu Ser
            580                 585                 590

Arg Leu Ala Ala Glu Glu Phe Lys Arg Lys Ala Thr Glu Cys Gln His
        595                 600                 605

Lys Leu Leu Lys Ala Lys Asp Gln Gly Lys Pro Glu Val Gly Glu Tyr
    610                 615                 620

Ala Lys Leu Glu Lys Ile Asn Ala Glu Gln Gln Leu Lys Ile Gln Glu
625                 630                 635                 640
```

-continued

```
Leu Gln Glu Lys Leu Glu Lys Ala Ala Lys Glu Arg Ala Glu Arg Glu
                645                 650                 655

Leu Glu Lys Leu Gln Asn Arg Glu Asp Ser Ser Glu Gly Ile Arg Lys
            660                 665                 670

Lys Leu Val Glu Ala Glu Glu Arg Arg His Ser Leu Glu Asn Lys Val
        675                 680                 685

Lys Arg Leu Glu Thr Met Glu Arg Arg Glu Asn Arg Leu Lys Asp Asp
    690                 695                 700

Ile Gln Thr Lys Ser Gln Gln Ile Gln Gln Met Ala Asp Lys Ile Leu
705                 710                 715                 720

Glu Leu Glu Glu Lys His Arg Glu Ala Gln Val Ser Ala Gln His Leu
                725                 730                 735

Glu Val His Leu Lys Gln Lys Glu Gln His Tyr Glu Glu Lys Ile Lys
            740                 745                 750

Val Leu Asp Asn Gln Ile Lys Lys Asp Leu Ala Asp Lys Glu Thr Leu
        755                 760                 765

Glu Asn Met Met Gln Arg His Glu Glu Glu Ala His Glu Lys Gly Lys
    770                 775                 780

Ile Leu Ser Glu Gln Lys Ala Met Ile Asn Ala Met Asp Ser Lys Ile
785                 790                 795                 800

Arg Ser Leu Glu Gln Arg Ile Val Glu Leu Ser Glu Ala Asn Lys Leu
                805                 810                 815

Ala Ala Asn Ser Ser Leu Phe Thr Gln Arg Asn Met Lys Ala Gln Glu
            820                 825                 830

Glu Met Ile Ser Glu Leu Arg Gln Gln Lys Phe Tyr Leu Glu Thr Gln
        835                 840                 845

Ala Gly Lys Leu Glu Ala Gln Asn Arg Lys Leu Glu Glu Gln Leu Glu
    850                 855                 860

Lys Ile Ser His Gln Asp His Ser Asp Lys Asn Arg Leu Leu Glu Leu
865                 870                 875                 880

Glu Thr Arg Leu Arg Glu Val Ser Leu Glu His Glu Glu Gln Lys Leu
                885                 890                 895

Glu Leu Lys Arg Gln Leu Thr Glu Leu Gln Leu Ser Leu Gln Glu Arg
            900                 905                 910

Glu Ser Gln Leu Thr Ala Leu Gln Ala Ala Arg Ala Ala Leu Glu Ser
        915                 920                 925

Gln Leu Arg Gln Ala Lys Thr Glu Leu Glu Glu Thr Thr Ala Glu Ala
    930                 935                 940

Glu Glu Glu Ile Gln Ala Leu Thr Ala His Arg Asp Glu Ile Gln Arg
945                 950                 955                 960

Lys Phe Asp Ala Leu Arg Asn Ser Cys Thr Val Ile Thr Asp Leu Glu
                965                 970                 975

Glu Gln Leu Asn Gln Leu Thr Glu Asp Asn Ala Glu Leu Asn Asn Gln
            980                 985                 990

Asn Phe Tyr Leu Ser Lys Gln Leu Asp Glu Ala Ser Gly Ala Asn Asp
        995                 1000                1005

Glu Ile Val Gln Leu Arg Ser Glu Val Asp His Leu Arg Arg Glu Ile
   1010                1015                1020

Thr Glu Arg Glu Met Gln Leu Thr Ser Gln Lys Gln Thr Met Glu Ala
1025                1030                1035                1040

Leu Lys Thr Thr Cys Thr Met Leu Glu Glu Gln Val Met Asp Leu Glu
               1045                1050                1055
```

-continued

```
Ala Leu Asn Asp Glu Leu Leu Glu Lys Glu Arg Gln Trp Glu Ala Trp
            1060                1065                1070

Arg Ser Val Leu Gly Asp Glu Lys Ser Gln Phe Glu Cys Arg Val Arg
        1075                1080                1085

Glu Leu Gln Arg Met Leu Asp Thr Glu Lys Gln Ser Arg Ala Arg Ala
    1090                1095                1100

Asp Gln Arg Ile Thr Glu Ser Arg Gln Val Val Glu Leu Ala Val Lys
1105                1110                1115                1120

Glu His Lys Ala Glu Ile Leu Ala Leu Gln Gln Ala Leu Lys Glu Gln
                1125                1130                1135

Lys Leu Lys Ala Glu Ser Leu Ser Asp Lys Leu Asn Asp Leu Glu Lys
            1140                1145                1150

Lys His Ala Met Leu Glu Met Asn Ala Arg Ser Leu Gln Gln Lys Leu
        1155                1160                1165

Glu Thr Glu Arg Glu Leu Lys Gln Arg Leu Leu Glu Glu Gln Ala Lys
    1170                1175                1180

Leu Gln Gln Gln Met Asp Leu Gln Lys Asn His Ile Phe Arg Leu Thr
1185                1190                1195                1200

Gln Gly Leu Gln Glu Ala Leu Asp Arg Ala Asp Leu Leu Lys Thr Glu
                1205                1210                1215

Arg Ser Asp Leu Glu Tyr Gln Leu Glu Asn Ile Gln Val Leu Tyr Ser
            1220                1225                1230

His Glu Lys Val Lys Met Glu Gly Thr Ile Ser Gln Gln Thr Lys Leu
        1235                1240                1245

Ile Asp Phe Leu Gln Ala Lys Met Asp Gln Pro Ala Lys Lys Lys Lys
    1250                1255                1260

Gly Leu Phe Ser Arg Arg Lys Glu Asp Pro Ala Leu Pro Thr Gln Val
1265                1270                1275                1280

Pro Leu Gln Tyr Asn Glu Leu Lys Leu Ala Leu Glu Lys Glu Lys Ala
                1285                1290                1295

Arg Cys Ala Glu Leu Glu Glu Ala Leu Gln Lys Thr Arg Ile Glu Leu
            1300                1305                1310

Arg Ser Ala Arg Glu Glu Ala Ala His Arg Lys Ala Thr Asp His Pro
        1315                1320                1325

His Pro Ser Thr Pro Ala Thr Ala Arg Gln Gln Ile Ala Met Ser Ala
    1330                1335                1340

Ile Val Arg Ser Pro Glu His Gln Pro Ser Ala Met Ser Leu Leu Ala
1345                1350                1355                1360

Pro Pro Ser Ser Arg Arg Lys Glu Ser Ser Thr Pro Glu Glu Phe Ser
                1365                1370                1375

Arg Arg Leu Lys Glu Arg Met His His Asn Ile Pro His Arg Phe Asn
            1380                1385                1390

Val Gly Leu Asn Met Arg Ala Thr Lys Cys Ala Val Cys Leu Asp Thr
        1395                1400                1405

Val His Phe Gly Arg Gln Ala Ser Lys Cys Leu Glu Cys Gln Val Met
    1410                1415                1420

Cys His Pro Lys Cys Ser Thr Cys Leu Pro Ala Thr Cys Gly Leu Pro
1425                1430                1435                1440

Ala Glu Tyr Ala Thr His Phe Thr Glu Ala Phe Cys Arg Asp Lys Met
                1445                1450                1455

Asn Ser Pro Gly Leu Gln Thr Lys Glu Pro Ser Ser Ser Leu His Leu
            1460                1465                1470

Glu Gly Trp Met Lys Val Pro Arg Asn Asn Lys Arg Gly Gln Gln Gly
```

-continued

```
      1475                1480                1485

Trp Asp Arg Lys Tyr Ile Val Leu Glu Gly Ser Lys Val Leu Ile Tyr
   1490                1495                1500

Asp Asn Glu Ala Arg Glu Ala Gly Gln Arg Pro Val Glu Glu Phe Glu
1505                1510                1515                1520

Leu Cys Leu Pro Asp Gly Asp Val Ser Ile His Gly Ala Val Gly Ala
               1525                1530                1535

Ser Glu Leu Ala Asn Thr Ala Lys Ala Glu Lys Ala Glu Ala Asp Ala
           1540                1545                1550

Lys Leu Leu Gly Asn Ser Leu Leu Lys Leu Glu Gly Asp Asp Arg Leu
       1555                1560                1565

Asp Met Asn Cys Thr Leu Pro Phe Ser Asp Gln Val Val Leu Val Gly
   1570                1575                1580

Thr Glu Glu Gly Leu Tyr Ala Leu Asn Val Leu Lys Asn Ser Leu Thr
1585                1590                1595                1600

His Val Pro Gly Ile Gly Ala Val Phe Gln Ile Tyr Ile Ile Lys Asp
               1605                1610                1615

Leu Glu Lys Leu Leu Met Ile Ala Gly Glu Glu Arg Ala Leu Cys Leu
           1620                1625                1630

Val Asp Val Lys Lys Val Lys Gln Ser Leu Ala Gln Ser His Leu Pro
       1635                1640                1645

Ala Gln Pro Asp Ile Ser Pro Asn Ile Phe Glu Ala Val Lys Gly Cys
   1650                1655                1660

His Leu Phe Gly Ala Gly Lys Ile Glu Asn Gly Leu Cys Ile Cys Ala
1665                1670                1675                1680

Ala Met Pro Ser Lys Val Val Ile Leu Arg Tyr Asn Glu Asn Leu Ser
               1685                1690                1695

Lys Tyr Cys Ile Arg Lys Glu Ile Glu Thr Ser Glu Pro Cys Ser Cys
           1700                1705                1710

Ile His Phe Thr Asn Tyr Ser Ile Leu Ile Gly Thr Asn Lys Phe Tyr
       1715                1720                1725

Glu Ile Asp Met Lys Gln Tyr Thr Leu Glu Glu Phe Leu Asp Lys Asn
   1730                1735                1740

Asp His Ser Leu Ala Pro Ala Val Phe Ala Ala Ser Ser Asn Ser Phe
1745                1750                1755                1760

Pro Val Ser Ile Val Gln Val Asn Ser Ala Gly Gln Arg Glu Glu Tyr
               1765                1770                1775

Leu Leu Cys Phe His Glu Phe Gly Val Phe Val Asp Ser Tyr Gly Arg
           1780                1785                1790

Arg Ser Arg Thr Asp Asp Leu Lys Trp Ser Arg Leu Pro Leu Ala Phe
       1795                1800                1805

Ala Tyr Arg Glu Pro Tyr Leu Phe Val Thr His Phe Asn Ser Leu Glu
   1810                1815                1820

Val Ile Glu Ile Gln Ala Arg Ser Ser Ala Gly Thr Pro Ala Arg Ala
1825                1830                1835                1840

Tyr Leu Asp Ile Pro Asn Pro Arg Tyr Leu Gly Pro Ala Ile Ser Ser
               1845                1850                1855

Gly Ala Ile Tyr Leu Ala Ser Ser Tyr Gln Asp Lys Leu Arg Val Ile
           1860                1865                1870

Cys Cys Lys Gly Asn Leu Val Lys Glu Ser Gly Thr Glu His His Arg
       1875                1880                1885

Gly Pro Ser Thr Ser Arg Ser Ser Pro Asn Lys Arg Gly Pro Pro Thr
   1890                1895                1900
```

-continued

```
Tyr Asn Glu His Ile Thr Lys Arg Val Ala Ser Ser Pro Ala Pro Pro
1905                1910                1915                1920

Glu Gly Pro Ser His Pro Arg Glu Pro Ser Thr Pro His Arg Tyr Arg
               1925                1930                1935

Glu Gly Arg Thr Glu Leu Arg Arg Asp Lys Ser Pro Gly Arg Pro Leu
           1940                1945                1950

Glu Arg Glu Lys Ser Pro Gly Arg Met Leu Ser Thr Arg Arg Glu Arg
       1955                1960                1965

Ser Pro Gly Arg Leu Phe Glu Asp Ser Ser Arg Gly Arg Leu Pro Ala
   1970                1975                1980

Gly Ala Val Arg Thr Pro Leu Ser Gln Val Asn Lys Gly Arg Gly Gln
1985                1990                1995                2000

Ser Ala Ser Gln Val Phe Thr Val Asn Thr Val Thr Tyr Tyr Asp Trp
               2005                2010                2015

Asn Lys Lys Leu Asp Asn Leu Pro Ala Asn Trp Ser Val Leu Arg Ile
           2020                2025                2030

Ile Gln Leu Asn Gly Glu Ile Arg Gln Gln Val Glu Lys Ser Val Leu
       2035                2040                2045

Arg Thr Asp Tyr Cys
   2050
```

<210> SEQ ID NO 3
<211> LENGTH: 6159
<212> TYPE: DNA
<213> ORGANISM: Homo sapiens

<400> SEQUENCE: 3

```
atgttgaagt tcaaatatgg agcgcggaat cctttggatg ctggtgctgc tgaacccatt     60

gccagccggg cctccaggct gaatctgttc ttccagggga aaccaccctt tatgactcaa    120

cagcagatgt ctcctctttc ccgagaaggg atattagatg ccctctttgt tctctttgaa    180

gaatgcagtc agcctgctct gatgaagatt aagcacgtga gcaactttgt ccggaagtat    240

tccgacacca tagctgagtt acaggagctc cagccttcgg caaaggactt cgaagtcaga    300

agtcttgtag gttgtggtca ctttgctgaa gtgcaggtgg taagagagaa agcaaccggg    360

gacatctatg ctatgaaagt gatgaagaag aaggctttat tggcccagga gcaggtttca    420

ttttttgagg aagagcggaa catattatct cgaagcacaa gcccgtggat cccccaatta    480

cagtatgcct ttcaggacaa aaatcacctt tatctgatgg aggaatatca gcctggaggg    540

gacttgctgt cacttttgaa tagatatgag gaccagttag atgaaaacct gatacagttt    600

tacctagctg agctgatttt ggctgttcac agcgttcatc tgatgggata cgtgcatcga    660

gacatcaagc ctgagaacat tctcgttgac cgcacaggac acatcaagct ggtggatttt    720

ggatctgccg cgaaaatgaa ttcaaacaag atggtgaatg ccaaactccc gattgggacc    780

ccagattaca tggctcctga agtgctgact gtgatgaacg gggatggaaa aggcacctac    840

ggcctggact gtgactggtg gtcagtgggc gtgattgcct atgagatgat ttatgggaga    900

tccccctttcg cagagggaac ctctgccaga accttcaata acattatgaa tttccagcgg    960

tttttgaaat ttccagatga ccccaaagtg agcagtgact ttcttgatct gattcaaagc   1020

ttgttgtgcg gccagaaaga gagactgaag tttgaaggtc tttgctgcca tcctttcttc   1080

tctaaaattg actggaacaa cattcgtaac tctcctcccc ccttcgttcc caccctcaag   1140

tctgacgatg acacctccaa ttttgatgaa ccagagaaga attcgtgggt ttcatcctct   1200
```

-continued

```
ccgtgccagc tgagcccctc aggcttctcg ggtgaagaac tgccgtttgt ggggttttcg   1260

tacagcaagg cactggggat tcttggtaga tctgagtctg ttgtgtcggg tctggactcc   1320

cctgccaaga ctagctccat ggaaaagaaa cttctcatca aaagcaaaga gctacaagac   1380

tctcaggaca agtgtcacaa gatggagcag gaaatgaccc ggttacatcg gagagtgtca   1440

gaggtggagg ctgtgcttag tcagaaggag gtggagctga aggcctctga gactcagaga   1500

tccctcctgg agcaggacct tgctacctac atcacagaat gcagtagctt aaagcgaagt   1560

ttggagcaag cacggatgga ggtgtcccag gaggatgaca aagcactgca gcttctccat   1620

gatatcagag agcagagccg gaagctccaa gaaatcaaag agcaggagta ccaggctcaa   1680

gtggaagaaa tgaggttgat gatgaatcag ttggaagagg atcttgtctc agcaagaaga   1740

cggagtgatc tctacgaatc tgagctgaga gagtctcggc ttgctgctga agaattcaag   1800

cggaaagcga cagaatgtca gcataaactg ttgaaggcta aggatcaagg gaagcctgaa   1860

gtgggagaat atgcgaaact ggagaagatc aatgctgagc agcagctcaa aattcaggag   1920

ctccaagaga aactggagaa ggctgcaaag gagcgagccg agagggagct ggagaagctg   1980

cagaaccgag aggattcttc tgaaggcatc agaaagaagc tggtggaagc tgaggaacgc   2040

cgccattctc tggagaacaa ggtaaagaga ctagagacca tggagcgtag agaaaacaga   2100

ctgaaggatg acatccagac aaaatcccaa cagatccagc agatggctga taaaattctg   2160

gagctcgaag agaaacatcg ggaggcccaa gtctcagccc agcacctaga agtgcacctg   2220

aaacagaaag agcagcacta tgaggaaaag attaaagtgt tggacaatca gataaagaaa   2280

gacctggctg acaaggagac actggagaac atgatgcaga gacacgagga ggaggcccat   2340

gagaagggca aaattctcag cgaacagaag gcgatgatca atgctatgga ttccaagatc   2400

agatccctgg aacagaggat tgtggaactg tctgaagcca ataaacttgc agcaaatagc   2460

agtcttttta cccaaaggaa catgaaggcc caagaagaga tgatttctga actcaggcaa   2520

cagaaatttt acctggagac acaggctggg aagttggagg cccagaaccg aaaactggag   2580

gagcagctgg agaagatcag ccaccaagac cacagtgaca agaatcggct gctggaactg   2640

gagacaagat tgcgggaggt cagtctagag cacgaggagc agaaactgga gctcaagcgc   2700

cagctcacag agctacagct ctccctgcag gagcgcgagt cacagttgac agccctgcag   2760

gctgcacggg cggccctgga gagccagctt cgccaggcga agacagagct ggaagagacc   2820

acagcagaag ctgaagagga gatccaggca ctcacggcac atagagatga aatccagcgc   2880

aaatttgatg ctcttcgtaa cagctgtact gtaatcacag acctggagga gcagctaaac   2940

cagctgaccg aggacaacgc tgaactcaac aaccaaaact tctacttgtc caaacaactc   3000

gatgaggctt ctggcgccaa cgacgagatt gtacaactgc gaagtgaagt ggaccatctc   3060

cgccgggaga tcacggaacg agagatgcag cttaccagcc agaagcaaac gatggaggct   3120

ctgaagacca cgtgcaccat gctggaggaa caggtcatgg atttggaggc cctaaacgat   3180

gagctgctag aaaaagagcg gcagtgggag gcctggagga gcgtcctggg tgatgagaaa   3240

tcccagtttg agtgtcgggt tcgagagctg cagagaatgc tggacaccga gaaacagagc   3300

agggcgagag ccgatcagcg gatcaccgag tctcgccagg tggtggagct ggcagtgaag   3360

gagcacaagg ctgagattct cgctctgcag caggctctca aagagcagaa gctgaaggcc   3420

gagagcctct ctgacaagct caatgacctg gagaagaagc atgctatgct tgaaatgaat   3480

gcccgaagct tacagcagaa gctggagact gaacgagagc tcaaacagag gcttctggaa   3540

gagcaagcca aattacagca gcagatggac ctgcagaaaa atcacatttt ccgtctgact   3600
```

-continued

```
caaggactgc aagaagctct agatcgggct gatctactga agacagaaag aagtgacttg   3660
gagtatcagc tggaaaacat tcaggttctc tattctcatg aaaaggtgaa aatggaaggc   3720
actatttctc aacaaaccaa actcattgat tttctgcaag ccaaaatgga ccaacctgct   3780
aaaaagaaaa agggtttatt tagtcgacgg aaagaggacc ctgctttacc cacacaggtt   3840
cctctgcagt acaatgagct gaagctggcc ctggagaagg agaaagctcg ctgtgcagag   3900
ctagaggaag cccttcagaa gacccgcatc gagctccggt ccgcccggga ggaagctgcc   3960
caccgcaaag caacggacca cccacaccca tccacgccag ccaccgcgag gcagcagatc   4020
gccatgtccg ccatcgtgcg gtcgccagag caccagccca gtgccatgag cctgctggcc   4080
ccgccatcca gccgcagaaa ggagtcttca actccagagg aatttagtcg gcgtcttaag   4140
gaacgcatgc accacaatat tcctcaccga ttcaacgtag gactgaacat gcgagccaca   4200
aagtgtgctg tgtgtctgga taccgtgcac tttggacgcc aggcatccaa atgtctcgaa   4260
tgtcaggtga tgtgtcaccc caagtgctcc acgtgcttgc cagccacctg cggcttgcct   4320
gctgaatatg ccacacactt caccgaggcc ttctgccgtg acaaaatgaa ctccccaggt   4380
ctccagacca aggagcccag cagcagcttg cacctggaag ggtggatgaa ggtgcccagg   4440
aataacaaac gaggacagca aggctgggac aggaagtaca ttgtcctgga gggatcaaaa   4500
gtcctcattt atgacaatga agccagagaa gctggacaga ggccggtgga agaatttgag   4560
ctgtgccttc ccgacgggga tgtatctatt catggtgccg ttggtgcttc cgaactcgca   4620
aatacagcca aagcagaaaa agcagaagct gatgctaaac tgcttggaaa ctccctgctg   4680
aaactggaag gtgatgaccg tctagacatg aactgcacgc tgcccttcag tgaccaggtg   4740
gtgttggtgg gcaccgagga agggctctac gccctgaatg tcttgaaaaa ctccctaacc   4800
catgtcccag gaattggagc agtcttccaa atttatatta tcaaggacct ggagaagcta   4860
ctcatgatag caggagaaga gcgggcactg tgtcttgtgg acgtgaagaa agtgaaacag   4920
tccctggccc agtcccacct gcctgcccag cccgacatct cacccaacat tttgaagct   4980
gtcaagggct gccacttgtt tggggcaggc aagattgaga acgggctctg catctgtgca   5040
gccatgccca gcaaagtcgt cattctccgc tacaacgaaa acctcagcaa atactgcatc   5100
cggaaagaga tagagacctc agagccctgc agctgtatcc acttcaccaa ttacagtatc   5160
ctcattggaa ccaataaatt ctacgaaatc gacatgaagc agtacacgct cgaggaattc   5220
ctggataaga atgaccattc cttggcacct gctgtgtttg ccgcctcttc caacagcttc   5280
cctgtctcaa tcgtgcaggt gaacagcgca gggcagcgag aggagtactt gctgtgtttc   5340
cacgaatttg gagtgttcgt ggattcttac ggaagacgta gccgcacaga cgatctcaag   5400
tggagtcgct tacctttggc ctttgcctac agagaaccct atctgtttgt gacccacttc   5460
aactcactcg aagtaattga gatccaggca cgctcctcag cagggacccc tgcccgagcg   5520
tacctggaca tcccgaaccc gcgctacctg ggccctgcca tttcctcagg agcgatttac   5580
ttggcgtcct cataccagga taaattaagg gtcatttgct gcaagggaaa cctcgtgaag   5640
gagtccggca ctgaacacca ccggggcccg tccacctccc gcagcagccc caacaagcga   5700
ggcccaccca cgtacaacga gcacatcacc aagcgcgtgg cctccagccc agcgccgccc   5760
gaaggcccca gccacccgcg agagccaagc acaccccacc gctaccgcga ggggcggacc   5820
gagctgcgca gggacaagtc tcctggccgc cccctggagc gagagaagtc ccccggccgg   5880
atgctcagca cgcggagaga gcggtccccc gggaggctgt ttgaagacag cagcaggggc   5940
```

-continued

```
cggctgcctg cgggagccgt gaggaccccg ctgtcccagg tgaacaaggg aagagggcag   6000

agtgcctctc aagttttcac ggttaacact gtcacctatt atgactggaa taaaaagctg   6060

gacaacctgc cagctaactg gtcagtcctg aggatcatcc agctgaatgg agaaatccgg   6120

cagcaggttg aaaagtctgt tctgagaaca gattattgc                          6159


<210> SEQ ID NO 4
<211> LENGTH: 2055
<212> TYPE: PRT
<213> ORGANISM: Mus musculus

<400> SEQUENCE: 4

Met Leu Lys Phe Lys Tyr Gly Val Arg Asn Pro Pro Glu Ala Ser Ala
  1               5                  10                  15

Ser Glu Pro Ile Ala Ser Arg Ala Ser Arg Leu Asn Leu Phe Phe Gln
             20                  25                  30

Gly Lys Pro Pro Leu Met Thr Gln Gln Gln Met Ser Ala Leu Ser Arg
         35                  40                  45

Glu Gly Met Leu Asp Ala Leu Phe Ala Leu Phe Glu Glu Cys Ser Gln
     50                  55                  60

Pro Ala Leu Met Lys Met Lys His Val Ser Ser Phe Val Gln Lys Tyr
 65                  70                  75                  80

Ser Asp Thr Ile Ala Glu Leu Arg Glu Leu Gln Pro Ser Ala Arg Asp
                 85                  90                  95

Phe Glu Val Arg Ser Leu Val Gly Cys Gly His Phe Ala Glu Val Gln
            100                 105                 110

Val Val Arg Glu Lys Ala Thr Gly Asp Val Tyr Ala Met Lys Ile Met
        115                 120                 125

Lys Lys Lys Ala Leu Leu Ala Gln Glu Gln Val Ser Phe Phe Glu Glu
    130                 135                 140

Glu Arg Asn Ile Leu Ser Arg Ser Thr Ser Pro Trp Ile Pro Gln Leu
145                 150                 155                 160

Gln Tyr Ala Phe Gln Asp Lys Asn Asn Leu Tyr Leu Val Met Glu Tyr
                165                 170                 175

Gln Pro Gly Gly Asp Phe Leu Ser Leu Leu Asn Arg Tyr Glu Asp Gln
            180                 185                 190

Leu Asp Glu Ser Met Ile Gln Phe Tyr Leu Ala Glu Leu Ile Leu Ala
        195                 200                 205

Val His Ser Val His Gln Met Gly Tyr Val His Arg Asp Ile Lys Pro
    210                 215                 220

Glu Asn Ile Leu Ile Asp Arg Thr Gly Glu Ile Lys Leu Val Asp Phe
225                 230                 235                 240

Gly Ser Ala Ala Lys Met Asn Ser Asn Lys Val Asp Ala Lys Leu Pro
                245                 250                 255

Ile Gly Thr Pro Asp Tyr Met Ala Pro Glu Val Leu Thr Val Met Asn
            260                 265                 270

Glu Asp Arg Arg Gly Thr Tyr Gly Leu Asp Cys Asp Trp Trp Ser Val
        275                 280                 285

Gly Val Val Ala Tyr Glu Met Val Tyr Gly Lys Thr Pro Phe Thr Glu
    290                 295                 300

Gly Thr Ser Ala Arg Thr Phe Asn Asn Ile Met Asn Phe Gln Arg Phe
305                 310                 315                 320

Leu Lys Phe Pro Asp Asp Pro Lys Val Ser Ser Glu Leu Leu Asp Leu
                325                 330                 335
```

-continued

```
Leu Gln Ser Leu Leu Cys Val Gln Lys Glu Arg Leu Lys Phe Glu Gly
            340                 345                 350

Leu Cys Cys His Pro Phe Phe Ala Arg Thr Asp Trp Asn Asn Ile Arg
        355                 360                 365

Asn Ser Pro Pro Pro Phe Val Pro Thr Leu Lys Ser Asp Asp Asp Thr
    370                 375                 380

Ser Asn Phe Asp Glu Pro Glu Lys Asn Ser Trp Ala Phe Ile Leu Cys
385                 390                 395                 400

Val Pro Ala Glu Pro Leu Ala Phe Ser Gly Glu Glu Leu Pro Phe Val
                405                 410                 415

Gly Phe Ser Tyr Ser Lys Ala Leu Gly Tyr Leu Gly Arg Ser Glu Ser
            420                 425                 430

Val Val Ser Ser Leu Asp Ser Pro Ala Lys Val Ser Ser Met Glu Lys
        435                 440                 445

Lys Leu Leu Ile Lys Ser Lys Glu Leu Gln Asp Ser Gln Asp Lys Cys
    450                 455                 460

His Lys Met Glu Gln Glu Met Thr Arg Leu His Arg Arg Val Ser Glu
465                 470                 475                 480

Val Glu Ala Val Leu Ser Gln Lys Glu Val Glu Leu Lys Ala Ser Glu
                485                 490                 495

Thr Gln Arg Ser Leu Leu Glu Gln Asp Leu Ala Thr Tyr Ile Thr Glu
            500                 505                 510

Cys Ser Ser Leu Lys Arg Ser Leu Glu Gln Ala Arg Met Glu Val Ser
        515                 520                 525

Gln Glu Asp Asp Lys Ala Leu Gln Leu Leu His Asp Ile Arg Glu Gln
    530                 535                 540

Ser Arg Lys Leu Gln Glu Ile Lys Glu Gln Glu Tyr Gln Ala Gln Val
545                 550                 555                 560

Glu Glu Met Arg Leu Met Met Asn Gln Leu Glu Glu Asp Leu Val Ser
                565                 570                 575

Ala Arg Arg Arg Ser Asp Leu Tyr Glu Ser Glu Leu Arg Glu Ser Arg
            580                 585                 590

Leu Ala Ala Glu Glu Phe Lys Arg Lys Ala Asn Glu Cys Gln His Lys
        595                 600                 605

Leu Met Lys Ala Lys Asp Gln Gly Lys Pro Glu Val Gly Glu Tyr Ser
    610                 615                 620

Lys Leu Glu Lys Ile Asn Ala Glu Gln Gln Leu Lys Ile Gln Glu Leu
625                 630                 635                 640

Gln Glu Lys Leu Glu Lys Ala Val Lys Ala Ser Thr Glu Ala Thr Glu
                645                 650                 655

Leu Leu Gln Asn Ile Arg Gln Ala Lys Glu Arg Ala Glu Arg Glu Leu
            660                 665                 670

Glu Lys Leu His Asn Arg Glu Asp Ser Ser Glu Gly Ile Lys Lys Lys
        675                 680                 685

Leu Val Glu Ala Glu Glu Arg Arg His Ser Leu Glu Asn Lys Val Lys
    690                 695                 700

Arg Leu Glu Thr Met Glu Arg Arg Glu Asn Arg Leu Lys Asp Asp Ile
705                 710                 715                 720

Gln Thr Lys Ser Glu Gln Ile Gln Gln Met Ala Asp Lys Ile Leu Glu
                725                 730                 735

Leu Glu Glu Lys His Arg Glu Ala Gln Val Ser Ala Gln His Leu Glu
            740                 745                 750

Val His Leu Lys Gln Lys Glu Gln His Tyr Glu Glu Lys Ile Lys Val
```

-continued

```
        755                 760                 765

Leu Asp Asn Gln Ile Lys Lys Asp Leu Ala Asp Lys Glu Ser Leu Glu
    770                 775                 780

Asn Met Met Gln Arg His Glu Glu Glu Ala His Glu Lys Gly Lys Ile
785                 790                 795                 800

Leu Ser Glu Gln Lys Ala Met Ile Asn Ala Met Asp Ser Lys Ile Arg
                805                 810                 815

Ser Leu Glu Gln Arg Ile Val Glu Leu Ser Glu Ala Asn Lys Leu Ala
            820                 825                 830

Ala Asn Ser Ser Leu Phe Thr Gln Arg Asn Met Lys Ala Gln Glu Glu
        835                 840                 845

Met Ile Ser Glu Leu Arg Gln Gln Lys Phe Tyr Leu Glu Thr Gln Ala
    850                 855                 860

Gly Lys Leu Glu Ala Gln Asn Arg Lys Leu Glu Glu Gln Leu Glu Lys
865                 870                 875                 880

Ile Ser His Gln Asp His Ser Asp Lys Ser Arg Leu Leu Glu Leu Glu
                885                 890                 895

Thr Arg Leu Arg Glu Val Ser Leu Glu His Glu Glu Gln Lys Leu Glu
            900                 905                 910

Leu Lys Arg Gln Leu Thr Glu Leu Gln Leu Ser Leu Gln Glu Arg Glu
        915                 920                 925

Ser Gln Leu Thr Ala Leu Gln Ala Ala Arg Ala Ala Leu Glu Ser Gln
    930                 935                 940

Leu Arg Gln Ala Lys Thr Glu Leu Glu Glu Thr Thr Ala Glu Ala Glu
945                 950                 955                 960

Glu Glu Ile Gln Ala Leu Thr Ala His Arg Asp Glu Ile Gln Arg Lys
                965                 970                 975

Phe Asp Ala Leu Arg Asn Ser Cys Thr Val Ile Thr Asp Leu Glu Glu
            980                 985                 990

Gln Leu Asn Gln Leu Thr Glu Asp Asn Ala Glu Leu Asn Asn Gln Asn
        995                1000                1005

Phe Tyr Leu Ser Lys Gln Leu Asp Glu Ala Ser Gly Ala Asn Asp Glu
   1010                1015                1020

Ile Val Gln Leu Arg Ser Glu Val Asp His Leu Arg Arg Glu Ile Thr
1025                1030                1035                1040

Glu Arg Glu Met Gln Leu Thr Ser Gln Lys Gln Thr Met Glu Ala Leu
               1045                1050                1055

Lys Thr Thr Cys Thr Met Leu Glu Glu Gln Val Leu Asp Leu Glu Ala
           1060                1065                1070

Leu Asn Asp Glu Leu Leu Glu Lys Glu Arg Gln Trp Glu Ala Trp Arg
       1075                1080                1085

Ser Val Leu Gly Asp Glu Lys Ser Gln Phe Glu Cys Arg Val Arg Glu
   1090                1095                1100

Leu Gln Arg Met Leu Asp Thr Glu Lys Gln Ser Arg Ala Arg Ala Asp
1105                1110                1115                1120

Gln Arg Ile Thr Glu Ser Arg Gln Val Val Glu Leu Ala Val Lys Glu
               1125                1130                1135

His Lys Ala Glu Ile Leu Ala Leu Gln Gln Ala Leu Lys Glu Gln Lys
           1140                1145                1150

Leu Lys Ala Glu Ser Leu Ser Asp Lys Leu Asn Asp Leu Glu Lys Lys
       1155                1160                1165

His Ala Met Leu Glu Met Asn Ala Arg Ser Leu Gln Gln Lys Leu Glu
   1170                1175                1180
```

-continued

```
Thr Glu Arg Glu Leu Lys Gln Arg Leu Leu Glu Glu Gln Ala Lys Leu
1185                1190                1195                1200

Gln Gln Gln Met Asp Leu Gln Lys Asn His Ile Phe Arg Leu Thr Gln
                1205                1210                1215

Gly Leu Gln Glu Ala Leu Asp Arg Ala Asp Leu Leu Lys Thr Glu Arg
            1220                1225                1230

Ser Asp Leu Glu Tyr Gln Leu Glu Asn Ile Gln Val Leu Tyr Ser His
        1235                1240                1245

Glu Lys Val Lys Met Glu Gly Thr Ile Ser Gln Gln Thr Lys Leu Ile
    1250                1255                1260

Asp Phe Leu Gln Ala Lys Met Asp Gln Pro Ala Lys Lys Lys Lys Val
1265                1270                1275                1280

Pro Leu Gln Tyr Asn Glu Leu Lys Leu Ala Leu Glu Lys Glu Lys Ala
                1285                1290                1295

Arg Cys Ala Glu Leu Glu Glu Ala Leu Gln Lys Thr Arg Ile Glu Leu
            1300                1305                1310

Arg Ser Ala Arg Glu Glu Ala Ala His Arg Lys Ala Thr Asp His Pro
        1315                1320                1325

His Pro Ser Thr Pro Ala Thr Ala Arg Gln Gln Ile Ala Met Ser Ala
    1330                1335                1340

Ile Val Arg Ser Pro Glu His Gln Pro Ser Ala Met Ser Leu Leu Ala
1345                1350                1355                1360

Pro Pro Ser Ser Arg Arg Lys Glu Ser Ser Thr Pro Glu Glu Phe Ser
                1365                1370                1375

Arg Arg Leu Lys Glu Arg Met His His Asn Ile Pro His Arg Phe Asn
            1380                1385                1390

Val Gly Leu Asn Met Arg Ala Thr Lys Cys Ala Val Cys Leu Asp Thr
        1395                1400                1405

Val His Phe Gly Arg Gln Ala Ser Lys Cys Leu Glu Cys Gln Val Met
    1410                1415                1420

Cys His Pro Lys Cys Ser Thr Cys Leu Pro Ala Thr Cys Gly Leu Pro
1425                1430                1435                1440

Ala Glu Tyr Ala Thr His Phe Thr Glu Ala Phe Cys Arg Asp Lys Met
                1445                1450                1455

Asn Ser Pro Gly Leu Gln Ser Lys Glu Pro Gly Ser Ser Leu His Leu
            1460                1465                1470

Glu Gly Trp Met Lys Val Pro Arg Asn Asn Lys Arg Gly Gln Gln Gly
        1475                1480                1485

Trp Asp Arg Lys Tyr Ile Val Leu Glu Gly Ser Lys Val Leu Ile Tyr
    1490                1495                1500

Asp Asn Glu Ala Arg Glu Ala Gly Gln Arg Pro Val Glu Glu Phe Glu
1505                1510                1515                1520

Leu Cys Leu Pro Asp Gly Asp Val Ser Ile His Gly Ala Val Gly Ala
                1525                1530                1535

Ser Glu Leu Ala Asn Thr Ala Lys Ala Asp Val Pro Tyr Ile Leu Lys
            1540                1545                1550

Met Glu Ser His Pro His Thr Thr Cys Trp Pro Gly Arg Thr Leu Tyr
        1555                1560                1565

Leu Leu Ala Pro Ser Phe Pro Asp Lys Gln Arg Trp Val Thr Ala Leu
    1570                1575                1580

Glu Ser Val Val Ala Gly Gly Arg Val Ser Arg Glu Lys Ala Glu Ala
1585                1590                1595                1600
```

-continued

```
Asp Ala Lys Leu Leu Gly Asn Ser Leu Leu Lys Leu Glu Gly Asp Asp
                1605                1610                1615

Arg Leu Asp Met Asn Cys Thr Leu Pro Phe Ser Asp Gln Val Val Leu
            1620                1625                1630

Val Gly Thr Glu Glu Gly Leu Tyr Ala Leu Asn Val Leu Lys Asn Ser
        1635                1640                1645

Leu Thr His Ile Pro Gly Ile Gly Ala Val Phe Gln Ile Tyr Ile Ile
    1650                1655                1660

Lys Asp Leu Glu Lys Leu Leu Met Ile Ala Gly Glu Glu Arg Ala Leu
1665                1670                1675                1680

Cys Leu Val Asp Val Lys Lys Val Lys Gln Ser Leu Ala Gln Ser His
                1685                1690                1695

Leu Pro Ala Gln Pro Asp Val Ser Pro Asn Ile Phe Glu Ala Val Lys
            1700                1705                1710

Gly Cys His Leu Phe Ala Ala Gly Lys Ile Glu Asn Ser Leu Cys Ile
        1715                1720                1725

Cys Ala Ala Met Pro Ser Lys Val Val Ile Leu Arg Tyr Asn Asp Asn
    1730                1735                1740

Leu Ser Lys Tyr Cys Ile Arg Lys Glu Ile Glu Thr Ser Glu Pro Cys
1745                1750                1755                1760

Ser Cys Ile His Phe Thr Asn Tyr Ser Ile Leu Ile Gly Thr Asn Lys
                1765                1770                1775

Phe Tyr Glu Ile Asp Met Lys Gln Tyr Thr Leu Asp Glu Phe Leu Asp
            1780                1785                1790

Lys Asn Asp His Ser Leu Ala Pro Ala Val Phe Ala Ser Ser Ser Asn
        1795                1800                1805

Ser Phe Pro Val Ser Ile Val Gln Ala Asn Ser Ala Gly Gln Arg Glu
    1810                1815                1820

Glu Tyr Leu Leu Cys Phe His Glu Phe Gly Val Phe Val Asp Ser Tyr
1825                1830                1835                1840

Gly Arg Arg Ser Arg Thr Asp Asp Leu Lys Trp Ser Arg Leu Pro Leu
                1845                1850                1855

Ala Phe Ala Tyr Arg Glu Pro Tyr Leu Phe Val Thr His Phe Asn Ser
            1860                1865                1870

Leu Glu Val Ile Glu Ile Gln Ala Arg Ser Ser Leu Gly Ser Pro Ala
        1875                1880                1885

Arg Ala Tyr Leu Glu Ile Pro Asn Pro Arg Tyr Leu Gly Pro Ala Ile
    1890                1895                1900

Ser Ser Gly Ala Ile Tyr Leu Ala Ser Ser Tyr Gln Asp Lys Leu Arg
1905                1910                1915                1920

Val Ile Cys Cys Lys Gly Asn Leu Val Lys Glu Ser Gly Thr Glu Gln
                1925                1930                1935

His Arg Val Pro Ser Thr Ser Arg Ser Ser Pro Asn Lys Arg Gly Pro
            1940                1945                1950

Pro Thr Tyr Asn Glu His Ile Thr Lys Arg Val Ala Ser Ser Pro Ala
        1955                1960                1965

Pro Pro Glu Gly Pro Ser His Pro Arg Glu Pro Ser Thr Pro His Arg
    1970                1975                1980

Tyr Arg Asp Arg Glu Gly Arg Thr Glu Leu Arg Arg Asp Lys Ser Pro
1985                1990                1995                2000

Gly Arg Pro Leu Glu Arg Glu Lys Ser Pro Gly Arg Met Leu Ser Thr
                2005                2010                2015

Arg Arg Glu Arg Ser Pro Gly Arg Leu Phe Glu Asp Ser Ser Arg Gly
```

-continued

```
        2020                2025                2030

Arg Leu Pro Ala Gly Ala Val Arg Thr Pro Leu Ser Gln Val Asn Lys
     2035                2040                2045

Val Trp Asp Gln Ser Ser Val
  2050                2055


<210> SEQ ID NO 5
<211> LENGTH: 1641
<212> TYPE: PRT
<213> ORGANISM: Mus musculus

<400> SEQUENCE: 5

Pro Phe Val Pro Thr Leu Lys Ser Asp Asp Asp Thr Ser Asn Phe Asp
 1               5                  10                  15

Glu Pro Glu Lys Asn Ser Trp Val Ser Ser Ser Val Cys Gln Leu Ser
            20                  25                  30

Pro Ser Gly Phe Ser Gly Glu Glu Leu Pro Phe Val Gly Phe Ser Tyr
        35                  40                  45

Ser Lys Ala Leu Gly Tyr Leu Gly Arg Ser Glu Ser Val Val Ser Ser
    50                  55                  60

Leu Asp Ser Pro Ala Lys Val Ser Ser Met Glu Lys Lys Leu Leu Ile
65                  70                  75                  80

Lys Ser Lys Glu Leu Gln Asp Ser Gln Asp Lys Cys His Lys Met Glu
                85                  90                  95

Gln Glu Met Thr Arg Leu His Arg Arg Val Ser Glu Val Glu Ala Val
            100                 105                 110

Leu Ser Gln Lys Glu Val Glu Leu Lys Ala Ser Glu Thr Gln Arg Ser
        115                 120                 125

Leu Leu Glu Gln Asp Leu Ala Thr Tyr Ile Thr Glu Cys Ser Ser Leu
    130                 135                 140

Lys Arg Ser Leu Glu Gln Ala Arg Met Glu Val Ser Gln Glu Asp Asp
145                 150                 155                 160

Lys Ala Leu Gln Leu Leu His Asp Ile Arg Glu Gln Ser Arg Lys Leu
                165                 170                 175

Gln Glu Ile Lys Glu Gln Glu Tyr Gln Ala Gln Val Glu Glu Met Arg
            180                 185                 190

Leu Met Met Asn Gln Leu Glu Glu Asp Leu Val Ser Ala Arg Arg Arg
        195                 200                 205

Ser Asp Leu Tyr Glu Ser Glu Leu Arg Glu Ser Arg Leu Ala Ala Glu
    210                 215                 220

Glu Phe Lys Arg Lys Ala Asn Glu Cys Gln His Lys Leu Met Lys Ala
225                 230                 235                 240

Lys Asp Gln Gly Lys Pro Glu Val Gly Glu Tyr Ser Lys Leu Glu Lys
                245                 250                 255

Ile Asn Ala Glu Gln Gln Leu Lys Ile Gln Glu Leu Gln Glu Lys Leu
            260                 265                 270

Glu Lys Ala Val Lys Ala Ser Thr Glu Ala Thr Glu Leu Leu Gln Asn
        275                 280                 285

Ile Arg Gln Ala Lys Glu Arg Ala Glu Arg Glu Leu Glu Lys Leu His
    290                 295                 300

Asn Arg Glu Asp Ser Ser Glu Gly Ile Lys Lys Lys Leu Val Glu Ala
305                 310                 315                 320

Glu Glu Leu Glu Glu Lys His Arg Glu Ala Gln Val Ser Ala Gln His
                325                 330                 335
```

-continued

```
Leu Glu Val His Leu Lys Gln Lys Glu Gln His Tyr Glu Glu Lys Ile
            340                 345                 350

Lys Val Leu Asp Asn Gln Ile Lys Lys Asp Leu Ala Asp Lys Glu Ser
        355                 360                 365

Leu Glu Asn Met Met Gln Arg His Glu Glu Glu Ala His Glu Lys Gly
    370                 375                 380

Lys Ile Leu Ser Glu Gln Lys Ala Met Ile Asn Ala Met Asp Ser Lys
385                 390                 395                 400

Ile Arg Ser Leu Glu Gln Arg Ile Val Glu Leu Ser Glu Ala Asn Lys
                405                 410                 415

Leu Ala Ala Asn Ser Ser Leu Phe Thr Gln Arg Asn Met Lys Ala Gln
            420                 425                 430

Glu Glu Met Ile Ser Glu Leu Arg Gln Gln Lys Phe Tyr Leu Glu Thr
        435                 440                 445

Gln Ala Gly Lys Leu Glu Ala Gln Asn Arg Lys Leu Glu Glu Gln Leu
    450                 455                 460

Glu Lys Ile Ser His Gln Asp His Ser Asp Lys Ser Arg Leu Leu Glu
465                 470                 475                 480

Leu Glu Thr Arg Leu Arg Glu Val Ser Leu Glu His Glu Glu Gln Lys
                485                 490                 495

Leu Glu Leu Lys Arg Gln Leu Thr Glu Leu Gln Leu Ser Leu Gln Glu
            500                 505                 510

Arg Glu Ser Gln Leu Thr Ala Leu Gln Ala Ala Arg Ala Ala Leu Glu
        515                 520                 525

Ser Gln Leu Arg Gln Ala Lys Thr Glu Leu Glu Glu Thr Thr Ala Glu
    530                 535                 540

Ala Glu Glu Glu Ile Gln Ala Leu Thr Ala His Arg Asp Glu Ile Gln
545                 550                 555                 560

Arg Lys Phe Asp Ala Leu Arg Asn Ser Cys Thr Val Ile Thr Asp Leu
                565                 570                 575

Glu Glu Gln Leu Asn Gln Leu Thr Glu Asp Asn Ala Glu Leu Asn Asn
            580                 585                 590

Gln Asn Phe Tyr Leu Ser Lys Gln Leu Asp Glu Ala Ser Gly Ala Asn
        595                 600                 605

Asp Glu Ile Val Gln Leu Arg Ser Glu Val Asp His Leu Arg Arg Glu
    610                 615                 620

Ile Thr Glu Arg Glu Met Gln Leu Thr Ser Gln Lys Gln Thr Met Glu
625                 630                 635                 640

Ala Leu Lys Thr Thr Cys Thr Met Leu Glu Glu Gln Val Leu Asp Leu
                645                 650                 655

Glu Ala Leu Asn Asp Glu Leu Leu Glu Lys Glu Arg Gln Trp Glu Ala
            660                 665                 670

Trp Arg Ser Val Leu Gly Asp Glu Lys Ser Gln Phe Glu Cys Arg Val
        675                 680                 685

Arg Glu Leu Gln Arg Met Leu Asp Thr Glu Lys Gln Ser Arg Ala Arg
    690                 695                 700

Ala Asp Gln Arg Ile Thr Glu Ser Arg Gln Val Val Glu Leu Ala Val
705                 710                 715                 720

Lys Glu His Lys Ala Glu Ile Leu Ala Leu Gln Gln Ala Leu Lys Glu
                725                 730                 735

Gln Lys Leu Lys Ala Glu Ser Leu Ser Asp Lys Leu Asn Asp Leu Glu
            740                 745                 750

Lys Lys His Ala Met Leu Glu Met Asn Ala Arg Ser Leu Gln Gln Lys
```

-continued

```
        755                 760                 765

Leu Glu Thr Glu Arg Glu Leu Lys Gln Arg Leu Leu Glu Glu Gln Ala
    770                 775                 780

Lys Leu Gln Gln Gln Met Asp Leu Gln Lys Asn His Ile Phe Arg Leu
785                 790                 795                 800

Thr Gln Gly Leu Gln Glu Ala Leu Asp Arg Ala Asp Leu Leu Lys Thr
                805                 810                 815

Glu Arg Ser Asp Leu Glu Tyr Gln Leu Glu Asn Ile Gln Val Leu Tyr
            820                 825                 830

Ser His Glu Lys Val Lys Met Glu Gly Thr Ile Ser Gln Gln Thr Lys
        835                 840                 845

Leu Ile Asp Phe Leu Gln Ala Lys Met Asp Gln Pro Ala Lys Lys Lys
    850                 855                 860

Lys Val Pro Leu Gln Tyr Asn Glu Leu Lys Leu Ala Leu Glu Lys Glu
865                 870                 875                 880

Lys Ala Arg Cys Ala Glu Leu Glu Glu Ala Leu Gln Lys Thr Arg Ile
                885                 890                 895

Glu Leu Arg Ser Ala Arg Glu Glu Ala Ala His Arg Lys Ala Thr Asp
            900                 905                 910

His Pro His Pro Ser Thr Pro Ala Thr Ala Arg Gln Gln Ile Ala Met
        915                 920                 925

Ser Ala Ile Val Arg Ser Pro Glu His Gln Pro Ser Ala Met Ser Leu
    930                 935                 940

Leu Ala Pro Pro Ser Ser Arg Arg Lys Glu Ser Ser Thr Pro Glu Glu
945                 950                 955                 960

Phe Ser Arg Arg Leu Lys Glu Arg Met His His Asn Ile Pro His Arg
                965                 970                 975

Phe Asn Val Gly Leu Asn Met Arg Ala Thr Lys Cys Ala Val Cys Leu
            980                 985                 990

Asp Thr Val His Phe Gly Arg Gln Ala Ser Lys Cys Leu Glu Cys Gln
        995                 1000                1005

Val Met Cys His Pro Lys Cys Ser Thr Cys Leu Pro Ala Thr Cys Gly
   1010                1015                1020

Leu Pro Ala Glu Tyr Ala Thr His Phe Thr Glu Ala Phe Cys Arg Asp
1025               1030                1035                1040

Lys Met Asn Ser Pro Gly Leu Gln Ser Lys Glu Pro Gly Ser Ser Leu
               1045                1050                1055

His Leu Glu Gly Trp Met Lys Val Pro Arg Asn Asn Lys Arg Gly Gln
           1060                1065                1070

Gln Gly Trp Asp Arg Lys Tyr Ile Val Leu Glu Gly Ser Lys Val Leu
       1075                1080                1085

Ile Tyr Asp Asn Glu Ala Arg Glu Ala Gly Gln Arg Pro Val Glu Glu
   1090                1095                1100

Phe Glu Leu Cys Leu Pro Asp Gly Asp Val Ser Ile His Gly Ala Val
1105               1110                1115                1120

Gly Ala Ser Glu Leu Ala Asn Thr Ala Lys Ala Asp Val Pro Tyr Ile
               1125                1130                1135

Leu Lys Met Glu Ser His Pro His Thr Thr Cys Trp Pro Gly Arg Thr
           1140                1145                1150

Leu Tyr Leu Leu Ala Pro Ser Phe Pro Asp Lys Gln Arg Trp Val Thr
       1155                1160                1165

Ala Leu Glu Ser Val Val Ala Gly Gly Arg Val Ser Arg Glu Lys Ala
   1170                1175                1180
```

-continued

```
Glu Ala Asp Ala Lys Leu Leu Gly Asn Ser Leu Leu Lys Leu Glu Gly
1185                1190                1195                1200

Asp Asp Arg Leu Asp Met Asn Cys Thr Leu Pro Phe Ser Asp Gln Val
                1205                1210                1215

Val Leu Val Gly Thr Glu Glu Gly Leu Tyr Ala Leu Asn Val Leu Lys
            1220                1225                1230

Asn Ser Leu Thr His Ile Pro Gly Ile Gly Ala Val Phe Gln Ile Tyr
        1235                1240                1245

Ile Ile Lys Asp Leu Glu Lys Leu Leu Met Ile Ala Gly Glu Glu Arg
    1250                1255                1260

Ala Leu Cys Leu Val Asp Val Lys Lys Val Lys Gln Ser Leu Ala Gln
1265                1270                1275                1280

Ser His Leu Pro Ala Gln Pro Asp Val Ser Pro Asn Ile Phe Glu Ala
                1285                1290                1295

Val Lys Gly Cys His Leu Phe Ala Ala Gly Lys Ile Glu Asn Ser Leu
            1300                1305                1310

Cys Ile Cys Ala Ala Met Pro Ser Lys Val Val Ile Leu Arg Tyr Asn
        1315                1320                1325

Asp Asn Leu Ser Lys Tyr Cys Ile Arg Lys Glu Ile Glu Thr Ser Glu
    1330                1335                1340

Pro Cys Ser Cys Ile His Phe Thr Asn Tyr Ser Ile Leu Ile Gly Thr
1345                1350                1355                1360

Asn Lys Phe Tyr Glu Ile Asp Met Lys Gln Tyr Thr Leu Asp Glu Phe
                1365                1370                1375

Leu Asp Lys Asn Asp His Ser Leu Ala Pro Ala Val Phe Ala Ser Ser
            1380                1385                1390

Ser Asn Ser Phe Pro Val Ser Ile Val Gln Ala Asn Ser Ala Gly Gln
        1395                1400                1405

Arg Glu Glu Tyr Leu Leu Cys Phe His Glu Phe Gly Val Phe Val Asp
    1410                1415                1420

Ser Tyr Gly Arg Arg Ser Arg Thr Asp Asp Leu Lys Trp Ser Arg Leu
1425                1430                1435                1440

Pro Leu Ala Phe Ala Tyr Arg Glu Pro Tyr Leu Phe Val Thr His Phe
                1445                1450                1455

Asn Ser Leu Glu Val Ile Glu Ile Gln Ala Arg Ser Ser Leu Gly Ser
            1460                1465                1470

Pro Ala Arg Ala Tyr Leu Glu Ile Pro Asn Pro Arg Tyr Leu Gly Pro
        1475                1480                1485

Ala Ile Ser Ser Gly Ala Ile Tyr Leu Ala Ser Ser Tyr Gln Asp Lys
    1490                1495                1500

Leu Arg Val Ile Cys Cys Lys Gly Asn Leu Val Lys Glu Ser Gly Thr
1505                1510                1515                1520

Glu Gln His Arg Val Pro Ser Thr Ser Arg Ser Ser Pro Asn Lys Arg
                1525                1530                1535

Gly Pro Pro Thr Tyr Asn Glu His Ile Thr Lys Arg Val Ala Ser Ser
            1540                1545                1550

Pro Ala Pro Pro Glu Gly Pro Ser His Pro Arg Glu Pro Ser Thr Pro
        1555                1560                1565

His Arg Tyr Arg Asp Arg Glu Gly Arg Thr Glu Leu Arg Arg Asp Lys
    1570                1575                1580

Ser Pro Gly Arg Pro Leu Glu Arg Glu Lys Ser Pro Gly Arg Met Leu
1585                1590                1595                1600
```

```
Ser Thr Arg Arg Glu Arg Ser Pro Gly Arg Leu Phe Glu Asp Ser Ser
               1605                1610                1615

Arg Gly Arg Leu Pro Ala Gly Ala Val Arg Thr Pro Leu Ser Gln Val
           1620                1625                1630

Asn Lys Val Trp Asp Gln Ser Ser Val
       1635                1640


<210> SEQ ID NO 6
<211> LENGTH: 1597
<212> TYPE: PRT
<213> ORGANISM: Mus musculus

<400> SEQUENCE: 6

Met Leu Leu Gly Glu Glu Ala Met Met Glu Gln Glu Met Thr Arg Leu
  1               5                  10                  15

His Arg Arg Val Ser Glu Val Glu Ala Val Leu Ser Gln Lys Glu Val
             20                  25                  30

Glu Leu Lys Ala Ser Glu Thr Gln Arg Ser Leu Leu Glu Gln Asp Leu
         35                  40                  45

Ala Thr Tyr Ile Thr Glu Cys Ser Ser Leu Lys Arg Ser Leu Glu Gln
     50                  55                  60

Ala Arg Met Glu Val Ser Gln Glu Asp Asp Lys Ala Leu Gln Leu Leu
 65                  70                  75                  80

His Asp Ile Arg Glu Gln Ser Arg Lys Leu Gln Glu Ile Lys Glu Gln
                 85                  90                  95

Glu Tyr Gln Ala Gln Val Glu Glu Met Arg Leu Met Met Asn Gln Leu
            100                 105                 110

Glu Glu Asp Leu Val Ser Ala Arg Arg Arg Ser Asp Leu Tyr Glu Ser
        115                 120                 125

Glu Leu Arg Glu Ser Arg Leu Ala Ala Glu Glu Phe Lys Arg Lys Ala
    130                 135                 140

Asn Glu Cys Gln His Lys Leu Met Lys Ala Lys Asp Gln Gly Lys Pro
145                 150                 155                 160

Glu Val Gly Glu Tyr Ser Lys Leu Glu Lys Ile Asn Ala Glu Gln Gln
                165                 170                 175

Leu Lys Ile Gln Glu Leu Gln Glu Lys Leu Glu Lys Ala Val Lys Ala
            180                 185                 190

Ser Thr Glu Ala Thr Glu Leu Leu Gln Asn Ile Arg Gln Ala Lys Glu
        195                 200                 205

Arg Ala Glu Arg Glu Leu Glu Lys Leu His Asn Arg Glu Asp Ser Ser
    210                 215                 220

Glu Gly Ile Lys Lys Lys Leu Val Glu Ala Glu Glu Arg Arg His Ser
225                 230                 235                 240

Leu Glu Asn Lys Val Lys Arg Leu Glu Thr Met Glu Arg Arg Glu Asn
                245                 250                 255

Arg Leu Lys Asp Asp Ile Gln Thr Lys Ser Glu Gln Ile Gln Gln Met
            260                 265                 270

Ala Asp Lys Ile Leu Glu Leu Glu Glu Lys His Arg Glu Ala Gln Val
        275                 280                 285

Ser Ala Gln His Leu Glu Val His Leu Lys Gln Lys Glu Gln His Tyr
    290                 295                 300

Glu Glu Lys Ile Lys Val Leu Asp Asn Gln Ile Lys Lys Asp Leu Ala
305                 310                 315                 320

Asp Lys Glu Ser Leu Glu Asn Met Met Gln Arg His Glu Glu Glu Ala
                325                 330                 335
```

-continued

```
His Glu Lys Gly Lys Ile Leu Ser Glu Gln Lys Ala Met Ile Asn Ala
            340                 345                 350

Met Asp Ser Lys Ile Arg Ser Leu Glu Gln Arg Ile Val Glu Leu Ser
        355                 360                 365

Glu Ala Asn Lys Leu Ala Ala Asn Ser Ser Leu Phe Thr Gln Arg Asn
    370                 375                 380

Met Lys Ala Gln Glu Glu Met Ile Ser Glu Leu Arg Gln Gln Lys Phe
385                 390                 395                 400

Tyr Leu Glu Thr Gln Ala Gly Lys Leu Glu Ala Gln Asn Arg Lys Leu
                405                 410                 415

Glu Glu Gln Leu Glu Lys Ile Ser His Gln Asp His Ser Asp Lys Ser
            420                 425                 430

Arg Leu Leu Glu Leu Glu Thr Arg Leu Arg Glu Val Ser Leu Glu His
        435                 440                 445

Glu Glu Gln Lys Leu Glu Leu Lys Arg Gln Leu Thr Glu Leu Gln Leu
    450                 455                 460

Ser Leu Gln Glu Arg Glu Ser Gln Leu Thr Ala Leu Gln Ala Ala Arg
465                 470                 475                 480

Ala Ala Leu Glu Ser Gln Leu Arg Gln Ala Lys Thr Glu Leu Glu Glu
                485                 490                 495

Thr Thr Ala Glu Ala Glu Glu Glu Ile Gln Ala Leu Thr Ala His Arg
            500                 505                 510

Asp Glu Ile Gln Arg Lys Phe Asp Ala Leu Arg Asn Ser Cys Thr Val
        515                 520                 525

Ile Thr Asp Leu Glu Glu Gln Leu Asn Gln Leu Thr Glu Asp Asn Ala
    530                 535                 540

Glu Leu Asn Asn Gln Asn Phe Tyr Leu Ser Lys Gln Leu Asp Glu Ala
545                 550                 555                 560

Ser Gly Ala Asn Asp Glu Ile Val Gln Leu Arg Ser Glu Val Asp His
                565                 570                 575

Leu Arg Arg Glu Ile Thr Glu Arg Glu Met Gln Leu Thr Ser Gln Lys
            580                 585                 590

Gln Thr Met Glu Ala Leu Lys Thr Thr Cys Thr Met Leu Glu Glu Gln
        595                 600                 605

Val Leu Asp Leu Glu Ala Leu Asn Asp Glu Leu Leu Glu Lys Glu Arg
    610                 615                 620

Gln Trp Glu Ala Trp Arg Ser Val Leu Gly Asp Glu Lys Ser Gln Phe
625                 630                 635                 640

Glu Cys Arg Val Arg Glu Leu Gln Arg Met Leu Asp Thr Glu Lys Gln
                645                 650                 655

Ser Arg Ala Arg Ala Asp Gln Arg Ile Thr Glu Ser Arg Gln Val Val
            660                 665                 670

Glu Leu Ala Val Lys Glu His Lys Ala Glu Ile Leu Ala Leu Gln Gln
        675                 680                 685

Ala Leu Lys Glu Gln Lys Leu Lys Ala Glu Ser Leu Ser Asp Lys Leu
    690                 695                 700

Asn Asp Leu Glu Lys Lys His Ala Met Leu Glu Met Asn Ala Arg Ser
705                 710                 715                 720

Leu Gln Gln Lys Leu Glu Thr Glu Arg Glu Leu Lys Gln Arg Leu Leu
                725                 730                 735

Glu Glu Gln Ala Lys Leu Gln Gln Gln Met Asp Leu Gln Lys Asn His
            740                 745                 750
```

-continued

```
Ile Phe Arg Leu Thr Gln Gly Leu Gln Glu Ala Leu Asp Arg Ala Asp
        755                 760                 765

Leu Leu Lys Thr Glu Arg Ser Asp Leu Glu Tyr Gln Leu Glu Asn Ile
    770                 775                 780

Gln Val Leu Tyr Ser His Glu Lys Val Lys Met Glu Gly Thr Ile Ser
785                 790                 795                 800

Gln Gln Thr Lys Leu Ile Asp Phe Leu Gln Ala Lys Met Asp Gln Pro
                805                 810                 815

Ala Lys Lys Lys Lys Val Pro Leu Gln Tyr Asn Glu Leu Lys Leu Ala
            820                 825                 830

Leu Glu Lys Glu Lys Ala Arg Cys Ala Glu Leu Glu Glu Ala Leu Gln
        835                 840                 845

Lys Thr Arg Ile Glu Leu Arg Ser Ala Arg Glu Glu Ala Ala His Arg
    850                 855                 860

Lys Ala Thr Asp His Pro His Pro Ser Thr Pro Ala Thr Ala Arg Gln
865                 870                 875                 880

Gln Ile Ala Met Ser Ala Ile Val Arg Ser Pro Glu His Gln Pro Ser
                885                 890                 895

Ala Met Ser Leu Leu Ala Pro Pro Ser Ser Arg Arg Lys Glu Ser Ser
            900                 905                 910

Thr Pro Glu Glu Phe Ser Arg Arg Leu Lys Glu Arg Met His His Asn
        915                 920                 925

Ile Pro His Arg Phe Asn Val Gly Leu Asn Met Arg Ala Thr Lys Cys
    930                 935                 940

Ala Val Cys Leu Asp Thr Val His Phe Gly Arg Gln Ala Ser Lys Cys
945                 950                 955                 960

Leu Glu Cys Gln Val Met Cys His Pro Lys Cys Ser Thr Cys Leu Pro
                965                 970                 975

Ala Thr Cys Gly Leu Pro Ala Glu Tyr Ala Thr His Phe Thr Glu Ala
            980                 985                 990

Phe Cys Arg Asp Lys Met Asn Ser Pro Gly Leu Gln Ser Lys Glu Pro
        995                 1000                1005

Gly Ser Ser Leu His Leu Glu Gly Trp Met Lys Val Pro Arg Asn Asn
    1010                1015                1020

Lys Arg Gly Gln Gln Gly Trp Asp Arg Lys Tyr Ile Val Leu Glu Gly
1025                1030                1035                1040

Ser Lys Val Leu Ile Tyr Asp Asn Glu Ala Arg Glu Ala Gly Gln Arg
                1045                1050                1055

Pro Val Glu Glu Phe Glu Leu Cys Leu Pro Asp Gly Asp Val Ser Ile
            1060                1065                1070

His Gly Ala Val Gly Ala Ser Glu Leu Ala Asn Thr Ala Lys Ala Asp
        1075                1080                1085

Val Pro Tyr Ile Leu Lys Met Glu Ser His Pro His Thr Thr Cys Trp
    1090                1095                1100

Pro Gly Arg Thr Leu Tyr Leu Leu Ala Pro Ser Phe Pro Asp Lys Gln
1105                1110                1115                1120

Arg Trp Val Thr Ala Leu Glu Ser Val Val Ala Gly Gly Arg Val Ser
                1125                1130                1135

Arg Glu Lys Ala Glu Ala Asp Ala Lys Leu Leu Gly Asn Ser Leu Leu
            1140                1145                1150

Lys Leu Glu Gly Asp Asp Arg Leu Asp Met Asn Cys Thr Leu Pro Phe
        1155                1160                1165

Ser Asp Gln Val Val Leu Val Gly Thr Glu Glu Gly Leu Tyr Ala Leu
```

-continued

```
   1170                1175                1180

Asn Val Leu Lys Asn Ser Leu Thr His Ile Pro Gly Ile Gly Ala Val
1185                1190                1195                1200

Phe Gln Ile Tyr Ile Ile Lys Asp Leu Glu Lys Leu Leu Met Ile Ala
                1205                1210                1215

Gly Glu Glu Arg Ala Leu Cys Leu Val Asp Val Lys Lys Val Lys Gln
            1220                1225                1230

Ser Leu Ala Gln Ser His Leu Pro Ala Gln Pro Asp Val Ser Pro Asn
        1235                1240                1245

Ile Phe Glu Ala Val Lys Gly Cys His Leu Phe Ala Ala Gly Lys Ile
    1250                1255                1260

Glu Asn Ser Leu Cys Ile Cys Ala Ala Met Pro Ser Lys Val Val Ile
1265                1270                1275                1280

Leu Arg Tyr Asn Asp Asn Leu Ser Lys Tyr Cys Ile Arg Lys Glu Ile
                1285                1290                1295

Glu Thr Ser Glu Pro Cys Ser Cys Ile His Phe Thr Asn Tyr Ser Ile
            1300                1305                1310

Leu Ile Gly Thr Asn Lys Phe Tyr Glu Ile Asp Met Lys Gln Tyr Thr
        1315                1320                1325

Leu Asp Glu Phe Leu Asp Lys Asn Asp His Ser Leu Ala Pro Ala Val
    1330                1335                1340

Phe Ala Ser Ser Ser Asn Ser Phe Pro Val Ser Ile Val Gln Ala Asn
1345                1350                1355                1360

Ser Ala Gly Gln Arg Glu Glu Tyr Leu Leu Cys Phe His Glu Phe Gly
                1365                1370                1375

Val Phe Val Asp Ser Tyr Gly Arg Arg Ser Arg Thr Asp Asp Leu Lys
            1380                1385                1390

Trp Ser Arg Leu Pro Leu Ala Phe Ala Tyr Arg Glu Pro Tyr Leu Phe
        1395                1400                1405

Val Thr His Phe Asn Ser Leu Glu Val Ile Glu Ile Gln Ala Arg Ser
    1410                1415                1420

Ser Leu Gly Ser Pro Ala Arg Ala Tyr Leu Glu Ile Pro Asn Pro Arg
1425                1430                1435                1440

Tyr Leu Gly Pro Ala Ile Ser Ser Gly Ala Ile Tyr Leu Ala Ser Ser
                1445                1450                1455

Tyr Gln Asp Lys Leu Arg Val Ile Cys Cys Lys Gly Asn Leu Val Lys
            1460                1465                1470

Glu Ser Gly Thr Glu Gln His Arg Val Pro Ser Thr Ser Arg Ser Ser
        1475                1480                1485

Pro Asn Lys Arg Gly Pro Pro Thr Tyr Asn Glu His Ile Thr Lys Arg
    1490                1495                1500

Val Ala Ser Ser Pro Ala Pro Pro Glu Gly Pro Ser His Pro Arg Glu
1505                1510                1515                1520

Pro Ser Thr Pro His Arg Tyr Arg Asp Arg Glu Gly Arg Thr Glu Leu
                1525                1530                1535

Arg Arg Asp Lys Ser Pro Gly Arg Pro Leu Glu Arg Glu Lys Ser Pro
            1540                1545                1550

Gly Arg Met Leu Ser Thr Arg Arg Glu Arg Ser Pro Gly Arg Leu Phe
        1555                1560                1565

Glu Asp Ser Ser Arg Gly Arg Leu Pro Ala Gly Ala Val Arg Thr Pro
    1570                1575                1580

Leu Ser Gln Val Asn Lys Val Trp Asp Gln Ser Ser Val
1585                1590                1595
```

```
<210> SEQ ID NO 7
<211> LENGTH: 1286
<212> TYPE: PRT
<213> ORGANISM: Homo sapiens

<400> SEQUENCE: 7

Val Leu Asp Asn Gln Ile Lys Lys Asp Leu Ala Asp Lys Glu Thr Leu
  1               5                  10                  15

Glu Asn Met Met Gln Arg His Glu Glu Glu Ala His Glu Lys Gly Lys
             20                  25                  30

Ile Leu Ser Glu Gln Lys Ala Met Ile Asn Ala Met Asp Ser Lys Ile
         35                  40                  45

Arg Ser Leu Glu Gln Arg Ile Val Glu Leu Ser Glu Ala Asn Lys Leu
     50                  55                  60

Ala Ala Asn Ser Ser Leu Phe Thr Gln Arg Asn Met Lys Ala Gln Glu
 65                  70                  75                  80

Glu Met Ile Ser Glu Leu Arg Gln Gln Lys Phe Tyr Leu Glu Thr Gln
                 85                  90                  95

Ala Gly Lys Leu Glu Ala Gln Asn Arg Lys Leu Glu Glu Gln Leu Glu
            100                 105                 110

Lys Ile Ser His Gln Asp His Ser Asp Lys Asn Arg Leu Leu Glu Leu
        115                 120                 125

Glu Thr Arg Leu Arg Glu Val Ser Leu Glu His Glu Glu Gln Lys Leu
    130                 135                 140

Glu Leu Lys Arg Gln Leu Thr Glu Leu Gln Leu Ser Leu Gln Glu Arg
145                 150                 155                 160

Glu Ser Gln Leu Thr Ala Leu Gln Ala Ala Arg Ala Ala Leu Glu Ser
                165                 170                 175

Gln Leu Arg Gln Ala Lys Thr Glu Leu Glu Glu Thr Thr Ala Glu Ala
            180                 185                 190

Glu Glu Glu Ile Gln Ala Leu Thr Ala His Arg Asp Glu Ile Gln Arg
        195                 200                 205

Lys Phe Asp Ala Leu Arg Asn Ser Cys Thr Val Ile Thr Asp Leu Glu
    210                 215                 220

Glu Gln Leu Asn Gln Leu Thr Glu Asp Asn Ala Glu Leu Asn Asn Gln
225                 230                 235                 240

Asn Phe Tyr Leu Ser Lys Gln Leu Asp Glu Ala Ser Gly Ala Asn Asp
                245                 250                 255

Glu Ile Val Gln Leu Arg Ser Glu Val Asp His Leu Arg Arg Glu Ile
            260                 265                 270

Thr Glu Arg Glu Met Gln Leu Thr Ser Gln Lys Gln Thr Met Glu Ala
        275                 280                 285

Leu Lys Thr Thr Cys Thr Met Leu Glu Glu Gln Val Met Asp Leu Glu
    290                 295                 300

Ala Leu Asn Asp Glu Leu Leu Glu Lys Glu Arg Gln Trp Glu Ala Trp
305                 310                 315                 320

Arg Ser Val Leu Gly Asp Glu Lys Ser Gln Phe Glu Cys Arg Val Arg
                325                 330                 335

Glu Leu Gln Arg Met Leu Asp Thr Glu Lys Gln Ser Arg Ala Arg Ala
            340                 345                 350

Asp Gln Arg Ile Thr Glu Ser Arg Gln Val Val Glu Leu Ala Val Lys
        355                 360                 365

Glu His Lys Ala Glu Ile Leu Ala Leu Gln Gln Ala Leu Lys Glu Gln
```

-continued

```
    370             375             380

Lys Leu Lys Ala Glu Ser Leu Ser Asp Lys Leu Asn Asp Leu Glu Lys
385                 390                 395                 400

Lys His Ala Met Leu Glu Met Asn Ala Arg Ser Leu Gln Gln Lys Leu
                405                 410                 415

Glu Thr Glu Arg Glu Leu Lys Gln Arg Leu Leu Glu Glu Gln Ala Lys
            420                 425                 430

Leu Gln Gln Gln Met Asp Leu Gln Lys Asn His Ile Phe Arg Leu Thr
        435                 440                 445

Gln Gly Leu Gln Glu Ala Leu Asp Arg Ala Asp Leu Leu Lys Thr Glu
    450                 455                 460

Arg Ser Asp Leu Glu Tyr Gln Leu Glu Asn Ile Gln Val Leu Tyr Ser
465                 470                 475                 480

His Glu Lys Val Lys Met Glu Gly Thr Ile Ser Gln Gln Thr Lys Leu
                485                 490                 495

Ile Asp Phe Leu Gln Ala Lys Met Asp Gln Pro Ala Lys Lys Lys Lys
            500                 505                 510

Val Pro Leu Gln Tyr Asn Glu Leu Lys Leu Ala Leu Glu Lys Glu Lys
        515                 520                 525

Ala Arg Cys Ala Glu Leu Glu Glu Ala Leu Gln Lys Thr Arg Ile Glu
    530                 535                 540

Leu Arg Ser Ala Arg Glu Glu Ala Ala His Arg Lys Ala Thr Asp His
545                 550                 555                 560

Pro His Pro Ser Thr Pro Ala Thr Ala Arg Gln Gln Ile Ala Met Ser
                565                 570                 575

Ala Ile Val Arg Ser Pro Glu His Gln Pro Ser Ala Met Ser Leu Leu
            580                 585                 590

Ala Pro Pro Ser Ser Arg Arg Lys Glu Ser Ser Thr Pro Glu Glu Phe
        595                 600                 605

Ser Arg Arg Leu Lys Glu Arg Met His His Asn Ile Pro His Arg Phe
    610                 615                 620

Asn Val Gly Leu Asn Met Arg Ala Thr Lys Cys Ala Val Cys Leu Asp
625                 630                 635                 640

Thr Val His Phe Gly Arg Gln Ala Ser Lys Cys Leu Glu Cys Gln Val
                645                 650                 655

Met Cys His Pro Lys Cys Ser Thr Cys Leu Pro Ala Thr Cys Gly Leu
            660                 665                 670

Pro Ala Glu Tyr Ala Thr His Phe Thr Glu Ala Phe Cys Arg Asp Lys
        675                 680                 685

Met Asn Ser Pro Gly Leu Gln Thr Lys Glu Pro Ser Ser Ser Leu His
    690                 695                 700

Leu Glu Gly Trp Met Lys Val Pro Arg Asn Asn Lys Arg Gly Gln Gln
705                 710                 715                 720

Gly Trp Asp Arg Lys Tyr Ile Val Leu Glu Gly Ser Lys Val Leu Ile
                725                 730                 735

Tyr Asp Asn Glu Ala Arg Glu Ala Gly Gln Arg Pro Val Glu Glu Phe
            740                 745                 750

Glu Leu Cys Leu Pro Asp Gly Asp Val Ser Ile His Gly Ala Val Gly
        755                 760                 765

Ala Ser Glu Leu Ala Asn Thr Ala Lys Ala Asp Val Pro Tyr Ile Leu
    770                 775                 780

Lys Met Glu Ser His Pro His Thr Thr Cys Trp Pro Gly Arg Thr Leu
785                 790                 795                 800
```

-continued

```
Tyr Leu Leu Ala Pro Ser Phe Pro Asp Lys Gln Arg Trp Val Thr Ala
                805                 810                 815

Leu Glu Ser Val Val Ala Gly Gly Arg Val Ser Arg Glu Lys Ala Glu
            820                 825                 830

Ala Asp Ala Lys Leu Leu Gly Asn Ser Leu Leu Lys Leu Glu Gly Asp
        835                 840                 845

Asp Arg Leu Asp Met Asn Cys Thr Leu Pro Phe Ser Asp Gln Val Val
    850                 855                 860

Leu Val Gly Thr Glu Glu Gly Leu Tyr Ala Leu Asn Val Leu Lys Asn
865                 870                 875                 880

Ser Leu Thr His Val Pro Gly Ile Gly Ala Val Phe Gln Ile Tyr Ile
                885                 890                 895

Ile Lys Asp Leu Glu Lys Leu Leu Met Ile Ala Gly Glu Glu Arg Ala
            900                 905                 910

Leu Cys Leu Val Asp Val Lys Lys Val Lys Gln Ser Leu Ala Gln Ser
        915                 920                 925

His Leu Pro Ala Gln Pro Asp Ile Ser Pro Asn Ile Phe Glu Ala Val
    930                 935                 940

Lys Gly Cys His Leu Phe Gly Ala Gly Lys Ile Glu Asn Gly Leu Cys
945                 950                 955                 960

Ile Cys Ala Ala Met Pro Ser Lys Val Val Ile Leu Arg Tyr Asn Glu
                965                 970                 975

Asn Leu Ser Lys Tyr Cys Ile Arg Lys Glu Ile Glu Thr Ser Glu Pro
            980                 985                 990

Cys Ser Cys Ile His Phe Thr Asn Tyr Ser Ile Leu Ile Gly Thr Asn
        995                1000                1005

Lys Phe Tyr Glu Ile Asp Met Lys Gln Tyr Thr Leu Glu Glu Phe Leu
   1010                1015                1020

Asp Lys Asn Asp His Ser Leu Ala Pro Ala Val Phe Ala Ala Ser Ser
1025                1030                1035                1040

Asn Ser Phe Pro Val Ser Ile Val Gln Val Asn Ser Ala Gly Gln Arg
               1045                1050                1055

Glu Glu Tyr Leu Leu Cys Phe His Glu Phe Gly Val Phe Val Asp Ser
           1060                1065                1070

Tyr Gly Arg Arg Ser Arg Thr Asp Asp Leu Lys Trp Ser Arg Leu Pro
       1075                1080                1085

Leu Ala Phe Ala Tyr Arg Glu Pro Tyr Leu Phe Val Thr His Phe Asn
   1090                1095                1100

Ser Leu Glu Val Ile Glu Ile Gln Ala Arg Ser Ser Ala Gly Thr Pro
1105                1110                1115                1120

Ala Arg Ala Tyr Leu Asp Ile Pro Asn Pro Arg Tyr Leu Gly Pro Ala
               1125                1130                1135

Ile Ser Ser Gly Ala Ile Tyr Leu Ala Ser Ser Tyr Gln Asp Lys Leu
           1140                1145                1150

Arg Val Ile Cys Cys Lys Gly Asn Leu Val Lys Glu Ser Gly Thr Glu
       1155                1160                1165

His His Arg Gly Pro Ser Thr Ser Arg Ser Ser Pro Asn Lys Arg Gly
   1170                1175                1180

Pro Pro Thr Tyr Asn Glu His Ile Thr Lys Arg Val Ala Ser Ser Pro
1185                1190                1195                1200

Ala Pro Pro Glu Gly Pro Ser His Pro Arg Glu Pro Ser Thr Pro His
               1205                1210                1215
```

-continued

```
Arg Tyr Arg Glu Gly Arg Thr Glu Leu Arg Arg Asp Lys Ser Pro Gly
            1220                1225                1230

Arg Pro Leu Glu Arg Glu Lys Ser Pro Gly Arg Met Leu Ser Thr Arg
        1235                1240                1245

Arg Glu Arg Ser Pro Gly Arg Leu Phe Glu Asp Ser Ser Arg Gly Arg
    1250                1255                1260

Leu Pro Ala Gly Ala Val Arg Thr Pro Leu Ser Gln Val Asn Lys Val
1265                1270                1275                1280

Trp Asp Gln Ser Ser Val
                1285
```